United States Patent
Ahrens et al.

(10) Patent No.: US 7,943,551 B2
(45) Date of Patent: May 17, 2011

(54) 3-CYCLOPROPYL-4-(3-THIOBENZOYL) PYRAZOLES AND THEIR USE AS HERBICIDES

(75) Inventors: Hartmut Ahrens, Egelsbach (DE); Andreas van Almsick, Karben (DE); Stefan Lehr, Liederbach (DE); Monika Schmitt, Frankfurt a. M. (DE); Jan Dittgen, Frankfurt a. M. (DE); Dieter Feucht, Eschborn (DE); Martin Hills, Idstein (DE); Heinz Kehne, Hofheim (DE); Christopher Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 383 days.

(21) Appl. No.: 12/135,602

(22) Filed: Jun. 9, 2008

(65) Prior Publication Data
US 2008/0305956 A1  Dec. 11, 2008

(30) Foreign Application Priority Data

Jun. 11, 2007  (DE) .......................... 10 2007 026 875

(51) Int. Cl.
*A01N 43/56* (2006.01)
*C07D 231/20* (2006.01)
*C07C 317/14* (2006.01)

(52) U.S. Cl. ...................... 504/282; 548/369.4; 568/37
(58) Field of Classification Search .................. None
See application file for complete search history.

(56) References Cited

U.S. PATENT DOCUMENTS

| 5,013,659 | A | 5/1991 | Bedbrook et al. | |
| 7,396,939 | B2 * | 7/2008 | Schmitt et al. ............. | 548/369.4 |
| 2009/0069184 | A1 * | 3/2009 | Ahrens et al. ................ | 504/282 |

FOREIGN PATENT DOCUMENTS

| DE | 25 13 750 | 10/1975 |
| DE | 100 39 723 | 7/2001 |
| EP | 0 142 924 | 5/1985 |
| EP | 0 186 117 | 7/1986 |
| EP | 0 193 259 | 9/1986 |
| EP | 0 221 044 | 5/1987 |
| EP | 0 240 001 | 10/1987 |
| EP | 0 242 236 | 10/1987 |
| EP | 0 242 246 | 10/1987 |
| EP | 0 257 993 | 3/1988 |
| EP | 0 527 036 | 2/1993 |
| EP | 0580439 A1 | 1/1994 |
| EP | 0 352 543 | 9/1994 |
| GB | 1447032 A | 8/1976 |
| WO | WO 84/02919 | 8/1984 |
| WO | WO 91/13972 | 9/1991 |
| WO | WO 91/19806 | 12/1991 |
| WO | WO 92/00377 | 1/1992 |
| WO | WO 92/11376 | 7/1992 |
| WO | WO 92/14827 | 9/1992 |
| WO | 94/02465 A1 | 2/1994 |
| WO | 94/18179 A1 | 8/1994 |
| WO | WO 97/41106 | 11/1997 |
| WO | WO 98/42648 | 10/1998 |
| WO | WO 98/42678 | 10/1998 |
| WO | WO 00/03993 | 1/2000 |
| WO | WO 03/014071 | 2/2003 |

OTHER PUBLICATIONS

International Search Report for PCT/EP2008/004262, mailed Jun. 5, 2009.
Isogai, A. et al., "New 3-cyclopropyl-4-carbonyl-5-hydroxypyrazole Derivatives Are Herbicides Useful for Wheat, Corn or Paddy Fields," Database WPI / Thompson, doc. No. XP-002500085.
Master, H.E. et al., "Preparation of 4'-amino-3-carboxy-6-methoxydiphenyl Sulfide and Its Derivatives," Journal of the Indian Chemical Society, 1978, Database CA, doc. No. XP-002500081.
Goghari, M.H. et al., "Fries Reaction. XV. Preparation of Hydroxydiaryl Sulfones," University Dep. Chem., Bhavnagar, India, Database CA, doc. No. XP-002500082.
Patwa, B.S. et al., "Fries Reaction—Part XI, Preparation of Hydroxydiarysulphones," J. Inst. Chemists (India), vol. VLVI, Jul. 1974, doc. No. XP-000600341, pp. 140-142.
Database Registry, Chemical Library, Mar. 7, 2001, doc. No. XP-002500083.
Database Registry, Chemical Library, Mar. 5, 2001, doc. No. XP-002500084.
Database Registry, Chemical Library, May 12, 2002, doc. No. XP-002524369.
Braun, H., et al. "The general mitochondrial processing peptidase from potato is an integral part of cytochrome c reductase of the respiratory chain." EMBO Journal. vol. 11 No. 9. pp. 3219-3227. 1992. Browning, JE. "Agglomeration:Growing Larger in Applications and Technologies." Chemical Engineering, 1967, p. 147-170.
Christou, P. "Transformation technology," Trends in Plant Science, Dec. 1996, vol. 1, No. 12, pp. 423-431.
Jensen, BS. "The synthesis of 1-Phenyl-3-methyl-4-acyl-pyrazolones-5." Acta Chem. Scan. 13 (1959) No. 8, pp. 1668-1670.
Siddall, T. et. al. "Synthesis and herbicidal activity of phenyl-substituted benzoylpyrazoles." Pest Management Science (2002),58(12):1175-1186.
Sonnewald, U. et al. "Transgenic tobacco plants expressing yeast-derived invertase in either the cytosol, vacuole, or apoplast: a powerful tool for studying sucrose metabolism and sink/source interactions." The Plant Journal (1991), 1 (1), p. 95-106.
Freyer, JD et. al. "Weed Control Handbook," 5th edition, Blackwell Scientific Publications, Oxfor, 1968, p. 101-103.
Klingman, GC. "Weed Control as a Science," John Wiley and Sonce, New York, 1961, pp. 81-96.
Wolter, F. "rbcS genes in *Solanum tuberosum*: Conservation of transit peptide and exon shuffling during evolution," PNAS, vol. 85, pp. 846-850, Feb. 1988.
Weed Research, 1986, vol. 26, pp. 441-445.

* cited by examiner

*Primary Examiner* — Kamal A Saeed
(74) *Attorney, Agent, or Firm* — Baker, Donelson, Bearman, Caldwell & Berkowitz, PC

(57) ABSTRACT

What is described are 3-cyclopropyl-4-(3-thiobenzoyl)pyrazoles of the general formula (I) and their use as herbicides

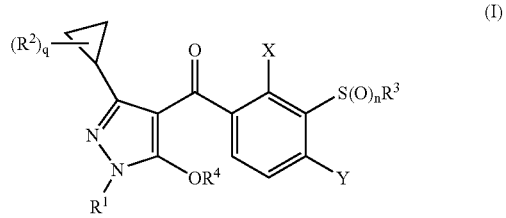

In this formula (I), $R^1$, $R^2$, $R^3$, X and Y are radicals such as hydrogen and organic radicals, such as alkyl. $R^4$ is hydrogen or a protective group, such as tosyl.

9 Claims, No Drawings

3-CYCLOPROPYL-4-(3-THIOBENZOYL) PYRAZOLES AND THEIR USE AS HERBICIDES

CROSS REFERENCE TO RELATED APPLICATION

This application claims priority from DE 10 2007 026 875.2 filed Jun. 11, 2007, the content of which is incorporated herein by reference in its entirety.

BACKGROUND OF THE INVENTION

1. Field of the Invention

The invention relates to the technical field of the herbicides, in particular that of the herbicides for the selective control of broad-leaved weeds and weed grasses in crops of useful plants.

2. Description of Related Art

From various publications, it is already known that certain 4-benzoylpyrazoles have herbicidal properties. Thus, EP 0 352 543 A1 mentions 4-benzoylpyrazoles which may be substituted in the phenyl ring, inter alia by a thio radical. WO 97/41106 and WO 00/03993 mention 3-cyclopropyl-4-benzoylpyrazoles which may be substituted in the phenyl ring, inter alia by a thio radical. The publications mentioned above do not disclose any embodiments of a substitution of the phenyl ring in the meta-position by a thio radical.

However, the herbicidal activity of the compounds known from these publications is frequently insufficient. It is therefore an object of the present invention to provide herbicidally active compounds having herbicidal properties which are better than those of the compounds disclosed in the prior art.

SUMMARY OF THE INVENTION

It has now been found that certain 4-benzoylpyrazoles which are substituted in the 3-position by a cyclopropyl group and whose phenyl ring carries a substituted sulfenyl, sulfinyl or sulfonyl group in the 3-position are particularly suitable for use as herbicides. Part of the subject matter of the present invention are 3-cyclopropyl-4-(3-thiobenzoyl)pyrazoles of the formula (I) or salts thereof

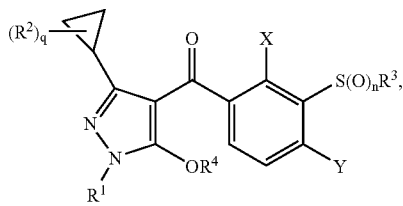

(I)

in which
$R^1$ is $(C_1-C_4)$-alkyl,
$R^2$ is halogen or $(C_1-C_4)$-alkyl,
$R^3$ is $(C_3-C_8)$-cycloalkyl, $(C_3-C_8)$-cycloalkyl-$(C_1-C_9)$-alkyl, $(C_2-C_6)$-alkenyl, $(C_2-C_6)$-alkynyl, $(C_1-C_6)$-haloalkyl, $(C_3-C_8)$-halocycloalkyl-$(C_1-C_9)$-alkyl, $(C_2-C_6)$-haloalkenyl, $(C_2-C_6)$-haloalkynyl, $(C_2-C_6)$-nitroalkyl, phenyl, $(C_3-C_8)$-cycloalkoxy-$(C_1-C_9)$-alkyl, $(C_3-C_8)$-cycloalkyl-$(C_1-C_9)$-alkoxy-$(C_1-C_9)$-alkyl, $(C_1-C_6)$-alkoxy-$(C_1-C_9)$-alkyl, $(C_2-C_6)$-alkenyloxy-$(C_1-C_9)$-alkyl, $(C_2-C_6)$-alkynyloxy-$(C_1-C_9)$-alkyl, $(C_1-C_6)$-haloalkoxy-$(C_1-C_9)$-alkyl, $(C_3-C_8)$-halocycloalkyl-$(C_1-C_9)$-alkoxy-$(C_1-C_9)$-alkyl, $(C_2-C_6)$-haloalkenyloxy-$(C_1-C_9)$-alkyl, $(C_2-C_6)$-haloalkynyloxy-$(C_1-C_9)$-alkyl, $(C_2-C_6)$-nitroalkoxy-$(C_1-C_9)$-alkyl, phenyloxy-$(C_1-C_9)$-alkyl, where the phenyl group may in each case be substituted by m identical or different radicals from the group consisting of $(C_1-C_3)$-alkyl, halogen, nitro, $(C_1-C_3)$-alkoxy, $R^4$ is hydrogen, $(C_1-C_6)$-alkylsulfonyl, $(C_1-C_4)$-alkoxy-$(C_1-C_6)$-alkylsulfonyl, or is phenylsulfonyl, thien-2-ylsulfonyl, benzoyl, (ethylthio)carbonyl, benzoyl-$(C_1-C_6)$-alkyl or benzyl, each of which is substituted by m identical or different radicals from the group consisting of halogen, $(C_1-C_4)$-alkyl and $(C_1-C_4)$-alkoxy, X and Y independently of one another are hydrogen, mercapto, nitro, halogen, cyano, thiocyanato, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_3-C_6)$-haloalkynyl, $(C_3-C_6)$-cycloalkyl, $OR^5$, methylsulfonylethoxymethyl, methylsulfonylethylsulfonylmethyl, methoxyethylsulfonylmethyl, $OCOR^5$, $OSO_2R^5$, $S(O)_nR^5$, $SO_2OR^5$, $SO_2N(R^5)_2$, $(C_1-C_3)$-alkoxy-$(C_1-C_3)$-alkoxy-$(C_1-C_3)$-alkyl, $NR^5SO_2R^5$, $NR^5COR^5$, $(C_1-C_6)$-alkyl-$S(O)_nR^5$, $(C_1-C_6)$-alkyl-$OR^5$, $(C_1-C_6)$-alkyl-$OCOR^5$, $(C_1-C_6)$-alkyl-$OSO_2R^5$, $(C_1-C_6)$-alkyl-$SO_2OR^5$, $(C_1-C_6)$-alkyl-$SO_2N(R^5)_2$ or $(C_1-C_6)$-alkyl-$NR^5COR^5$;

$R^5$ is hydrogen, $(C_1-C_6)$-alkyl, $(C_2-C_6)$-alkenyl, $(C_2-C_6)$-alkynyl, $(C_3-C_6)$-cycloalkyl, phenyl or phenyl-$(C_1-C_6)$-alkyl, where the six last mentioned radicals are substituted by s radicals from the group consisting of hydroxyl, mercapto, amino, cyano, nitro, thiocyanato, $OR^6$, $SR^6$, $N(R^6)_2$, $NOR^6$, $OCOR^6$, $SCOR^6$, $NR^6COR^6$, $CO_2R^6$, $COSR^6$, $CON(R^6)_2$, $(C_1-C_4)$-alkyliminooxy, $(C_1-C_4)$-alkoxyamino, $(C_1-C_4)$-alkylcarbonyl, $(C_1-C_4)$-alkoxy-$(C_2-C_6)$-alkoxycarbonyl and $(C_1-C_4)$-alkylsulfonyl;

$R^6$ is hydrogen, $(C_1-C_6)$-alkyl, $(C_2-C_6)$-alkenyl or $(C_2-C_6)$-alkynyl,
m is 0, 1, 2, 3, 4 or 5,
n is 0, 1 or 2,
q is 0, 1, 2, 3, 4 or 5,
s is 0, 1, 2 or 3,
with the proviso that $R^3$ is not $(C_1-C_6)$-haloalkyl if n is 0.

DETAILED DESCRIPTION OF A PREFERRED EMBODIMENT

Where $R^4$ is hydrogen, the compounds of the formula (I) according to the invention, depending on external conditions, such as solvent and pH, may occur in different tautomeric structures:

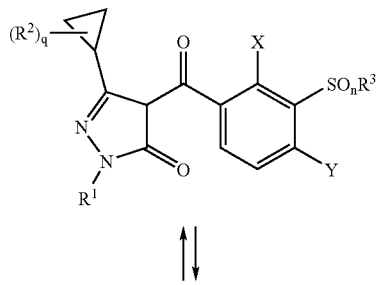

-continued

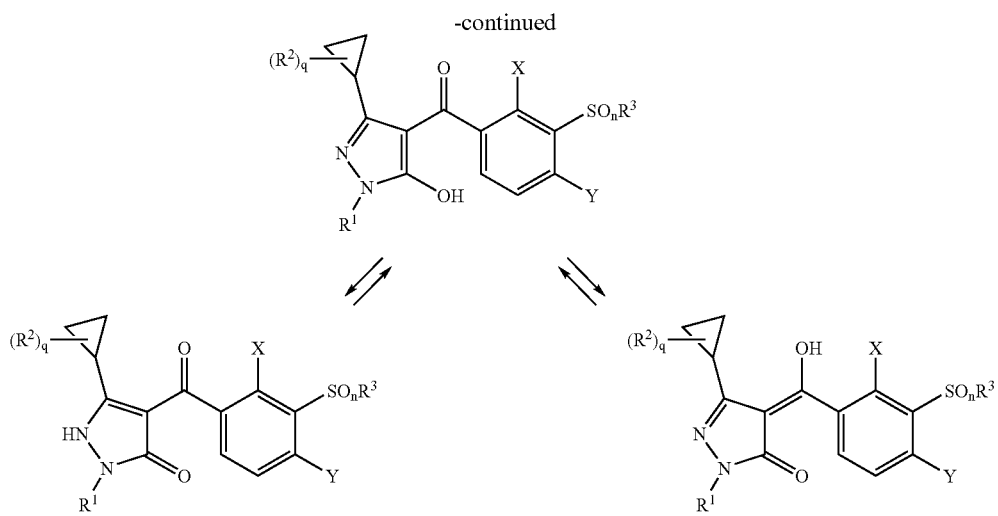

Depending on the nature of the substituents, the compounds of the general formula (I) contain an acidic proton which may be removed by reaction with a base. Suitable bases are, for example, hydrides, hydroxides and carbonates of lithium, sodium, potassium, magnesium and calcium, and also ammonia and organic amines, such as triethylamine and pyridine. It is also possible to form salts by forming adducts with organic acids, such as formic acid or acetic acid, and inorganic acids, such as phosphoric acid, hydrochloric acid or sulfuric acid. Such salts also form part of the subject matter of the invention.

In formula (I) and all subsequent formulae, alkyl radicals with more than two carbon atoms can be straight-chain or branched. Alkyl radicals are, for example, methyl, ethyl, n- or i-propyl, n-, i-, t- or 2-butyl, pentyls, hexyls, such as n-hexyl, i-hexyl and 1,3-dimethylbutyl. Halogen is fluorine, chlorine, bromine or iodine. Tosyl is 4-methylphenylsulfonyl.

If a group is polysubstituted by radicals, this is to be understood as meaning that this group is substituted by one or more identical or different of the radicals mentioned.

Depending on the type and the linkage of the substituents, the compounds of the general formula (I) can exist as stereoisomers. If, for example, one or more asymmetric carbon atoms are present, enantiomers and diastereomers may occur. Stereoisomers may also occur when n is 1. Stereoisomers can be obtained from the mixtures resulting from the preparation by means of customary separation methods, for example by chromatographic separation methods. Likewise, stereoisomers may be prepared selectively by using stereoselective reactions employing optically active starting materials and/or auxiliaries. The invention also relates to all stereoisomers and their mixtures which are encompassed by the general formula (I), but not defined specifically.

Preference is given to compounds of the general formula (I) in which:
$R^1$ is $(C_1-C_4)$-alkyl,
$R^2$ is halogen, methyl or ethyl,
$R^3$ is cyclopropyl, cyclopropylmethyl, cyclopropylmethoxyethyl, methoxyethyl, methoxypropyl, ethoxyethyl,
$R^4$ is hydrogen, n-propylsulfonyl, phenylsulfonyl, methoxyethylsulfonyl, benzoylmethyl, benzoyl, 4-methylbenzoylmethyl, (ethylthio)carbonyl, 4-methylphenylsulfonyl, thien-2-ylsulfonyl,
X is nitro, halogen, $(C_1-C_4)$-alkyl, trifluoromethyl, $(C_1-C_4)$-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, methylsulfonylethylsulfonylmethyl,
Y is halogen, trifluoromethyl, $(C_1-C_4)$-alkoxy, methylsulfonyl or ethylsulfonyl,
n is 0, 1 or 2,
q is 0, 1 or 2.

Particular preference is given to compounds of the general formula (I) in which
$R^1$ is methyl or ethyl,
$R^3$ is cyclopropyl, cyclopropylmethyl, cyclopropylmethoxyethyl, methoxyethyl, methoxypropyl, ethoxyethyl,
$R^4$ is hydrogen, n-propylsulfonyl, phenylsulfonyl, methoxyethylsulfonyl, benzoylmethyl, benzoyl, 4-methylbenzoylmethyl, (ethylthio)carbonyl, 4-methylphenylsulfonyl, thien-2-ylsulfonyl,
X is nitro, bromine, chlorine, fluorine, methyl, ethyl, trifluoromethyl, methoxy, ethoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, methylsulfonylethylsulfonylmethyl,
Y is bromine, chlorine, fluorine, trifluoromethyl, methoxy, methylsulfonyl or ethylsulfonyl,
n is 0, 1 or 2,
q is 0.

In all the formulae given below, the substituents and symbols have the same meaning as described under formula (I), unless defined otherwise.

Compounds according to the invention in which $R^4$ is hydrogen can be prepared, for example, by the process shown in scheme 1 and known from B. S. Jensen (Acta Chemica Scandinavica 13 (1959), 1668-1670) by base-catalyzed reaction of a benzoyl halide (III) with a pyrazolone (II), or by the process shown in scheme 2 and known, for example, from EP-A 0 186 117 by base-catalyzed reaction of a benzoyl halide (III) with a pyrazolone (II) and subsequent rearrangement.

Scheme 1

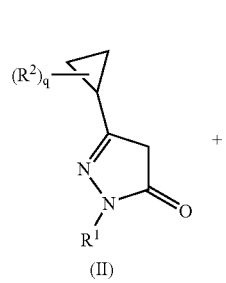

Scheme 3

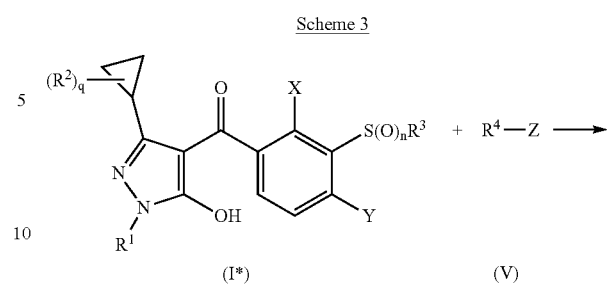

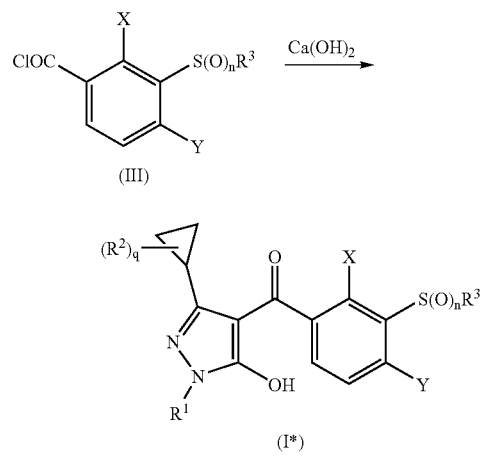

Scheme 2

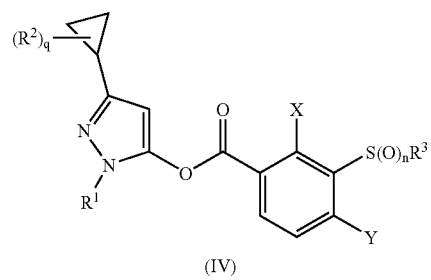

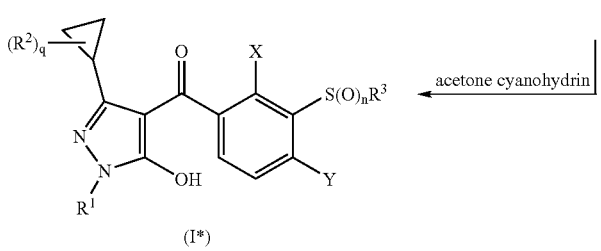

According to scheme 3, compounds according to the invention in which $R^4$ has a meaning different from hydrogen are expediently prepared from the compounds obtainable according to scheme 1 or 2, by base-catalyzed reaction with a suitable acylating agent $R^4$–Z of formula (V) in which Z is a leaving group, such as halogen. Such methods are known in principle to the person skilled in the art and described, for example, in DE-A 25 13 750.

Compounds according to the invention can also be prepared according to the process shown in scheme 4 and known from WO 98/42678 by reacting a pyrazolone(II) with a halobenzoyl chloride (IIIa), subsequent nucleophilic aromatic substitution with a thio compound HS—$R^3$ and, if appropriate, oxidation of the thio group. Here, L is, for example, chlorine, bromine, iodine or trifluoromethylsulfonyl. Such substitution reactions are known to the person skilled in the art and described, for example, in Houben-Weyl, Methoden der Organischen Chemie [Methods of Organic Chemistry], Georg Thieme Verlag Stuttgart, Vol. E 11, additional and supplementary volumes to the fourth edition 1985, p. 174 et seq.

Scheme 4

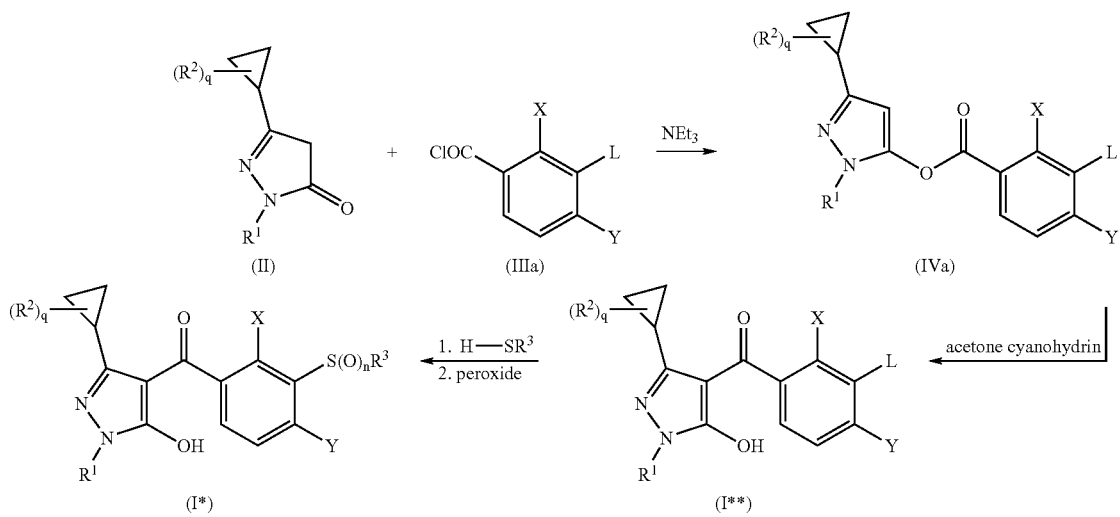

The compounds of the formula (III) mentioned above can be prepared, for example, from the corresponding benzoic acids of the formula (IIIb) by reaction with acid chlorides, such as thionyl chloride, according to methods known to the person skilled in the art.

(IIIb)

Compounds of the formula (IIIb) can be prepared, for example, according to scheme 6: to this end, in a first step, the 3-amino derivative of the formula (IIIc) is diazotized and then converted with potassium ethyl xanthogenate and subsequent hydrolysis into a 3-thio derivative of the formula (IIId). Such reactions are described, for example, in Houben-Weyl, Methoden der Organischen Chemie, Georg Thieme Verlag Stuttgart, Vol. E 9, fourth edition 1955, p. 12 et seq.

In a second step, the 3-thio derivatives of the formula (IIId) can be alkylated with alkylating agents by nucleophilic substitution on a saturated carbon atom or by a conjugated addition to an acceptor-substituted olefin, to give a derivative of the formula (IIIe). Such reactions are described, for example, in Houben-Weyl, Methoden der Organischen Chemie, Georg Thieme Verlag Stuttgart, Vol. E 11, additional and supplementary volumes to the fourth edition 1985, p. 165 ff. Subsequent oxidation of the compounds of the formula (IIIe) gives compounds of the formula (IIIb) in which n is 1 or 2.

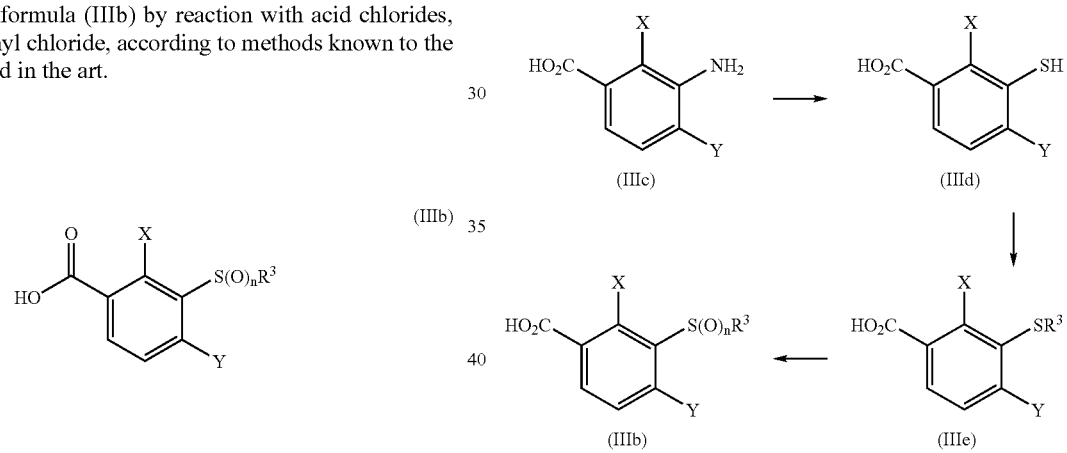

Scheme 6

Compounds of the formulae (III) and (IIIb) in which X, Y and n are as defined for formula (I) are novel and also form part of the subject matter of the present application.

The starting materials used in the above schemes are either commercially available or can be prepared by methods known per se. Thus, the pyrazolones of the formula (II) can be prepared, for example, by the methods described in EP-A 0 240 001 and J. Prakt. Chem. 315, 382, (1973), and the benzoic acids of the formula (III) and the benzoyl chlorides of the formula (IIIa) can be prepared by the methods described in EP-A 0 527 036 and WO 03/014071.

The compounds of the formula (I) according to the invention have an excellent herbicidal activity against a broad range of economically important monocotyledonous and dicotyledonous harmful plants. The active substances control perennial weeds equally well which produce shoots from rhizomes, root stocks or other perennial organs and which cannot be easily controlled. In this context, it generally does not matter whether the substances are applied before sowing, pre-emergence or post-emergence. Some representatives of the monocotyledonous and dicotyledonous weed flora which can be controlled by the compounds according to the invention may be mentioned individually as examples, but this is not to be taken to mean a restriction to certain species. The monocotyledonous weed species which are controlled well are, for example, *Avena, Lolium, Alopecurus, Phalaris, Echinochloa, Digitaria, Setaria* and *Cyperus* species from the annual group, and *Agropyron, Cynodon, Imperata* and *Sorghum* or else perennial *Cyperus* species amongst the perennial species. In the case of dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from the annual group, and *Convolvulus, Cirsium, Rumex* and *Artemisia* among the perennial weeds. Harmful plants which are found under the specific culture conditions of rice, such as, for example, *Echinochloa, Sagittaria, Alisma, Eleocharis, Scirpus* and *Cyperus* are also controlled outstandingly well by the active substances according to the invention. If the compounds according to the invention are applied to the soil surface prior to germination, then either emergence of the weed seedlings is prevented completely, or the weeds grow until they have reached the cotyledon stage but growth then comes to a standstill and, after a period of three to four weeks, the plants eventually die completely. When the active substances are applied post-emergence to the green parts of the plants, growth also stops drastically very soon after the treatment, and the weeds remain at the growth stage of the time of application, or, after a certain period of time, they die completely so that competition by the weeds, which is detrimental for the crop plants, is thus eliminated at a very early stage and in a sustained manner. In particular, the compounds according to the invention have an outstanding action against *Apera spica venti, Chenopodium album, Lamium purpureum, Polygonum convolvulus, Stellaria media, Veronica hederifolia, Veronica persica* and *Viola tricolor.*

Although the compounds according to the invention have an outstanding herbicidal activity against monocotyledonous and dicotyledonous weeds, crop plants of economically important crops such as, for example, wheat, barley, rye, rice, corn, sugar beet, cotton and soybeans, only suffer negligible damage, if any. In particular, they are outstandingly well tolerated in cereals, such as wheat, barley and corn, in particular wheat. This is why the present compounds are highly suitable for the selective control of undesired vegetation in stands of agricultural useful plants or of ornamentals.

Owing to their herbicidal properties, the active substances can also be employed for controlling harmful plants in crops of known plants or genetically modified plants which are yet to be developed. As a rule, the transgenic plants are distinguished by particularly advantageous properties, for example by resistances to certain pesticides, especially certain herbicides, by resistances to plant diseases or causative organisms of plant diseases, such as certain insects or microorganisms such as fungi, bacteria or viruses. Other particular properties concern for example the harvested material with regard to quantity, quality, shelf life, composition and specific constituents. Thus, transgenic plants are known which have an increased starch content or whose starch quality has been modified, or whose fatty acid composition in the harvested material is different.

The compounds of the formula (I) according to the invention or their salts are preferably employed in economically important transgenic crops of useful plants and ornamentals, for example cereals such as wheat, barley, rye, oats, millet, rice, cassava and corn, or else crops of sugar beet, cotton, soybeans, oilseed rape, potato, tomato, pea and other vegetables. The compounds of the formula (I) can preferably be employed as herbicides in crops of useful plants which are resistant, or have been genetically modified to be resistant, to the phytotoxic effects of the herbicides.

Conventional routes for the generation of novel plants which have modified properties compared with existing plants are, for example, traditional breeding methods and the generation of mutants. Alternatively, novel plants with modified properties can be generated with the aid of recombinant methods (see, for example, EP-A-0221044, EP-A-0131624). For example, several cases of the following have been described:

recombinant modifications of crop plants for the purposes of modifying the starch synthesized in the plants (for example WO 92/11376, WO 92/14827, WO 91/19806), transgenic crop plants which exhibit resistances to certain herbicides of the glufosinate type (cf. e.g. EP-A-0242236, EP-A-242246), glyphosate type (WO 92/00377) or of the sulfonylurea type (EP-A-0257993, U.S. Pat. No. 5,013, 659)

transgenic crop plants, for example cotton, with the ability to produce *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology, with the aid of which novel transgenic plants with modified properties can be generated, are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996 or Christou, "Trends in Plant Science" 1 (1996) 423-431.

To carry out such recombinant manipulations, nucleic acid molecules can be introduced into plasmids which permit a mutagenesis or a sequence alteration by recombination of DNA sequences. With the aid of the abovementioned standard methods, it is possible, for example, to carry out base substitutions, to remove part sequences or to add natural or synthetic sequences. The fragments can be provided with adapters or linkers to link the DNA fragments to each other.

Plant cells with a reduced activity of a gene product can be obtained, for example, by expressing at least one corresponding antisense RNA, a sense RNA for achieving a cosuppression effect, or by expressing at least one suitably constructed ribozyme which specifically cleaves transcripts of the abovementioned gene product.

To this end, it is possible, on the one hand, to use DNA molecules which encompass all of the coding sequence of a gene product including any flanking sequences which may be present, but also DNA molecules which only encompass portions of the coding sequence, it being necessary for these portions to be so long as to cause an antisense effect in the cells. Another possibility is the use of DNA sequences which have a high degree of homology with the coding sequences of a gene product, but are not completely identical.

When expressing nucleic acid molecules in plants, the protein synthesized may be localized in any desired compartment of the plant cell. However, to achieve localization in a particular compartment, the coding region can, for example, be linked to DNA sequences which ensure localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give intact plants. In principle, the transgenic plants can be plants of any desired plant species, i.e. both monocotyledonous and dicotyledonous plants. Thus, transgenic plants can be obtained which exhibit modified properties owing to the overexpression, suppression or inhibition of homologous (=natural) genes or gene sequences or expression of heterologous (=foreign) genes or gene sequences.

When using the active substances according to the invention in transgenic crops, effects are frequently observed in addition to the effects against harmful plants to be observed in other crops, which are specific for the application in the transgenic crop in question, for example a modified or specifically widened weed spectrum which can be controlled, modified application rates which may be employed for the application, preferably good combining ability with the herbicides to which the transgenic crop is resistant, and an effect on the growth and yield of the transgenic crop plants. The invention therefore also relates to the use of the compounds according to the invention as herbicides for controlling harmful plants in transgenic crop plants.

The substances according to the invention additionally have outstanding growth-regulatory properties in crop plants. They engage in the plants' metabolism in a regulatory fashion and can thus be employed for the targeted control of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since lodging can be reduced, or prevented completely, hereby.

The compounds according to the invention can be employed in the form of wettable powders, emulsifiable concentrates, sprayable solutions, dusts or granules in the customary preparations. The invention therefore furthermore relates to herbicidal compositions comprising compounds of the formula (I). The compounds of the formula (I) can be formulated in various ways, depending on the prevailing biological and/or chemico-physical parameters. Examples of suitable formulations which are possible are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for spreading and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Wettable powders are preparations which are uniformly dispersible in water and which, in addition to the active substance, also contain ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltaurate, in addition to a diluent or inert substance. To prepare the wettable powders, the herbicidal active substances are ground finely, for example in customary equipment such as hammer mills, blowing mills and air-jet mills, and simultaneously or subsequently mixed with the formulation auxiliaries.

Emulsifiable concentrates are prepared by dissolving the active substance in an organic solvent, e.g. butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which can be used are: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials, for example talc, natural clays such as kaolin, bentonite and pyrophyllite, or diatomaceous earth.

Suspension concentrates can be water-based or oil-based. They can be prepared for example by wet-grinding by means of customary bead mills, if appropriate with addition of surfactants, as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active substance onto adsorptive, granulated inert material or by applying active substance concentrates to the surface of carriers such as sand, kaolinites or granulated inert material with the aid of adhesives, for example polyvinyl alcohol, sodium polyacrylate or else mineral oils. Suitable active substances can also be granulated in the fashion which is conventional for the production of fertilizer granules, if desired as a mixture with fertilizers.

Water-dispersible granules are generally prepared by customary methods such as spray drying, fluidized-bed granulation, disk granulation, mixing with high-speed stirrers and extrusion without solid inert material.

To prepare disk granules, fluidized-bed granules, extruder granules and spray granules, see, for example methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8-57.

For further details on the formulation of crop protection agents see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical preparations comprise 0.1 to 99% by weight, in particular 0.1 to 95% by weight, of active substance of the formula (I). In wettable powders, the active substance concentration is, for example, approximately 10 to 90% by weight, the remainder to 100% by weight being composed of customary formulation constituents. In the case of emulsifiable concentrates, the active substance concentration can amount to approximately 1 to 90, preferably 5 to 80% by weight. Formulations in the form of dusts comprise 1 to 30% by weight of active substance, preferably in most cases 5 to 20% by weight of active substance, and sprayable solutions comprise approximately 0.05 to 80, preferably 2 to 50% by weight of active substance. In the case of water-dispersible granules, the active substance content depends partly on whether the active compound is in liquid or solid form and on the granulation auxiliaries, fillers and the like which are being used. In the case of the water-dispersible granules, for example, the active substance content is between 1 and 95% by weight, preferably between 10 and 80% by weight.

In addition, the active substance formulations mentioned comprise, if appropriate, the tackifiers, wetters, dispersants, emulsifiers, penetrants, preservatives, antifreeze agents, solvents, fillers, carriers, colorants, antifoams, evaporation inhibitors, and pH and viscosity regulators which are conventional in each case.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Active substances which can be employed in combination with the active substances according to the invention in mixed formulations or in the tank mix are, for example, known active substances as are described, for example, in Weed Research 26, 441-445 (1986) or "The Pesticide Manual", 14th edition, The British Crop Protection Council and the Royal Soc. of Chemistry, 2006 and literature cited therein. Known herbicides which must be mentioned, and can be combined with the compounds of the formula (I), are, for example, the following active substances (note: the compounds are either designated by the common name according to the International Organization for Standardization (ISO) or using the chemical name, if appropriate together with a customary code number):

acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluorine-2-phenyl-4H-3,1-benzoxazin-4-one; benazolin; benfluralin; benfuresate; bensulfuron-methyl; bensulide; bentazone; benzofenap; benzofluor; benzoylpropethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butylester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethylester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flucarbazoue; flufenacet; flumetsulam; flumeturon; flumiclorac and its esters (for example pentylester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; foramsulfuron; fosamine; furyloxyfen; glufosinate; glyphosate; halosafen; halosulfuron and its esters (for example methylester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; iodosulfuron-methyl-sodium; isocarbamid; isopropalin; isoproturon; isouron; isoxaben; isoxapyrifop; karbutilate; lactofen; lenacil; linuron; MCPA; MCPB; mecoprop; mefenacet; mefluidid; mesosulfuron; mesotrione; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazi-
namine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendinethalin; perfluidone; phenisopham; phenmedipham; picloram; pinoxaden; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propoxycarbazone; propyzamide; prosulfalin; prosulfocarb; prosulfuron (CGA-152005); prynachlor; pyrazolinate; pyrazon; pyrasulfotole; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy) phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy] propanoic acid and its methyl ester; sulcotrione; sulfentrazon (FMC-97285, F-6285); sulfazuron; sulfometuron-methyl; sulfosate (ICI-A0224); TCA; tebutam (GCP-5544); tebuthiuron; tembotrione; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiencarbazone; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023

For use, the formulations, which are present in commercially available form, are if appropriate diluted in the customary manner, for example using water in the case of wettable powders, emulsifiable concentrates, dispersions and water-dispersible granules. Preparations in the form of dusts, soil granules, granules for spreading and sprayable solutions are usually not diluted any further with other inert substances prior to use.

The application rate required of the compounds of the formula (I) varies with the external conditions such as, inter alia, temperature, humidity and the nature of the herbicide used. It can vary within wide limits, for example between 0.001 and 1.0 kg/ha or more of active substance, but it is preferably between 0.005 and 750 g/ha.

The examples which follow illustrate the invention.

A. CHEMICAL EXAMPLES

Preparation of 3-cyclopropyl-4-(3-cyclopropylmethylthio-2-methyl-4-methylsulfonylbenzoyl)-5-hydroxy-1-methylpyrazole (Example No. 1-38)

Step 1:
3-Mercapto-2-methyl-4-methylsulfonylbenzoic acid 11.0 g (48.0 mmol) of 3-amino-2-methyl-4-methylsulfonylbenzoic acid (synthesis described by T. L. Siddall et al. in Pest Management Science (2002), 58 (12), 1175-1186) was added to a solution of 2.03 g (50.9 mmol) of NaOH in 60 ml of water. 3.31 g (48.0 mmol) of sodium nitrite were then added. At 5-8° C., the solution was added dropwise to a mixture of concentrated HCl and ice. The mixture was stirred at this temperature for 15 minutes and then neutralized with sodium acetate. The content was then added dropwise to a solution, kept at 70-80° C., of 21.54 g (134.3 mmol) of potassium ethyl xanthogenate in 80 ml of water. The mixture was stirred at 80° C. for 15 minutes and then, at RT, acidified for work-up with 1M HCl. After five minutes, the mixture was decanted and 85 ml of 10% strength aqueous sodium hydroxide solution were added to the residue. The mixture was heated and distillate formed was removed with the aid of a distillation assembly, so that an internal temperature of 100° C. could be reached. After the mixture had been heated at this temperature for 1.25 h, HPLC analysis showed that the reaction had gone to completion. 21 ml of a saturated aqueous sodium bisulfite solution were then added, and the mixture was heated at 100° C. for 10 minutes. For work-up, the cooled reaction mixture was acidified with 1M HCl, cooled to 0-5° C. and filtered under an atmosphere of nitrogen. What was isolated were 10 g of a solid; a 1H-NMR spectrum showed the identity of the product.

Step 2: 3-Cyclopropylmethylthio-2-methyl-4-methylsulfonylbenzoic acid

Under an atmosphere of nitrogen, 9.0 g (36.5 mmol) of 3-mercapto-2,4-dimethyl-sulfonylbenzoic acid were dissolved in 70 ml of N,N-dimethylformamide (DMF), and 3.07 g (76.7 mmol, purity 60% by weight) of NaH were then added a little at a time. The mixture was stirred at RT for 15 minutes, and 5.43 g (40.2 mmol) of cyclopropylmethyl bromide were then slowly added dropwise. The mixture was stirred at RT for 16 h. For work-up, the solvent was removed under reduced pressure and the residue was taken up in a mixture of water and methanol. 8 g (200 mmol) of NaOH were added, and the reaction mixture was stirred at RT until HPLC analysis showed no more cyclopropylmethyl ester. The mixture was freed from the solvents, water was added to the residue and the aqueous phase was acidified with 1M HCl and then extracted twice with ethyl acetate (EA). The combined organic phases were dried, filtered and freed from the solvent. The residue was washed with n-heptane. The heptane was decanted and the residue was dried under reduced pressure. What was isolated were 11.1 g of the pure product.

Step 3: 3-Cyclopropyl-4-(3-cyclopropylmethylthio-2-methyl-4-methylsulfonylbenzoyl)-5-hydroxy-1-methylpyrazole 190 mg (0.63 mmol) of 3-cyclopropylmethylthio-2-methyl-4-methylsulfonylbenzoic acid were initially charged in 15 ml of dry dichloromethane, and 121 mg (0.95 mmol) of oxalyl chloride and a few drops of DMF were added. The mixture was heated at reflux for 15 min, after which no more evolution of gas could be observed. The content was cooled to RT and concentrated. The acid chloride obtained in this manner was dissolved in 15 ml of acetonitrile, and 96 mg (0.70 mmol) of 3-cyclopropyl-5-hydroxy-1-methylpyrazole were added. 128 mg (1.27 mmol) of triethylamine were then slowly added dropwise, and the reaction mixture was stirred at RT for 16 h. Ten drops of acetone cyanohydrin and a spatula tip of KCN were added to the enol ester obtained in this manner. The mixture was stirred at RT for 16 h and then concentrated. 15 ml of dichloromethane and then 2 ml of 1M HCl were added to the residue. After phase separation, the organic phase was freed from the solvent. The residue was purified chromatographically, and 65.7 mg of pure product were isolated.

Preparation of 3-cyclopropyl-4-(3-cyclopropylmethylsulfonyl-2-methyl-4-methylsulfonylbenzoyl)-5-hydroxy-1-methylpyrazole (Example No. 1-50)

Step 1: 3-Cyclopropylmethylsulfonyl-2-methyl-4-methylsulfonylbenzoic acid 952 mg (3.17 mmol) of 3-cyclopropylmethylthio-2-methyl-4-methylsulfonylbenzoic acid were dissolved in 15 ml of glacial acetic acid. 31 mg (0.095 mmol) of sodium tungstate (VI) dihydrate were added, and the mixture was then heated to 60° C. At this temperature, 1.44 g (30% strength, 12.7 mmol) of an aqueous hydrogen peroxide solution were carefully added dropwise. The mixture was stirred at this temperature for two days. The mixture was then cooled and, for work-up, poured into water. The mixture was extracted twice with EA, the combined organic phases were washed with an aqueous, saturated sodium bisulfite solution, and, after analytical confirmation of the absence of peroxides, the mixture was dried, filtered and freed under reduced pressure from the solvents. 744 g of the product were isolated.

Step 2: Synthesis of 3-cyclopropyl-4-(3-cyclopropyl-methylsulfonyl-2-methyl-4-methylsulfonylbenzoyl)-5-hydroxy-1-methylpyrazole 149 mg (0.45 mmol) of 3-cyclopropylmethylsulfonyl-2-methyl-4-methylsulfonyl-benzoic acid were initially charged in 15 ml of dry $CH_2Cl_2$, and 114 mg (0.90 mmol) of oxalyl chloride and a few drops of DMF were added. The mixture was heated at reflux for 15 min, after which no more evolution of gas could be observed. The content was cooled to RT and concentrated. The acid chloride obtained in this manner was dissolved in 15 ml of dry dichloromethane, and 68 mg (0.49 mmol) of 3-cyclopropyl-5-hydroxy-1-methylpyrazole were added. 91 mg (0.90 mmol) of triethylamine were then slowly added dropwise, and the reaction mixture was stirred at RT for 16 h. For work-up, 2 ml of 1M HCl were added, and after phase separation the organic phase was freed from the solvent. The enol ester obtained in this manner was taken up in 15 ml of acetonitrile, and 10 drops of acetone cyanohydrin and a spatula tip of KCN were added. The mixture was stirred at RT for 16 h and then concentrated. 15 ml of $CH_2Cl_2$ and then 2 ml of 1M HCl were added. After phase separation, the organic phase was freed from the solvent. The residue was purified chromatographically, and 103 mg of pure product were isolated.

Preparation of 4-(2-chloro-3-(2-methoxyethyl)thio-4-methylsulfonylbenzoyl)-3-cyclopropyl-5-hydroxy-1-methylpyrazole (Example No. 1-3)

Step 1: Synthesis of 2-chloro-3-(2'-methoxyethyl)thio-4-methylsulfonylbenzoic acid 5.0 g (19.8 mmol) of 2-chloro-3-fluoro-4-methylsulfonyl-benzoic acid (synthesis described in WO 98/42648) were taken up in 40 ml of DMF. 871 mg (21.8 mmol, purity 60% by weight) of NaH were added. The mixture was stirred at RT for 30 minutes. A reaction mixture containing the sodium salt of 2-methoxyethanethiol (prepared from a solution of 2.19 g (23.7 mmol) of 2-methoxyethanethiol in 10 ml of DMF which had been added dropwise to a suspension of 950 mg (23.7 mmol, purity 60% by weight) of NaH in 30 ml of DMF, followed by stirring at RT for 30 minutes) was then added a little at a time. During the addition, the temperature was kept below 30° C. The reaction mixture was stirred at RT for 16 h, for work-up diluted with water and washed with diethyl ether. The aqueous phase was acidified with 1M HCl and extracted with tert-butyl methyl ether. The organic phase was dried and filtered. The aqueous phase was additionally extracted with EA, and the organic phase was also dried and filtered. The filtrates of the organic phases were combined and freed from the solvent. The residue was dried under reduced pressure and purified chromatographically. This gave 4.8 g of the pure product.

Step 2: Synthesis of 4-(2-chloro-3-(2-methoxyethyl)thio-4-methylsulfonylbenzoyl)-3-cyclopropyl-5-hydroxy-1-methylpyrazole 550 mg (1.69 mmol) of 2-chloro-3-(2-methoxyethyl)thio-4-methylsulfonylbenzoic acid were initially charged in 20 ml of dry $CH_2Cl_2$, and 430 mg (3.39 mmol) of oxalyl chloride and two drops of DMF were added. The mixture was heated at reflux for 15 minutes. The content was cooled to RT and concentrated. The acid chloride obtained in this manner was dissolved in 20 ml of dry $CH_2Cl_2$, and 257 mg (1.86 mmol) of 3-cyclopropyl-5-hydroxy-1-methylpyrazole were added. 343 mg (3.39 mmol) of triethylamine were then slowly added dropwise, and the reaction mixture was stirred at RT for 16 h. For work-up, 5 ml of 1M HCl were added, and, after phase separation, the organic phase was freed from the solvent. The residue was purified chromatographically, and the enol ester obtained in this manner was taken up in 20 ml of acetonitrile, and 343 mg (3.39 mmol) of triethylamine, eight drops of acetone cyanohydrin and a spatula tip of KCN were added. The mixture was stirred at RT for 16 h and then concentrated. 20 ml of $CH_2Cl_2$ and then 5 ml of 1M HCl were added to the residue. After phase separation, the organic phase was freed from the solvent. The residue was purified chromatographically, and 579 mg of pure product were isolated.

Preparation of 4-(2-chloro-3-(2-methoxyethyl)sulfynyl-4-methylsulfonylbenzoyl)-3-cyclopropyl-5-hydroxy-1-methylpyrazole (Example No. 1-9) and 4-(2-chloro-3-(2-methoxyethyl)sulfonyl-4-methylsulfonylbenzoyl)-3-cyclopropyl-5-hydroxy-1-methyl pyrazole (Example No. 1-15)

193 mg (0.43 mmol) of 4-(2-chloro-3-(2-methoxyethyl)thio-4-methylsulfonylbenzoyl)-3-cyclopropyl-5-hydroxy-1-methylpyrazole were dissolved in 20 ml of $CH_2Cl_2$, and 321 mg (purity 70% by weight, 1.30 mmol) of meta-chloroperbenzoic acid were then added. The mixture was then stirred at RT for 16 h. For work-up, the mixture was diluted with $CH_2Cl_2$ and washed with 10% strength aqueous sodium bisulfite solution. During this step, the pH of the aqueous phase was kept in the acidic range using 1M HCl. After phase separation and the analytical confirmation of the absence of peroxides, the organic phase was then dried, filtered and freed from solvent. The residue was separated chromatographically, which gave 9.6 mg of pure 4-(2-chloro-3-(2-methoxyethyl)sulfynyl-4-methylsulfonylbenzoyl)-3-cyclopropyl-5-hydroxy-1-methylpyrazole and 71.6 mg of pure 4-(2-chloro-3-(2-methoxyethyl)sulfonyl-4-methylsulfonylbenzoyl)-3-cyclopropyl-5-hydroxy-1-methylpyrazole.

Preparation of 3-cyclopropyl-5-hydroxy-4-(3-(2-methoxyethyl)thio-2-methyl-4-trifluoromethylbenzoyl)-1-methylpyrazole (Example No. 1-2091)

Step 1: Synthesis of 3-fluoro-2-methyl-4-trifluoromethylbenzoic acid 25.0 g (120.1 mmol) of 3-fluoro-4-trifluoromethylbenzoic acid were dissolved in 250 ml of dry THF, and 100.9 ml (2.5M in hexane, 252.3 mmol) of n-butyllithium were added dropwise at a temperature of −40° C. The mixture was stirred for 3.5 h, and a solution of 51.2 g (360.4 mmol) of iodomethane in 50 ml of dry THF was then added. The mixture was stirred for 16 h, and after half an hour the temperature slowly increased to RT. For work-up, 150 ml of 1M HCl were added carefully. The mixture was extracted with diethyl ether, and the organic phase was then extracted with 1M NaOH. The aqueous phase was acidified and then extracted with diethyl ether. The organic phase was washed with water, dried and concentrated. The residue was triturated with n-heptane, and the solid was collected by filtration. What was isolated were 13.5 g of the pure product.

Step 2: Synthesis of 3-(2-methoxyethyl)thio-2-methyl-4-trifluoromethylbenzoic acid 1.45 g (6.53 mmol) of 3-fluoro-2-methyl-4-trifluoromethylbenzoic acid were initially charged in 40 ml of DMF. 809 mg (20.2 mmol) of NaH were added a little at a time. After the evolution of gas had ceased, 1.20 g (13.1 mmol) of 2-methoxyethanethiol were added a little at a time. The mixture was stirred at RT for 10 minutes and then heated at 80° C. for 15 h. The reaction mixture was cooled and concentrated under reduced pressure, and for work-up water was added and the mixture was acidified with 1M HCl. The product precipitated and was removed by filtration. The product was then washed with water and n-heptane. What was isolated were 1.7 g of the pure product.

Step 3: Synthesis of 3-cyclopropyl-5-hydroxy-4-(3-(2-methoxyethyl)thio-2-methyl-4-trifluoromethylbenzoyl)-1-methylpyrazole 520 mg (1.77 mmol) of 3-(2-methoxyethyl)thio-2-methyl-4-trifluoromethylbenzoic acid were initially charged in 20 ml of dry $CH_2Cl_2$, and 449 mg (3.53 mmol) of oxalyl chloride and two drops of DMF were added. The mixture was heated at reflux for 15 min, after which no more evolution of gas could be observed. The content was cooled to RT and concentrated. The acid chloride obtained in this manner was dissolved in 20 ml of dry $CH_2Cl_2$, and 269 mg (1.94 mmol) of 3-cyclopropyl-5-hydroxy-1-methylpyrazole were added. 358 mg (3.53 mmol) of triethylamine were then slowly added dropwise, and the reaction mixture was stirred at RT for 16 h. For work-up, 5 ml of 1M HCl were added, and, after phase separation, the solvent was removed. The enol ester obtained in this manner was, after chromatographic purification, taken up in 20 ml of acetonitrile, and 358 mg (3.53 mmol) of triethylamine were added. Eight drops of acetone cyanohydrin and a spatula tip of KCN were then added. The mixture was stirred at RT for 16 h and then concentrated. 20 ml of $CH_2Cl_2$ and then 5 ml of 1M HCl were added to the residue. After phase separation, the mixture was freed from the solvent. The residue was purified chromatographically, and 354 mg of pure product were isolated.

Preparation of 4-(4-chloro-3'-cyclopropylmethylthio-2-methylbenzoyl)-3-cyclopropyl-5-hydroxy-1-methylpyrazole (Example No. 1-1406)

Step 1: Synthesis of methyl 4-chloro-3-(dimethylaminothiocarbonyloxy)-2-methylbenzoate Under an atmosphere of nitrogen, 12.3 g (109.7 mmol) of 1,4-diazabicyclo[2.2.2]-octane and then 13.6 g (109.7 mmol) of dimethylaminothiocarbonyl chloride were added to 11.0 g (54.8 mmol) of methyl 4-chloro-3-hydroxy-2-methylbenzoate (synthesis described in DE 10039723) in 200 ml of DMF. The mixture was stirred at RT for 16 h and, for work-up, poured into ice-water. The product precipitated and was removed by filtration. The residue was washed with 1M HCl. This gave 14.7 g of pure product.

Step 2: Synthesis of methyl 4-chloro-3-(dimethylaminocarbonylthio)-2-methyl-benzoate Under an atmosphere of nitrogen, 12.1 g (42.0 mmol) of methyl 4-chloro-3-(dimethylaminothiocarbonyloxy)-2-methylbenzoate in 30 ml of 1,3-dimethoxy-benzene were heated at 220° C. for 6 h. For work-up, the reaction mixture was cooled and concentrated under reduced pressure. After chromatographic purification of the residue, 5.2 g of pure product were isolated.

Step 3: Synthesis of 4-chloro-3-mercapto-2-methylbenzoic acid 6.61 g (purity 85% by weight, 100.1 mmol) of KOH were added to 4.80 g (16.7 mmol) of methyl 4-chloro-3-(dimethylaminocarbonylthio)-2-methylbenzoate in 150 ml of methanol, and the mixture was stirred under reflux for two days. The reaction mixture was freed from solvent, water was added to the residue, which was then acidified with 1M HCl, and the solid was collected by filtration. This gave 3.2 g of pure product.

Step 4: Synthesis of methyl 4-chloro-3-mercapto-2-methylbenzoate

Under an atmosphere of nitrogen, 3.60 g (17.8 mmol) of 4-chloro-3-mercapto-2-methylbenzoic acid in 50 ml of absolute methanol and 1 ml of concentrated sulfuric acid were heated under reflux for 17 h. The mixture was freed from solvent, and the residue was taken up in water. After two extractions with ethyl acetate, the combined organic phases were dried, filtered under an atmosphere of nitrogen and freed from the solvent. What was isolated were 3.2 g of pure product.

Step 5: Synthesis of methyl 4-chloro-3-cyclopropylmethylthio-2-methylbenzoate 1.66 g (5.09 mmol) of cesium carbonate in 20 ml of acetonitrile were added to 1.05 g (4.85 mmol) of methyl 4-chloro-3-mercapto-2-methylbenzoate. 687 mg (5.09 mmol) of cyclopropylmethyl bromide were slowly added dropwise, and the reaction mixture was stirred at RT for 16 h. For work-up, the solvent was removed, and water was added to the residue. The mixture was extracted three times with ethyl acetate, the combined organic phases were dried and filtered and the solvent was removed. What was isolated were 1.2 g of pure product.

Step 6: Synthesis of 4-chloro-3-cyclopropylmethylthio-2-methylbenzoic acid 3 ml of 20% strength aqueous sodium hydroxide solution were added to 1.20 g (4.43 mmol) of methyl 4-chloro-3-cyclopropylmethylthio-2-methylbenzoate in 30 ml of methanol, and the mixture was stirred at RT for 16 h. For work-up, the mixture was concentrated on a rotary evaporator, and the residue was taken up in water. The mixture was acidified with 1M HCl, and the product was then filtered off as a solid. This gave 1.1 g of pure product.

Step 7: Synthesis of 4-(4'-chloro-3'-cyclopropylmethylthio-2'-methylbenzoyl)-3-cyclopropyl-5-hydroxy-1-methylpyrazole 161 mg (1.17 mmol) of 3-cyclopropyl-5-hydroxy-1-methylpyrazole and a few drops of N,N-dimethylaminopyridine were added to 272 mg (1.06 mmol) of 4-chloro-3-cyclopropylmethylthio-2-methylbenzoic acid. 244 mg (1.27 mmol) of 1-(3-dimethylaminopropyl)-3-ethylcarbodiimide hydrochloride were added, and the mixture was stirred at RT for 16 h. For work-up, 3 ml of 1M HCl were added, and the organic phase was freed from the solvent. 214 mg (2.12 mmol) of triethylamine, 10 drops of acetone cyanohydrin and a spatula tip of KCN were added to the residue in 15 ml of acetonitrile. This reaction mixture was stirred at RT for 16 h and then freed from the solvent. 2 ml of 1M HCl were added to the residue in 15 ml of $CH_2Cl_2$. The organic phase was freed from the solvent, and the residue was then purified chromatographically. This gave 154 mg of pure product.

Preparation of 4-(4-chloro-3-cyclopropylmethylsulfonyl-2-methylbenzoyl)-3-cyclo-propyl-5-hydroxy-1-methylpyrazole (Example No. 1-1418)

128 mg (purity 70% by weight, 0.52 mmol) of meta-chloroperbenzoic acid were added to 78 mg (0.21 mmol) of 4-(4-chloro-3-cyclopropylmethylthio-2-methylbenzoyl)-3-cyclopropyl-5-hydroxy-1-methylpyrazole in 20 ml of $CH_2Cl_2$. This mixture was then stirred at RT for 5 h. For work-up, the mixture was washed with 10% strength aqueous sodium bisulfite solution. During this step, the pH of the aqueous phase was kept in the acidic range, otherwise the mixture was acidified with 1M HCl. Subsequently, after phase separation and after analytical confirmation of the absence of peroxides, the organic phase was dried, filtered and freed from the solvent. The residue was purified chromatographically, which gave 29.1 mg of pure product.

The examples given in the tables which follow were prepared analogously to the methods mentioned above, or can be obtained analogously to the methods mentioned above. These compounds are very particularly preferred.

The Abbreviations Used Denote:

Bu=Butyl Et=Ethyl Me=Methyl Pr=Propyl c=cyclo i=iso Ph=Phenyl

TABLE A

Compounds according to the invention of the general formula (I) in which $R^1$ is methyl, $R^4$ is hydrogen and q is zero

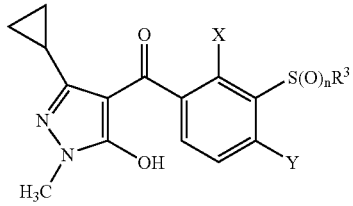

| No. | X | $R^3$ | n | Y | Physical data: $^1$H-NMR: δ[CDCl$_3$] |
|---|---|---|---|---|---|
| 1-1 | Cl | c-Pr | 0 | SO$_2$Me | |
| 1-2 | Cl | CH$_2$-c-Pr | 0 | SO$_2$Me | |
| 1-3 | Cl | (CH$_2$)$_2$OMe | 0 | SO$_2$Me | 8.23 (d, 1H), 7.51 (d, 1H), 3.64 (t, 2H), 3.62 (s, 3H), 3.49 (s, 3H), 3.29 (s, 3H), 3.24 (t, 2H), 0.91 (m, 1H), 0.76 (m, 2H), 0.44 (m, 2H) |
| 1-4 | Cl | (CH$_2$)$_3$OMe | 0 | SO$_2$Me | |
| 1-5 | Cl | (CH$_2$)$_2$OEt | 0 | SO$_2$Me | |
| 1-6 | Cl | (CH$_2$)$_2$OCH$_2$-c-Pr | 0 | SO$_2$Me | |
| 1-7 | Cl | c-Pr | 1 | SO$_2$Me | |
| 1-8 | Cl | CH$_2$-c-Pr | 1 | SO$_2$Me | |
| 1-9 | Cl | (CH$_2$)$_2$OMe | 1 | SO$_2$Me | 8.22 (d, 1H), 7.62 (d, 1H), 4.09-4.01 (m, 2H), 3.91-3.85 (m, 1H), 3.62 (s, 3H), 3.50-3.42 (m, 7H), 0.92 (m, 1H), 0.78 (m, 2H), 0.47 (m, 2H) |
| 1-10 | Cl | (CH$_2$)$_3$OMe | 1 | SO$_2$Me | |
| 1-11 | Cl | (CH$_2$)$_2$OEt | 1 | SO$_2$Me | |
| 1-12 | Cl | (CH$_2$)$_2$OCH$_2$-c-Pr | 1 | SO$_2$Me | |
| 1-13 | Cl | c-Pr | 2 | SO$_2$Me | |
| 1-14 | Cl | CH$_2$-c-Pr | 2 | SO$_2$Me | |
| 1-15 | Cl | (CH$_2$)$_2$OMe | 2 | SO$_2$Me | 8.43 (d, 1H), 7.72 (d, 1H), 4.02 (t, 2H), 3.92 (t, 2H), 3.62 (ss, 6H), 3.29 (s, 3H), 0.92 (m, 1H), 0.78 (m, 2H), 0.65-0.42 (m, 2H) |
| 1-16 | Cl | (CH$_2$)$_3$OMe | 2 | SO$_2$Me | |
| 1-17 | Cl | (CH$_2$)$_2$OEt | 2 | SO$_2$Me | |
| 1-18 | Cl | (CH$_2$)$_2$OCH$_2$-c-Pr | 2 | SO$_2$Me | |
| 1-19 | Br | c-Pr | 0 | SO$_2$Me | |
| 1-20 | Br | CH$_2$-c-Pr | 0 | SO$_2$Me | |
| 1-21 | Br | (CH$_2$)$_2$OMe | 0 | SO$_2$Me | |
| 1-22 | Br | (CH$_2$)$_3$OMe | 0 | SO$_2$Me | |
| 1-23 | Br | (CH$_2$)$_2$OEt | 0 | SO$_2$Me | |
| 1-24 | Br | (CH$_2$)$_2$OCH$_2$-c-Pr | 0 | SO$_2$Me | |
| 1-25 | Br | c-Pr | 1 | SO$_2$Me | |
| 1-26 | Br | CH$_2$-c-Pr | 1 | SO$_2$Me | |

TABLE A-continued

Compounds according to the invention of the general formula (I) in which $R^1$ is methyl, $R^4$ is hydrogen and q is zero

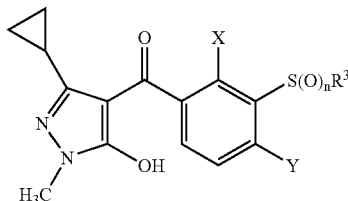

| No. | X | $R^3$ | n | Y | Physical data: $^1$H-NMR: δ[CDCl$_3$] |
|---|---|---|---|---|---|
| 1-27 | Br | (CH$_2$)$_2$OMe | 1 | SO$_2$Me | |
| 1-28 | Br | (CH$_2$)$_3$OMe | 1 | SO$_2$Me | |
| 1-29 | Br | (CH$_2$)$_2$OEt | 1 | SO$_2$Me | |
| 1-30 | Br | (CH$_2$)$_2$OCH$_2$-c-Pr | 1 | SO$_2$Me | |
| 1-31 | Br | c-Pr | 2 | SO$_2$Me | |
| 1-32 | Br | CH$_2$-c-Pr | 2 | SO$_2$Me | |
| 1-33 | Br | (CH$_2$)$_2$OMe | 2 | SO$_2$Me | |
| 1-34 | Br | (CH$_2$)$_3$OMe | 2 | SO$_2$Me | |
| 1-35 | Br | (CH$_2$)$_2$OEt | 2 | SO$_2$Me | |
| 1-36 | Br | (CH$_2$)$_2$OCH$_2$-c-Pr | 2 | SO$_2$Me | |
| 1-37 | Me | c-Pr | 0 | SO$_2$Me | |
| 1-38 | Me | CH$_2$-c-Pr | 0 | SO$_2$Me | 8.17 (d, 1H), 7.47 (d, 1H), 3.62 (s, 3H), 3.48 (s, 3H), 2.83 (d, 2H), 2.67 (s, 3H), 1.02 (m, 1H), 0.90-0.82 (m, 1H), 0.77 (m, 2H), 0.57 (m, 2H), 0.48 (m, 2H), 0.23 (m, 2H) |
| 1-39 | Me | (CH$_2$)$_2$OMe | 0 | SO$_2$Me | 8.19 (d, 1H), 7.48 (d, 1H), 3.63-3.60 (s + t, 5H), 3.47 (s, 3H), 3.34 (s, 3H), 3.12 (t, 2H), 2.63 (s, 3H), 0.91-0.84 (m, 1H), 0.76 (m, 2H), 0.48 (m, 2H) |
| 1-40 | Me | (CH$_2$)$_3$OMe | 0 | SO$_2$Me | 8.17 (d, 1H), 7.47 (d, 1H), 3.61 (s, 3H), 3.47 (t, 2H), 3.46 (s, 3H), 3.32 (s, 3H), 2.96 (t, 2H), 2.64 (s, 3H), 1.92 (quint., 2H), 0.89-0.82 (m, 1H), 0.77 (m, 2H), 0.47 (m, 2H) |
| 1-41 | Me | (CH$_2$)$_2$OEt | 0 | SO$_2$Me | 8.18 (d, 1H), 7.48 (d, 1H), 3.62 (t, 2H), 3.61 (s, 3H), 3.48 (s, 3H), 3.47 (q, 2H), 3.10 (t, 2H), 2.65 (s, 3H), 1.18 (t, 3H), 0.86 (m, 1H), 0.77 (m, 2H), 0.48 (m, 2H) |
| 1-42 | Me | (CH$_2$)$_3$OMe | 0 | SO$_2$Me | |
| 1-43 | Me | c-Pr | 1 | SO$_2$Me | |
| 1-44 | Me | CH$_2$-c-Pr | 1 | SO$_2$Me | |
| 1-45 | Me | (CH$_2$)$_2$OMe | 1 | SO$_2$Me | 8.10 (d, 1H), 7.59 (d, 1H), 4.04-4.00 (m, 1H), 3.91-3.86 (m, 1H), 3.75-3.45 (m, 2H), 3.61 (s, 3H), 3.43 (s, 3H), 3.38 (s, 3H), 2.78 (s, 3H), 0.90-0.71 (m, 3H), 0.56 (m, 1H), 0.43 (m, 1H), |
| 1-46 | Me | (CH$_2$)$_3$OMe | 1 | SO$_2$Me | 8.08 (d, 1H), 7.57 (d, 1H), 3.62-3.56 (m, 6H), 3.38-3.25 (m, 1H), 3.37 (s, 3H), 3.35 (s, 3H), 2.81 (s, 3H), 2.28-2.16 (m, 2H), 0.90-0.72 (m, 3H), 0.55 (m, 1H), 0.45 (m, 1H) |
| 1-47 | Me | (CH$_2$)$_2$OEt | 1 | SO$_2$Me | 8.11 (d, 1H), 7.57 (d, 1H), 4.02 (m, 1H), 3.92 (m, 1H), 3.66-3.53 (m, 4H), 3.60 (s, 3H), 3.38 (s, 3H), 2.78 (s, 3H), 1.22 (t, 3H), 0.90-0.72 (m, 3H), 0.55 (m, 1H), 0.45 (m, 1H) |

TABLE A-continued

Compounds according to the invention of the general formula (I) in which $R^1$ is methyl, $R^4$ is hydrogen and q is zero

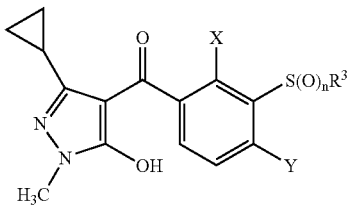

| No. | X | $R^3$ | n | Y | Physical data: $^1$H-NMR: δ[CDCl$_3$] |
|---|---|---|---|---|---|
| 1-48 | Me | (CH$_2$)$_2$OCH$_2$-c-Pr | 1 | SO$_2$Me | |
| 1-49 | Me | c-Pr | 2 | SO$_2$Me | |
| 1-50 | Me | CH$_2$-c-Pr | 2 | SO$_2$Me | 8.37 (d, 1H), 7.67 (d, 1H), 3.65-3.61 (s + d, 5H), 3.57 (s, 3H), 2.80 (s, 3H), 1.30 (m, 1H), 0.88-0.70 (m, 5H), 0.52 (m, 2H), 0.42 (m, 2H) |
| 1-51 | Me | (CH$_2$)$_2$OMe | 2 | SO$_2$Me | 8.37 (d, 1H), 7.66 (d, 1H), 4.06-3.90 (m, 4H), 3.62 (s, 3H), 3.56 (s, 3H), 3.33 (s, 3H), 2.74 (s, 3H), 0.89-0.80 (m, 1H), 0.76 (m, 2H), 0.52 (m, 2H) |
| 1-52 | Me | (CH$_2$)$_3$OMe | 2 | SO$_2$Me | 8.37 (d, 1H), 7.67 (d, 1H), 3.71 (t, 2H), 3.61 (s, 3H), 3.57 (s + t, 5H), 3.33 (s, 3H), 2.73 (s, 3H), 2.27 (quint., 2H), 0.86-0.76 (m, 3H), 0.55-0.50 (m, 2H) |
| 1-53 | Me | (CH$_2$)$_2$OEt | 2 | SO$_2$Me | 8.36 (d, 1H), 7.67 (d, 1H), 4.02 (t, 2H), 3.92 (t, 2H), 3.61 (s, 3H), 3.56 (s, 3H), 3.50 (q, 2H), 2.76 (s, 3H), 1.10 (t, 3H), 0.85-0.75 (m, 3H), 0.52 (m, 2H) |
| 1-54 | Me | (CH$_2$)$_2$OCH$_2$-c-Pr | 2 | SO$_2$Me | |
| 1-55 | Et | c-Pr | 0 | SO$_2$Me | |
| 1-56 | Et | CH$_2$-c-Pr | 0 | SO$_2$Me | |
| 1-57 | Et | (CH$_2$)$_2$OMe | 0 | SO$_2$Me | |
| 1-58 | Et | (CH$_2$)$_3$OMe | 0 | SO$_2$Me | |
| 1-59 | Et | (CH$_2$)$_2$OEt | 0 | SO$_2$Me | |
| 1-60 | Et | (CH$_2$)$_2$OCH$_2$-c-Pr | 0 | SO$_2$Me | |
| 1-61 | Et | c-Pr | 1 | SO$_2$Me | |
| 1-62 | Et | CH$_2$-c-Pr | 1 | SO$_2$Me | |
| 1-63 | Et | (CH$_2$)$_2$OMe | 1 | SO$_2$Me | |
| 1-64 | Et | (CH$_2$)$_3$OMe | 1 | SO$_2$Me | |
| 1-65 | Et | (CH$_2$)$_2$OEt | 1 | SO$_2$Me | |
| 1-66 | Et | (CH$_2$)$_2$OCH$_2$-c-Pr | 1 | SO$_2$Me | |
| 1-67 | Et | c-Pr | 2 | SO$_2$Me | |
| 1-68 | Et | CH$_2$-c-Pr | 2 | SO$_2$Me | |
| 1-69 | Et | (CH$_2$)$_2$OMe | 2 | SO$_2$Me | |
| 1-70 | Et | (CH$_2$)$_3$OMe | 2 | SO$_2$Me | |
| 1-71 | Et | (CH$_2$)$_2$OEt | 2 | SO$_2$Me | |
| 1-72 | Et | (CH$_2$)$_2$OCH$_2$-c-Pr | 2 | SO$_2$Me | |
| 1-73 | CF$_3$ | c-Pr | 0 | SO$_2$Me | |
| 1-74 | CF$_3$ | CH$_2$-c-Pr | 0 | SO$_2$Me | |
| 1-75 | CF$_3$ | (CH$_2$)$_2$OMe | 0 | SO$_2$Me | |
| 1-76 | CF$_3$ | (CH$_2$)$_3$OMe | 0 | SO$_2$Me | |
| 1-77 | CF$_3$ | (CH$_2$)$_2$OEt | 0 | SO$_2$Me | |
| 1-78 | CF$_3$ | (CH$_2$)$_2$OCH$_2$-c-Pr | 0 | SO$_2$Me | |
| 1-79 | CF$_3$ | c-Pr | 1 | SO$_2$Me | |
| 1-80 | CF$_3$ | CH$_2$-c-Pr | 1 | SO$_2$Me | |
| 1-81 | CF$_3$ | (CH$_2$)$_2$OMe | 1 | SO$_2$Me | |
| 1-82 | CF$_3$ | (CH$_2$)$_3$OMe | 1 | SO$_2$Me | |
| 1-83 | CF$_3$ | (CH$_2$)$_2$OEt | 1 | SO$_2$Me | |
| 1-84 | CF$_3$ | (CH$_2$)$_2$OCH$_2$-c-Pr | 1 | SO$_2$Me | |
| 1-85 | CF$_3$ | c-Pr | 2 | SO$_2$Me | |
| 1-86 | CF$_3$ | CH$_2$-c-Pr | 2 | SO$_2$Me | |
| 1-87 | CF$_3$ | (CH$_2$)$_2$OMe | 2 | SO$_2$Me | |
| 1-88 | CF$_3$ | (CH$_2$)$_3$OMe | 2 | SO$_2$Me | |
| 1-89 | CF$_3$ | (CH$_2$)$_2$OEt | 2 | SO$_2$Me | |
| 1-90 | CF$_3$ | (CH$_2$)$_2$OCH$_2$-c-Pr | 2 | SO$_2$Me | |
| 1-91 | OMe | c-Pr | 0 | SO$_2$Me | |

TABLE A-continued

Compounds according to the invention of the general formula (I) in which $R^1$ is methyl, $R^4$ is hydrogen and q is zero

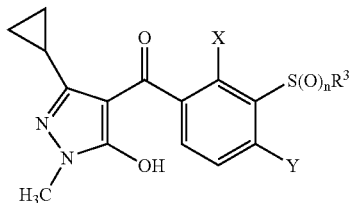

| No. | X | $R^3$ | n | Y | Physical data: $^1$H-NMR: δ[CDCl$_3$] |
|---|---|---|---|---|---|
| 1-92 | OMe | CH$_2$-c-Pr | 0 | SO$_2$Me | |
| 1-93 | OMe | (CH$_2$)$_2$OMe | 0 | SO$_2$Me | |
| 1-94 | OMe | (CH$_2$)$_3$OMe | 0 | SO$_2$Me | |
| 1-95 | OMe | (CH$_2$)$_2$OEt | 0 | SO$_2$Me | |
| 1-96 | OMe | (CH$_2$)$_2$OCH$_2$-c-Pr | 0 | SO$_2$Me | |
| 1-97 | OMe | c-Pr | 1 | SO$_2$Me | |
| 1-98 | OMe | CH$_2$-c-Pr | 1 | SO$_2$Me | |
| 1-99 | OMe | (CH$_2$)$_2$OMe | 1 | SO$_2$Me | |
| 1-100 | OMe | (CH$_2$)$_3$OMe | 1 | SO$_2$Me | |
| 1-101 | OMe | (CH$_2$)$_2$OEt | 1 | SO$_2$Me | |
| 1-102 | OMe | (CH$_2$)$_2$OCH$_2$-c-Pr | 1 | SO$_2$Me | |
| 1-103 | OMe | c-Pr | 2 | SO$_2$Me | |
| 1-104 | OMe | CH$_2$-c-Pr | 2 | SO$_2$Me | |
| 1-105 | OMe | (CH$_2$)$_2$OMe | 2 | SO$_2$Me | |
| 1-106 | OMe | (CH$_2$)$_3$OMe | 2 | SO$_2$Me | |
| 1-107 | OMe | (CH$_2$)$_2$OEt | 2 | SO$_2$Me | |
| 1-108 | OMe | (CH$_2$)$_2$OCH$_2$-c-Pr | 2 | SO$_2$Me | |
| 1-109 | OEt | c-Pr | 0 | SO$_2$Me | |
| 1-110 | OEt | CH$_2$-c-Pr | 0 | SO$_2$Me | |
| 1-111 | OEt | (CH$_2$)$_2$OMe | 0 | SO$_2$Me | |
| 1-112 | OEt | (CH$_2$)$_3$OMe | 0 | SO$_2$Me | |
| 1-113 | OEt | (CH$_2$)$_2$OEt | 0 | SO$_2$Me | |
| 1-114 | OEt | (CH$_2$)$_2$OCH$_2$-c-Pr | 0 | SO$_2$Me | |
| 1-115 | OEt | c-Pr | 1 | SO$_2$Me | |
| 1-116 | OEt | CH$_2$-c-Pr | 1 | SO$_2$Me | |
| 1-117 | OEt | (CH$_2$)$_2$OMe | 1 | SO$_2$Me | |
| 1-118 | OEt | (CH$_2$)$_3$OMe | 1 | SO$_2$Me | |
| 1-119 | OEt | (CH$_2$)$_2$OEt | 1 | SO$_2$Me | |
| 1-120 | OEt | (CH$_2$)$_2$OCH$_2$-c-Pr | 1 | SO$_2$Me | |
| 1-121 | OEt | c-Pr | 2 | SO$_2$Me | |
| 1-122 | OEt | CH$_2$-c-Pr | 2 | SO$_2$Me | |
| 1-123 | OEt | (CH$_2$)$_2$OMe | 2 | SO$_2$Me | |
| 1-124 | OEt | (CH$_2$)$_3$OMe | 2 | SO$_2$Me | |
| 1-125 | OEt | (CH$_2$)$_2$OEt | 2 | SO$_2$Me | |
| 1-126 | OEt | (CH$_2$)$_2$OCH$_2$-c-Pr | 2 | SO$_2$Me | |
| 1-127 | NO$_2$ | c-Pr | 0 | SO$_2$Me | |
| 1-128 | NO$_2$ | CH$_2$-c-Pr | 0 | SO$_2$Me | |
| 1-129 | NO$_2$ | (CH$_2$)$_2$OMe | 0 | SO$_2$Me | |
| 1-130 | NO$_2$ | (CH$_2$)$_3$OMe | 0 | SO$_2$Me | |
| 1-131 | NO$_2$ | (CH$_2$)$_2$OEt | 0 | SO$_2$Me | |
| 1-132 | NO$_2$ | (CH$_2$)$_2$OCH$_2$-c-Pr | 0 | SO$_2$Me | |
| 1-133 | NO$_2$ | c-Pr | 1 | SO$_2$Me | |
| 1-134 | NO$_2$ | CH$_2$-c-Pr | 1 | SO$_2$Me | |
| 1-135 | NO$_2$ | (CH$_2$)$_2$OMe | 1 | SO$_2$Me | |
| 1-136 | NO$_2$ | (CH$_2$)$_3$OMe | 1 | SO$_2$Me | |
| 1-137 | NO$_2$ | (CH$_2$)$_2$OEt | 1 | SO$_2$Me | |
| 1-138 | NO$_2$ | (CH$_2$)$_2$OCH$_2$-c-Pr | 1 | SO$_2$Me | |
| 1-139 | NO$_2$ | c-Pr | 2 | SO$_2$Me | |
| 1-140 | NO$_2$ | CH$_2$-c-Pr | 2 | SO$_2$Me | |
| 1-141 | NO$_2$ | (CH$_2$)$_2$OMe | 2 | SO$_2$Me | |
| 1-142 | NO$_2$ | (CH$_2$)$_3$OEt | 2 | SO$_2$Me | |
| 1-143 | NO$_2$ | (CH$_2$)$_2$OEt | 2 | SO$_2$Me | |
| 1-144 | NO$_2$ | (CH$_2$)$_2$OCH$_2$-c-Pr | 2 | SO$_2$Me | |
| 1-145 | SO$_2$Me | c-Pr | 0 | SO$_2$Me | |
| 1-146 | SO$_2$Me | CH$_2$-c-Pr | 0 | SO$_2$Me | |
| 1-147 | SO$_2$Me | (CH$_2$)$_2$OMe | 0 | SO$_2$Me | |
| 1-148 | SO$_2$Me | (CH$_2$)$_3$OMe | 0 | SO$_2$Me | |
| 1-149 | SO$_2$Me | (CH$_2$)$_2$OEt | 0 | SO$_2$Me | |
| 1-150 | SO$_2$Me | (CH$_2$)$_2$OCH$_2$-c-Pr | 0 | SO$_2$Me | |
| 1-151 | SO$_2$Me | c-Pr | 1 | SO$_2$Me | |
| 1-152 | SO$_2$Me | CH$_2$-c-Pr | 1 | SO$_2$Me | |
| 1-153 | SO$_2$Me | (CH$_2$)$_2$OMe | 1 | SO$_2$Me | |
| 1-154 | SO$_2$Me | (CH$_2$)$_3$OMe | 1 | SO$_2$Me | |

TABLE A-continued

Compounds according to the invention of the general formula (I) in which $R^1$ is methyl, $R^4$ is hydrogen and q is zero

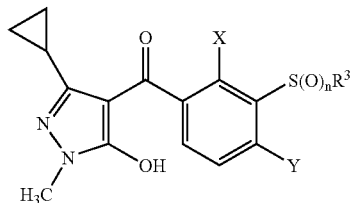

| No. | X | $R^3$ | n | Y | Physical data: $^1$H-NMR: δ[CDCl$_3$] |
|---|---|---|---|---|---|
| 1-155 | SO$_2$Me | (CH$_2$)$_2$OEt | 1 | SO$_2$Me | |
| 1-156 | SO$_2$Me | (CH$_2$)$_2$OCH$_2$-c-Pr | 1 | SO$_2$Me | |
| 1-157 | SO$_2$Me | c-Pr | 2 | SO$_2$Me | |
| 1-158 | SO$_2$Me | CH$_2$-c-Pr | 2 | SO$_2$Me | |
| 1-159 | SO$_2$Me | (CH$_2$)$_2$OMe | 2 | SO$_2$Me | |
| 1-160 | SO$_2$Me | (CH$_2$)$_3$OMe | 2 | SO$_2$Me | |
| 1-161 | SO$_2$Me | (CH$_2$)$_2$OEt | 2 | SO$_2$Me | |
| 1-162 | SO$_2$Me | (CH$_2$)$_2$OCH$_2$-c-Pr | 2 | SO$_2$Me | |
| 1-163 | CH$_2$OMe | c-Pr | 0 | SO$_2$Me | |
| 1-164 | CH$_2$OMe | CH$_2$-c-Pr | 0 | SO$_2$Me | |
| 1-165 | CH$_2$OMe | (CH$_2$)$_2$OMe | 0 | SO$_2$Me | |
| 1-166 | CH$_2$OMe | (CH$_2$)$_3$OMe | 0 | SO$_2$Me | |
| 1-167 | CH$_2$OMe | (CH$_2$)$_2$OEt | 0 | SO$_2$Me | |
| 1-168 | CH$_2$OMe | (CH$_2$)$_2$OCH$_2$-c-Pr | 0 | SO$_2$Me | |
| 1-169 | CH$_2$OMe | c-Pr | 1 | SO$_2$Me | |
| 1-170 | CH$_2$OMe | CH$_2$-c-Pr | 1 | SO$_2$Me | |
| 1-171 | CH$_2$OMe | (CH$_2$)$_2$OMe | 1 | SO$_2$Me | |
| 1-172 | CH$_2$OMe | (CH$_2$)$_3$OMe | 1 | SO$_2$Me | |
| 1-173 | CH$_2$OMe | (CH$_2$)$_2$OEt | 1 | SO$_2$Me | |
| 1-174 | CH$_2$OMe | (CH$_2$)$_2$OCH$_2$-c-Pr | 1 | SO$_2$Me | |
| 1-175 | CH$_2$OMe | c-Pr | 2 | SO$_2$Me | |
| 1-176 | CH$_2$OMe | CH$_2$-c-Pr | 2 | SO$_2$Me | |
| 1-177 | CH$_2$OMe | (CH$_2$)$_2$OMe | 2 | SO$_2$Me | |
| 1-178 | CH$_2$OMe | (CH$_2$)$_3$OMe | 2 | SO$_2$Me | |
| 1-179 | CH$_2$OMe | (CH$_2$)$_2$OEt | 2 | SO$_2$Me | |
| 1-180 | CH$_2$OMe | (CH$_2$)$_2$OCH$_2$-c-Pr | 2 | SO$_2$Me | |
| 1-181 | CH$_2$SO$_2$Me | c-Pr | 0 | SO$_2$Me | |
| 1-182 | CH$_2$SO$_2$Me | CH$_2$-c-Pr | 0 | SO$_2$Me | |
| 1-183 | CH$_2$SO$_2$Me | (CH$_2$)$_2$OMe | 0 | SO$_2$Me | |
| 1-184 | CH$_2$SO$_2$Me | (CH$_2$)$_3$OMe | 0 | SO$_2$Me | |
| 1-185 | CH$_2$SO$_2$Me | (CH$_2$)$_2$OEt | 0 | SO$_2$Me | |
| 1-186 | CH$_2$SO$_2$Me | (CH$_2$)$_2$OCH$_2$-c-Pr | 0 | SO$_2$Me | |
| 1-187 | CH$_2$SO$_2$Me | c-Pr | 1 | SO$_2$Me | |
| 1-188 | CH$_2$SO$_2$Me | CH$_2$-c-Pr | 1 | SO$_2$Me | |
| 1-189 | CH$_2$SO$_2$Me | (CH$_2$)$_2$OMe | 1 | SO$_2$Me | |
| 1-190 | CH$_2$SO$_2$Me | (CH$_2$)$_3$OMe | 1 | SO$_2$Me | |
| 1-191 | CH$_2$SO$_2$Me | (CH$_2$)$_2$OEt | 1 | SO$_2$Me | |
| 1-192 | CH$_2$SO$_2$Me | (CH$_2$)$_2$OCH$_2$-c-Pr | 1 | SO$_2$Me | |
| 1-193 | CH$_2$SO$_2$Me | c-Pr | 2 | SO$_2$Me | |
| 1-194 | CH$_2$SO$_2$Me | CH$_2$-c-Pr | 2 | SO$_2$Me | |
| 1-195 | CH$_2$SO$_2$Me | (CH$_2$)$_2$OMe | 2 | SO$_2$Me | |
| 1-196 | CH$_2$SO$_2$Me | (CH$_2$)$_3$OMe | 2 | SO$_2$Me | |
| 1-197 | CH$_2$SO$_2$Me | (CH$_2$)$_2$OEt | 2 | SO$_2$Me | |
| 1-198 | CH$_2$SO$_2$Me | (CH$_2$)$_2$OCH$_2$-c-Pr | 2 | SO$_2$Me | |
| 1-199 | CH$_2$O(CH$_2$)$_2$OMe | c-Pr | 0 | SO$_2$Me | |
| 1-200 | CH$_2$O(CH$_2$)$_2$OMe | CH$_2$-c-Pr | 0 | SO$_2$Me | |
| 1-201 | CH$_2$O(CH$_2$)$_2$OMe | (CH$_2$)$_2$OMe | 0 | SO$_2$Me | |
| 1-202 | CH$_2$O(CH$_2$)$_2$OMe | (CH$_2$)$_3$OMe | 0 | SO$_2$Me | |
| 1-203 | CH$_2$O(CH$_2$)$_2$OMe | (CH$_2$)$_2$OEt | 0 | SO$_2$Me | |
| 1-204 | CH$_2$O(CH$_2$)$_2$OMe | (CH$_2$)$_2$OCH$_2$-c-Pr | 0 | SO$_2$Me | |
| 1-205 | CH$_2$O(CH$_2$)$_2$OMe | c-Pr | 1 | SO$_2$Me | |
| 1-206 | CH$_2$O(CH$_2$)$_2$OMe | CH$_2$-c-Pr | 1 | SO$_2$Me | |
| 1-207 | CH$_2$O(CH$_2$)$_2$OMe | (CH$_2$)$_2$OMe | 1 | SO$_2$Me | |
| 1-208 | CH$_2$O(CH$_2$)$_2$OMe | (CH$_2$)$_3$OMe | 1 | SO$_2$Me | |
| 1-209 | CH$_2$O(CH$_2$)$_2$OMe | (CH$_2$)$_2$OEt | 1 | SO$_2$Me | |
| 1-210 | CH$_2$O(CH$_2$)$_2$OMe | (CH$_2$)$_2$OCH$_2$-c-Pr | 1 | SO$_2$Me | |
| 1-211 | CH$_2$O(CH$_2$)$_2$OMe | c-Pr | 2 | SO$_2$Me | |
| 1-212 | CH$_2$O(CH$_2$)$_2$OMe | CH$_2$-c-Pr | 2 | SO$_2$Me | |
| 1-213 | CH$_2$O(CH$_2$)$_2$OMe | (CH$_2$)$_2$OMe | 2 | SO$_2$Me | |
| 1-214 | CH$_2$O(CH$_2$)$_2$OMe | (CH$_2$)$_3$OMe | 2 | SO$_2$Me | |
| 1-215 | CH$_2$O(CH$_2$)$_2$OMe | (CH$_2$)$_2$OEt | 2 | SO$_2$Me | |
| 1-216 | CH$_2$O(CH$_2$)$_2$OMe | (CH$_2$)$_2$OCH$_2$-c-Pr | 2 | SO$_2$Me | |
| 1-217 | CH$_2$O(CH$_2$)$_2$OEt | c-Pr | 0 | SO$_2$Me | |

TABLE A-continued

Compounds according to the invention of the general formula (I) in which $R^1$ is methyl, $R^4$ is hydrogen and q is zero

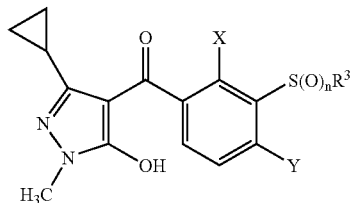

| No. | X | $R^3$ | n | Y | Physical data: $^1$H-NMR: δ[CDCl$_3$] |
|---|---|---|---|---|---|
| 1-218 | CH$_2$O(CH$_2$)$_2$OEt | CH$_2$-c-Pr | 0 | SO$_2$Me | |
| 1-219 | CH$_2$O(CH$_2$)$_2$OEt | (CH$_2$)$_2$OMe | 0 | SO$_2$Me | |
| 1-220 | CH$_2$O(CH$_2$)$_2$OEt | (CH$_2$)$_3$OMe | 0 | SO$_2$Me | |
| 1-221 | CH$_2$O(CH$_2$)$_2$OEt | (CH$_2$)$_2$OEt | 0 | SO$_2$Me | |
| 1-222 | CH$_2$O(CH$_2$)$_2$OEt | (CH$_2$)$_2$OCH$_2$-c-Pr | 0 | SO$_2$Me | |
| 1-223 | CH$_2$O(CH$_2$)$_2$OEt | c-Pr | 1 | SO$_2$Me | |
| 1-224 | CH$_2$O(CH$_2$)$_2$OEt | CH$_2$-c-Pr | 1 | SO$_2$Me | |
| 1-225 | CH$_2$O(CH$_2$)$_2$OEt | (CH$_2$)$_2$OMe | 1 | SO$_2$Me | |
| 1-226 | CH$_2$O(CH$_2$)$_2$OEt | (CH$_2$)$_3$OMe | 1 | SO$_2$Me | |
| 1-227 | CH$_2$O(CH$_2$)$_2$OEt | (CH$_2$)$_2$OEt | 1 | SO$_2$Me | |
| 1-228 | CH$_2$O(CH$_2$)$_2$OEt | (CH$_2$)$_2$OCH$_2$-c-Pr | 1 | SO$_2$Me | |
| 1-229 | CH$_2$O(CH$_2$)$_2$OEt | c-Pr | 2 | SO$_2$Me | |
| 1-230 | CH$_2$O(CH$_2$)$_2$OEt | CH$_2$-c-Pr | 2 | SO$_2$Me | |
| 1-231 | CH$_2$O(CH$_2$)$_2$OEt | (CH$_2$)$_2$OMe | 2 | SO$_2$Me | |
| 1-232 | CH$_2$O(CH$_2$)$_2$OEt | (CH$_2$)$_3$OMe | 2 | SO$_2$Me | |
| 1-233 | CH$_2$O(CH$_2$)$_2$OEt | (CH$_2$)$_2$OEt | 2 | SO$_2$Me | |
| 1-234 | CH$_2$O(CH$_2$)$_2$OEt | (CH$_2$)$_2$OCH$_2$-c-Pr | 2 | SO$_2$Me | |
| 1-235 | CH$_2$O(CH$_2$)$_3$OMe | c-Pr | 0 | SO$_2$Me | |
| 1-236 | CH$_2$O(CH$_2$)$_3$OMe | CH$_2$-c-Pr | 0 | SO$_2$Me | |
| 1-237 | CH$_2$O(CH$_2$)$_3$OMe | (CH$_2$)$_2$OMe | 0 | SO$_2$Me | |
| 1-238 | CH$_2$O(CH$_2$)$_3$OMe | (CH$_2$)$_3$OMe | 0 | SO$_2$Me | |
| 1-239 | CH$_2$O(CH$_2$)$_3$OMe | (CH$_2$)$_2$OEt | 0 | SO$_2$Me | |
| 1-240 | CH$_2$O(CH$_2$)$_3$OMe | (CH$_2$)$_2$OCH$_2$-c-Pr | 0 | SO$_2$Me | |
| 1-241 | CH$_2$O(CH$_2$)$_3$OMe | c-Pr | 1 | SO$_2$Me | |
| 1-242 | CH$_2$O(CH$_2$)$_3$OMe | CH$_2$-c-Pr | 1 | SO$_2$Me | |
| 1-243 | CH$_2$O(CH$_2$)$_3$OMe | (CH$_2$)$_2$OMe | 1 | SO$_2$Me | |
| 1-244 | CH$_2$O(CH$_2$)$_3$OMe | (CH$_2$)$_3$OMe | 1 | SO$_2$Me | |
| 1-245 | CH$_2$O(CH$_2$)$_3$OMe | (CH$_2$)$_2$OEt | 1 | SO$_2$Me | |
| 1-246 | CH$_2$O(CH$_2$)$_3$OMe | (CH$_2$)$_2$OCH$_2$-c-Pr | 1 | SO$_2$Me | |
| 1-247 | CH$_2$O(CH$_2$)$_3$OMe | c-Pr | 2 | SO$_2$Me | |
| 1-248 | CH$_2$O(CH$_2$)$_3$OMe | CH$_2$-c-Pr | 2 | SO$_2$Me | |
| 1-249 | CH$_2$O(CH$_2$)$_3$OMe | (CH$_2$)$_2$OMe | 2 | SO$_2$Me | |
| 1-250 | CH$_2$O(CH$_2$)$_3$OMe | (CH$_2$)$_3$OMe | 2 | SO$_2$Me | |
| 1-251 | CH$_2$O(CH$_2$)$_3$OMe | (CH$_2$)$_2$OEt | 2 | SO$_2$Me | |
| 1-252 | CH$_2$O(CH$_2$)$_3$OMe | (CH$_2$)$_2$OCH$_2$-c-Pr | 2 | SO$_2$Me | |
| 1-253 | CH$_2$OCH$_2$OMe | c-Pr | 0 | SO$_2$Me | |
| 1-254 | CH$_2$OCH$_2$OMe | CH$_2$-c-Pr | 0 | SO$_2$Me | |
| 1-255 | CH$_2$OCH$_2$OMe | (CH$_2$)$_2$OMe | 0 | SO$_2$Me | |
| 1-256 | CH$_2$OCH$_2$OMe | (CH$_2$)$_3$OMe | 0 | SO$_2$Me | |
| 1-257 | CH$_2$OCH$_2$OMe | (CH$_2$)$_2$OEt | 0 | SO$_2$Me | |
| 1-258 | CH$_2$OCH$_2$OMe | (CH$_2$)$_2$OCH$_2$-c-Pr | 0 | SO$_2$Me | |
| 1-259 | CH$_2$OCH$_2$OMe | c-Pr | 1 | SO$_2$Me | |
| 1-260 | CH$_2$OCH$_2$OMe | CH$_2$-c-Pr | 1 | SO$_2$Me | |
| 1-261 | CH$_2$OCH$_2$OMe | (CH$_2$)$_2$OMe | 1 | SO$_2$Me | |
| 1-262 | CH$_2$OCH$_2$OMe | (CH$_2$)$_3$OMe | 1 | SO$_2$Me | |
| 1-263 | CH$_2$OCH$_2$OMe | (CH$_2$)$_2$OEt | 1 | SO$_2$Me | |
| 1-264 | CH$_2$OCH$_2$OMe | (CH$_2$)$_2$OCH$_2$-c-Pr | 1 | SO$_2$Me | |
| 1-265 | CH$_2$OCH$_2$OMe | c-Pr | 2 | SO$_2$Me | |
| 1-266 | CH$_2$OCH$_2$OMe | CH$_2$-c-Pr | 2 | SO$_2$Me | |
| 1-267 | CH$_2$OCH$_2$OMe | (CH$_2$)$_2$OMe | 2 | SO$_2$Me | |
| 1-268 | CH$_2$OCH$_2$OMe | (CH$_2$)$_3$OMe | 2 | SO$_2$Me | |
| 1-269 | CH$_2$OCH$_2$OMe | (CH$_2$)$_2$OEt | 2 | SO$_2$Me | |
| 1-270 | CH$_2$OCH$_2$OMe | (CH$_2$)$_2$OCH$_2$-c-Pr | 2 | SO$_2$Me | |
| 1-271 | CH$_2$OCH$_2$OEt | c-Pr | 0 | SO$_2$Me | |
| 1-272 | CH$_2$OCH$_2$OEt | CH$_2$-c-Pr | 0 | SO$_2$Me | |
| 1-273 | CH$_2$OCH$_2$OEt | (CH$_2$)$_2$OMe | 0 | SO$_2$Me | |
| 1-274 | CH$_2$OCH$_2$OEt | (CH$_2$)$_3$OMe | 0 | SO$_2$Me | |
| 1-275 | CH$_2$OCH$_2$OEt | (CH$_2$)$_2$OEt | 0 | SO$_2$Me | |
| 1-276 | CH$_2$OCH$_2$OEt | (CH$_2$)$_2$OCH$_2$-c-Pr | 0 | SO$_2$Me | |
| 1-277 | CH$_2$OCH$_2$OEt | c-Pr | 1 | SO$_2$Me | |
| 1-278 | CH$_2$OCH$_2$OEt | CH$_2$-c-Pr | 1 | SO$_2$Me | |
| 1-279 | CH$_2$OCH$_2$OEt | (CH$_2$)$_2$OMe | 1 | SO$_2$Me | |
| 1-280 | CH$_2$OCH$_2$OEt | (CH$_2$)$_3$OMe | 1 | SO$_2$Me | |

TABLE A-continued

Compounds according to the invention of the general formula (I) in which $R^1$ is methyl, $R^4$ is hydrogen and q is zero

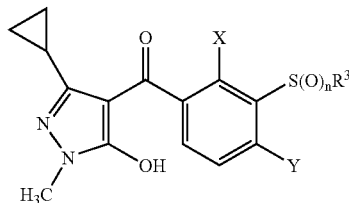

| No. | X | $R^3$ | n | Y | Physical data: $^1$H-NMR: δ[CDCl$_3$] |
|---|---|---|---|---|---|
| 1-281 | CH$_2$OCH$_2$OEt | (CH$_2$)$_2$OEt | 1 | SO$_2$Me | |
| 1-282 | CH$_2$OCH$_2$OEt | (CH$_2$)$_2$OCH$_2$-c-Pr | 1 | SO$_2$Me | |
| 1-283 | CH$_2$OCH$_2$OEt | c-Pr | 2 | SO$_2$Me | |
| 1-284 | CH$_2$OCH$_2$OEt | CH$_2$-c-Pr | 2 | SO$_2$Me | |
| 1-285 | CH$_2$OCH$_2$OEt | (CH$_2$)$_2$OMe | 2 | SO$_2$Me | |
| 1-286 | CH$_2$OCH$_2$OEt | (CH$_2$)$_3$OMe | 2 | SO$_2$Me | |
| 1-287 | CH$_2$OCH$_2$OEt | (CH$_2$)$_2$OEt | 2 | SO$_2$Me | |
| 1-288 | CH$_2$OCH$_2$OEt | (CH$_2$)$_2$OCH$_2$-c-Pr | 2 | SO$_2$Me | |
| 1-289 | CH$_2$O(CH$_2$)$_2$SO$_2$Me | c-Pr | 0 | SO$_2$Me | |
| 1-290 | CH$_2$O(CH$_2$)$_2$SO$_2$Me | CH$_2$-c-Pr | 0 | SO$_2$Me | |
| 1-291 | CH$_2$O(CH$_2$)$_2$SO$_2$Me | (CH$_2$)$_2$OMe | 0 | SO$_2$Me | |
| 1-292 | CH$_2$O(CH$_2$)$_2$SO$_2$Me | (CH$_2$)$_3$OMe | 0 | SO$_2$Me | |
| 1-293 | CH$_2$O(CH$_2$)$_2$SO$_2$Me | (CH$_2$)$_2$OEt | 0 | SO$_2$Me | |
| 1-294 | CH$_2$O(CH$_2$)$_2$SO$_2$Me | (CH$_2$)$_2$OCH$_2$-c-Pr | 0 | SO$_2$Me | |
| 1-295 | CH$_2$O(CH$_2$)$_2$SO$_2$Me | c-Pr | 1 | SO$_2$Me | |
| 1-296 | CH$_2$O(CH$_2$)$_2$SO$_2$Me | CH$_2$-c-Pr | 1 | SO$_2$Me | |
| 1-297 | CH$_2$O(CH$_2$)$_2$SO$_2$Me | (CH$_2$)$_2$OMe | 1 | SO$_2$Me | |
| 1-298 | CH$_2$O(CH$_2$)$_2$SO$_2$Me | (CH$_2$)$_3$OMe | 1 | SO$_2$Me | |
| 1-299 | CH$_2$O(CH$_2$)$_2$SO$_2$Me | (CH$_2$)$_2$OEt | 1 | SO$_2$Me | |
| 1-300 | CH$_2$O(CH$_2$)$_2$SO$_2$Me | (CH$_2$)$_2$OCH$_2$-c-Pr | 1 | SO$_2$Me | |
| 1-301 | CH$_2$O(CH$_2$)$_2$SO$_2$Me | c-Pr | 2 | SO$_2$Me | |
| 1-302 | CH$_2$O(CH$_2$)$_2$SO$_2$Me | CH$_2$-c-Pr | 2 | SO$_2$Me | |
| 1-303 | CH$_2$O(CH$_2$)$_2$SO$_2$Me | (CH$_2$)$_2$OMe | 2 | SO$_2$Me | |
| 1-304 | CH$_2$O(CH$_2$)$_2$SO$_2$Me | (CH$_2$)$_3$OMe | 2 | SO$_2$Me | |
| 1-305 | CH$_2$O(CH$_2$)$_2$SO$_2$Me | (CH$_2$)$_2$OEt | 2 | SO$_2$Me | |
| 1-306 | CH$_2$O(CH$_2$)$_2$SO$_2$Me | (CH$_2$)$_2$OCH$_2$-c-Pr | 2 | SO$_2$Me | |
| 1-307 | CH$_2$SO$_2$(CH$_2$)$_2$OMe | c-Pr | 0 | SO$_2$Me | |
| 1-308 | CH$_2$SO$_2$(CH$_2$)$_2$OMe | CH$_2$-c-Pr | 0 | SO$_2$Me | |
| 1-309 | CH$_2$SO$_2$(CH$_2$)$_2$OMe | (CH$_2$)$_2$OMe | 0 | SO$_2$Me | |
| 1-310 | CH$_2$SO$_2$(CH$_2$)$_2$OMe | (CH$_2$)$_3$OMe | 0 | SO$_2$Me | |
| 1-311 | CH$_2$SO$_2$(CH$_2$)$_2$OMe | (CH$_2$)$_2$OEt | 0 | SO$_2$Me | |
| 1-312 | CH$_2$SO$_2$(CH$_2$)$_2$OMe | (CH$_2$)$_2$OCH$_2$-c-Pr | 0 | SO$_2$Me | |
| 1-313 | CH$_2$SO$_2$(CH$_2$)$_2$OMe | c-Pr | 1 | SO$_2$Me | |
| 1-314 | CH$_2$SO$_2$(CH$_2$)$_2$OMe | CH$_2$-c-Pr | 1 | SO$_2$Me | |
| 1-315 | CH$_2$SO$_2$(CH$_2$)$_2$OMe | (CH$_2$)$_2$OMe | 1 | SO$_2$Me | |
| 1-316 | CH$_2$SO$_2$(CH$_2$)$_2$OMe | (CH$_2$)$_3$OMe | 1 | SO$_2$Me | |
| 1-317 | CH$_2$SO$_2$(CH$_2$)$_2$OMe | (CH$_2$)$_2$OEt | 1 | SO$_2$Me | |
| 1-318 | CH$_2$SO$_2$(CH$_2$)$_2$OMe | (CH$_2$)$_2$OCH$_2$-c-Pr | 1 | SO$_2$Me | |
| 1-319 | CH$_2$SO$_2$(CH$_2$)$_2$OMe | c-Pr | 2 | SO$_2$Me | |
| 1-320 | CH$_2$SO$_2$(CH$_2$)$_2$OMe | CH$_2$-c-Pr | 2 | SO$_2$Me | |
| 1-321 | CH$_2$SO$_2$(CH$_2$)$_2$OMe | (CH$_2$)$_2$OMe | 2 | SO$_2$Me | |
| 1-322 | CH$_2$SO$_2$(CH$_2$)$_2$OMe | (CH$_2$)$_3$OMe | 2 | SO$_2$Me | |
| 1-323 | CH$_2$SO$_2$(CH$_2$)$_2$OMe | (CH$_2$)$_2$OEt | 2 | SO$_2$Me | |
| 1-324 | CH$_2$SO$_2$(CH$_2$)$_2$OMe | (CH$_2$)$_2$OCH$_2$-c-Pr | 2 | SO$_2$Me | |
| 1-325 | CH$_2$SO$_2$(CH$_2$)$_2$SO$_2$Me | c-Pr | 0 | SO$_2$Me | |
| 1-326 | CH$_2$SO$_2$(CH$_2$)$_2$SO$_2$Me | CH$_2$-c-Pr | 0 | SO$_2$Me | |
| 1-327 | CH$_2$SO$_2$(CH$_2$)$_2$SO$_2$Me | (CH$_2$)$_2$OMe | 0 | SO$_2$Me | |
| 1-328 | CH$_2$SO$_2$(CH$_2$)$_2$SO$_2$Me | (CH$_2$)$_3$OMe | 0 | SO$_2$Me | |
| 1-329 | CH$_2$SO$_2$(CH$_2$)$_2$SO$_2$Me | (CH$_2$)$_2$OEt | 0 | SO$_2$Me | |
| 1-330 | CH$_2$SO$_2$(CH$_2$)$_2$SO$_2$Me | (CH$_2$)$_2$OCH$_2$-c-Pr | 0 | SO$_2$Me | |
| 1-331 | CH$_2$SO$_2$(CH$_2$)$_2$SO$_2$Me | c-Pr | 1 | SO$_2$Me | |
| 1-332 | CH$_2$SO$_2$(CH$_2$)$_2$SO$_2$Me | CH$_2$-c-Pr | 1 | SO$_2$Me | |
| 1-333 | CH$_2$SO$_2$(CH$_2$)$_2$SO$_2$Me | (CH$_2$)$_2$OMe | 1 | SO$_2$Me | |
| 1-334 | CH$_2$SO$_2$(CH$_2$)$_2$SO$_2$Me | (CH$_2$)$_3$OMe | 1 | SO$_2$Me | |
| 1-335 | CH$_2$SO$_2$(CH$_2$)$_2$SO$_2$Me | (CH$_2$)$_2$OEt | 1 | SO$_2$Me | |
| 1-336 | CH$_2$SO$_2$(CH$_2$)$_2$SO$_2$Me | (CH$_2$)$_2$OCH$_2$-c-Pr | 1 | SO$_2$Me | |
| 1-337 | CH$_2$SO$_2$(CH$_2$)$_2$SO$_2$Me | c-Pr | 2 | SO$_2$Me | |
| 1-338 | CH$_2$SO$_2$(CH$_2$)$_2$SO$_2$Me | CH$_2$-c-Pr | 2 | SO$_2$Me | |
| 1-339 | CH$_2$SO$_2$(CH$_2$)$_2$SO$_2$Me | (CH$_2$)$_2$OMe | 2 | SO$_2$Me | |
| 1-340 | CH$_2$SO$_2$(CH$_2$)$_2$SO$_2$Me | (CH$_2$)$_3$OMe | 2 | SO$_2$Me | |
| 1-341 | CH$_2$SO$_2$(CH$_2$)$_2$SO$_2$Me | (CH$_2$)$_2$OEt | 2 | SO$_2$Me | |
| 1-342 | CH$_2$SO$_2$(CH$_2$)$_2$SO$_2$Me | (CH$_2$)$_2$OCH$_2$-c-Pr | 2 | SO$_2$Me | |
| 1-343 | Cl | c-Pr | 0 | SO$_2$Et | |

TABLE A-continued

Compounds according to the invention of the general formula (I) in which $R^1$ is methyl, $R^4$ is hydrogen and q is zero

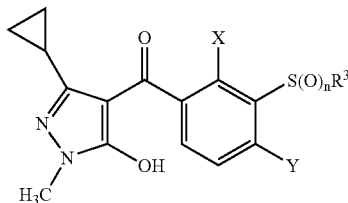

| No. | X | $R^3$ | n | Y | Physical data: $^1$H-NMR: δ[CDCl$_3$] |
|---|---|---|---|---|---|
| 1-344 | Cl | CH$_2$-c-Pr | 0 | SO$_2$Et | |
| 1-345 | Cl | (CH$_2$)$_2$OMe | 0 | SO$_2$Et | |
| 1-346 | Cl | (CH$_2$)$_3$OMe | 0 | SO$_2$Et | |
| 1-347 | Cl | (CH$_2$)$_2$OEt | 0 | SO$_2$Et | |
| 1-348 | Cl | (CH$_2$)$_2$OCH$_2$-c-Pr | 0 | SO$_2$Et | |
| 1-349 | Cl | c-Pr | 1 | SO$_2$Et | |
| 1-350 | Cl | CH$_2$-c-Pr | 1 | SO$_2$Et | |
| 1-351 | Cl | (CH$_2$)$_2$OMe | 1 | SO$_2$Et | |
| 1-352 | Cl | (CH$_2$)$_3$OMe | 1 | SO$_2$Et | |
| 1-353 | Cl | (CH$_2$)$_2$OEt | 1 | SO$_2$Et | |
| 1-354 | Cl | (CH$_2$)$_2$OCH$_2$-c-Pr | 1 | SO$_2$Et | |
| 1-355 | Cl | c-Pr | 2 | SO$_2$Et | |
| 1-356 | Cl | CH$_2$-c-Pr | 2 | SO$_2$Et | |
| 1-357 | Cl | (CH$_2$)$_2$OMe | 2 | SO$_2$Et | |
| 1-358 | Cl | (CH$_2$)$_3$OMe | 2 | SO$_2$Et | |
| 1-359 | Cl | (CH$_2$)$_2$OEt | 2 | SO$_2$Et | |
| 1-360 | Cl | (CH$_2$)$_2$OCH$_2$-c-Pr | 2 | SO$_2$Et | |
| 1-361 | Br | c-Pr | 0 | SO$_2$Et | |
| 1-362 | Br | CH$_2$-c-Pr | 0 | SO$_2$Et | |
| 1-363 | Br | (CH$_2$)$_2$OMe | 0 | SO$_2$Et | |
| 1-364 | Br | (CH$_2$)$_3$OMe | 0 | SO$_2$Et | |
| 1-365 | Br | (CH$_2$)$_2$OEt | 0 | SO$_2$Et | |
| 1-366 | Br | (CH$_2$)$_2$OCH$_2$-c-Pr | 0 | SO$_2$Et | |
| 1-367 | Br | c-Pr | 1 | SO$_2$Et | |
| 1-368 | Br | CH$_2$-c-Pr | 1 | SO$_2$Et | |
| 1-369 | Br | (CH$_2$)$_2$OMe | 1 | SO$_2$Et | |
| 1-370 | Br | (CH$_2$)$_3$OMe | 1 | SO$_2$Et | |
| 1-371 | Br | (CH$_2$)$_2$OEt | 1 | SO$_2$Et | |
| 1-372 | Br | (CH$_2$)$_2$OCH$_2$-c-Pr | 1 | SO$_2$Et | |
| 1-373 | Br | c-Pr | 2 | SO$_2$Et | |
| 1-374 | Br | CH$_2$-c-Pr | 2 | SO$_2$Et | |
| 1-375 | Br | (CH$_2$)$_2$OMe | 2 | SO$_2$Et | |
| 1-376 | Br | (CH$_2$)$_3$OMe | 2 | SO$_2$Et | |
| 1-377 | Br | (CH$_2$)$_2$OEt | 2 | SO$_2$Et | |
| 1-378 | Br | (CH$_2$)$_2$OCH$_2$-c-Pr | 2 | SO$_2$Et | |
| 1-379 | Me | c-Pr | 0 | SO$_2$Et | |
| 1-380 | Me | CH$_2$-c-Pr | 0 | SO$_2$Et | |
| 1-381 | Me | (CH$_2$)$_2$OMe | 0 | SO$_2$Et | |
| 1-382 | Me | (CH$_2$)$_3$OMe | 0 | SO$_2$Et | |
| 1-383 | Me | (CH$_2$)$_2$OEt | 0 | SO$_2$Et | |
| 1-384 | Me | (CH$_2$)$_2$OCH$_2$-c-Pr | 0 | SO$_2$Et | |
| 1-385 | Me | c-Pr | 1 | SO$_2$Et | |
| 1-386 | Me | CH$_2$-c-Pr | 1 | SO$_2$Et | |
| 1-387 | Me | (CH$_2$)$_2$OMe | 1 | SO$_2$Et | |
| 1-388 | Me | (CH$_2$)$_3$OMe | 1 | SO$_2$Et | |
| 1-389 | Me | (CH$_2$)$_2$OEt | 1 | SO$_2$Et | |
| 1-390 | Me | (CH$_2$)$_2$OCH$_2$-c-Pr | 1 | SO$_2$Et | |
| 1-391 | Me | c-Pr | 2 | SO$_2$Et | |
| 1-392 | Me | CH$_2$-c-Pr | 2 | SO$_2$Et | |
| 1-393 | Me | (CH$_2$)$_2$OMe | 2 | SO$_2$Et | 8.30 (d, 1H), 7.64 (d, 1H), 4.02-3.87 (m, 4H), 3.81 (q, 2H), 3.62 (s, 3H), 3.33 (s, 3H), 2.77 (s, 3H), 1.37 (t, 3H), 0.86-0.70 (m, 3H), 0.55-0.44 (m, 2H) |
| 1-394 | Me | (CH$_2$)$_3$OMe | 2 | SO$_2$Et | |
| 1-395 | Me | (CH$_2$)$_2$OEt | 2 | SO$_2$Et | |
| 1-396 | Me | (CH$_2$)$_2$OCH$_2$-c-Pr | 2 | SO$_2$Et | |
| 1-397 | Et | c-Pr | 0 | SO$_2$Et | |
| 1-398 | Et | CH$_2$-c-Pr | 0 | SO$_2$Et | |
| 1-399 | Et | (CH$_2$)$_2$OMe | 0 | SO$_2$Et | |
| 1-400 | Et | (CH$_2$)$_3$OMe | 0 | SO$_2$Et | |
| 1-401 | Et | (CH$_2$)$_2$OEt | 0 | SO$_2$Et | |

TABLE A-continued

Compounds according to the invention of the general formula (I) in which $R^1$ is methyl, $R^4$ is hydrogen and q is zero

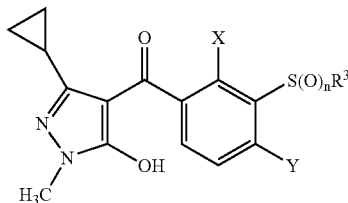

| No. | X | $R^3$ | n | Y | Physical data: $^1$H-NMR: δ[CDCl$_3$] |
|---|---|---|---|---|---|
| 1-402 | Et | (CH$_2$)$_2$OCH$_2$-c-Pr | 0 | SO$_2$Et | |
| 1-403 | Et | c-Pr | 1 | SO$_2$Et | |
| 1-404 | Et | CH$_2$-c-Pr | 1 | SO$_2$Et | |
| 1-405 | Et | (CH$_2$)$_2$OMe | 1 | SO$_2$Et | |
| 1-406 | Et | (CH$_2$)$_3$OMe | 1 | SO$_2$Et | |
| 1-407 | Et | (CH$_2$)$_2$OEt | 1 | SO$_2$Et | |
| 1-408 | Et | (CH$_2$)$_2$OCH$_2$-c-Pr | 1 | SO$_2$Et | |
| 1-409 | Et | c-Pr | 2 | SO$_2$Et | |
| 1-410 | Et | CH$_2$-c-Pr | 2 | SO$_2$Et | |
| 1-411 | Et | (CH$_2$)$_2$OMe | 2 | SO$_2$Et | |
| 1-412 | Et | (CH$_2$)$_3$OMe | 2 | SO$_2$Et | |
| 1-413 | Et | (CH$_2$)$_2$OEt | 2 | SO$_2$Et | |
| 1-414 | Et | (CH$_2$)$_2$OCH$_2$-c-Pr | 2 | SO$_2$Et | |
| 1-415 | CF$_3$ | c-Pr | 0 | SO$_2$Et | |
| 1-416 | CF$_3$ | CH$_2$-c-Pr | 0 | SO$_2$Et | |
| 1-417 | CF$_3$ | (CH$_2$)$_2$OMe | 0 | SO$_2$Et | |
| 1-418 | CF$_3$ | (CH$_2$)$_3$OMe | 0 | SO$_2$Et | |
| 1-419 | CF$_3$ | (CH$_2$)$_2$OEt | 0 | SO$_2$Et | |
| 1-420 | CF$_3$ | (CH$_2$)$_2$OCH$_2$-c-Pr | 0 | SO$_2$Et | |
| 1-421 | CF$_3$ | c-Pr | 1 | SO$_2$Et | |
| 1-422 | CF$_3$ | CH$_2$-c-Pr | 1 | SO$_2$Et | |
| 1-423 | CF$_3$ | (CH$_2$)$_2$OMe | 1 | SO$_2$Et | |
| 1-424 | CF$_3$ | (CH$_2$)$_3$OMe | 1 | SO$_2$Et | |
| 1-425 | CF$_3$ | (CH$_2$)$_2$OEt | 1 | SO$_2$Et | |
| 1-426 | CF$_3$ | (CH$_2$)$_2$OCH$_2$-c-Pr | 1 | SO$_2$Et | |
| 1-427 | CF$_3$ | c-Pr | 2 | SO$_2$Et | |
| 1-428 | CF$_3$ | CH$_2$-c-Pr | 2 | SO$_2$Et | |
| 1-429 | CF$_3$ | (CH$_2$)$_2$OMe | 2 | SO$_2$Et | |
| 1-430 | CF$_3$ | (CH$_2$)$_3$OMe | 2 | SO$_2$Et | |
| 1-431 | CF$_3$ | (CH$_2$)$_2$OEt | 2 | SO$_2$Et | |
| 1-432 | CF$_3$ | (CH$_2$)$_2$OCH$_2$-c-Pr | 2 | SO$_2$Et | |
| 1-433 | OMe | c-Pr | 0 | SO$_2$Et | |
| 1-434 | OMe | CH$_2$-c-Pr | 0 | SO$_2$Et | |
| 1-435 | OMe | (CH$_2$)$_2$OMe | 0 | SO$_2$Et | |
| 1-436 | OMe | (CH$_2$)$_3$OMe | 0 | SO$_2$Et | |
| 1-437 | OMe | (CH$_2$)$_2$OEt | 0 | SO$_2$Et | |
| 1-438 | OMe | (CH$_2$)$_2$OCH$_2$-c-Pr | 0 | SO$_2$Et | |
| 1-439 | OMe | c-Pr | 1 | SO$_2$Et | |
| 1-440 | OMe | CH$_2$-c-Pr | 1 | SO$_2$Et | |
| 1-441 | OMe | (CH$_2$)$_2$OMe | 1 | SO$_2$Et | |
| 1-442 | OMe | (CH$_2$)$_3$OMe | 1 | SO$_2$Et | |
| 1-443 | OMe | (CH$_2$)$_2$OEt | 1 | SO$_2$Et | |
| 1-444 | OMe | (CH$_2$)$_2$OCH$_2$-c-Pr | 1 | SO$_2$Et | |
| 1-445 | OMe | c-Pr | 2 | SO$_2$Et | |
| 1-446 | OMe | CH$_2$-c-Pr | 2 | SO$_2$Et | |
| 1-447 | OMe | (CH$_2$)$_2$OMe | 2 | SO$_2$Et | |
| 1-448 | OMe | (CH$_2$)$_3$OMe | 2 | SO$_2$Et | |
| 1-449 | OMe | (CH$_2$)$_2$OEt | 2 | SO$_2$Et | |
| 1-450 | OMe | (CH$_2$)$_2$OCH$_2$-c-Pr | 2 | SO$_2$Et | |
| 1-451 | OEt | c-Pr | 0 | SO$_2$Et | |
| 1-452 | OEt | CH$_2$-c-Pr | 0 | SO$_2$Et | |
| 1-453 | OEt | (CH$_2$)$_2$OMe | 0 | SO$_2$Et | |
| 1-454 | OEt | (CH$_2$)$_3$OMe | 0 | SO$_2$Et | |
| 1-455 | OEt | (CH$_2$)$_2$OEt | 0 | SO$_2$Et | |
| 1-456 | OEt | (CH$_2$)$_2$OCH$_2$-c-Pr | 0 | SO$_2$Et | |
| 1-457 | OEt | c-Pr | 1 | SO$_2$Et | |
| 1-458 | OEt | CH$_2$-c-Pr | 1 | SO$_2$Et | |
| 1-459 | OEt | (CH$_2$)$_2$OMe | 1 | SO$_2$Et | |
| 1-460 | OEt | (CH$_2$)$_3$OMe | 1 | SO$_2$Et | |
| 1-461 | OEt | (CH$_2$)$_2$OEt | 1 | SO$_2$Et | |
| 1-462 | OEt | (CH$_2$)$_2$OCH$_2$-c-Pr | 1 | SO$_2$Et | |
| 1-463 | OEt | c-Pr | 2 | SO$_2$Et | |
| 1-464 | OEt | CH$_2$-c-Pr | 2 | SO$_2$Et | |

TABLE A-continued

Compounds according to the invention of the general formula (I) in which $R^1$ is methyl, $R^4$ is hydrogen and q is zero

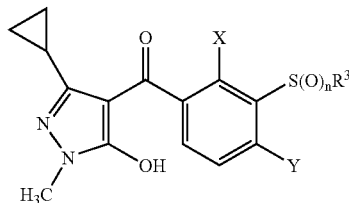

| No. | X | $R^3$ | n | Y | Physical data: $^1$H-NMR: δ[CDCl$_3$] |
|---|---|---|---|---|---|
| 1-465 | OEt | (CH$_2$)$_2$OMe | 2 | SO$_2$Et | |
| 1-466 | OEt | (CH$_2$)$_3$OMe | 2 | SO$_2$Et | |
| 1-467 | OEt | (CH$_2$)$_2$OEt | 2 | SO$_2$Et | |
| 1-468 | OEt | (CH$_2$)$_2$OCH$_2$-c-Pr | 2 | SO$_2$Et | |
| 1-469 | NO$_2$ | c-Pr | 0 | SO$_2$Et | |
| 1-470 | NO$_2$ | CH$_2$-c-Pr | 0 | SO$_2$Et | |
| 1-471 | NO$_2$ | (CH$_2$)$_2$OMe | 0 | SO$_2$Et | |
| 1-472 | NO$_2$ | (CH$_2$)$_3$OMe | 0 | SO$_2$Et | |
| 1-473 | NO$_2$ | (CH$_2$)$_2$OEt | 0 | SO$_2$Et | |
| 1-474 | NO$_2$ | (CH$_2$)$_2$OCH$_2$-c-Pr | 0 | SO$_2$Et | |
| 1-475 | NO$_2$ | c-Pr | 1 | SO$_2$Et | |
| 1-476 | NO$_2$ | CH$_2$-c-Pr | 1 | SO$_2$Et | |
| 1-477 | NO$_2$ | (CH$_2$)$_2$OMe | 1 | SO$_2$Et | |
| 1-478 | NO$_2$ | (CH$_2$)$_3$OMe | 1 | SO$_2$Et | |
| 1-479 | NO$_2$ | (CH$_2$)$_2$OEt | 1 | SO$_2$Et | |
| 1-480 | NO$_2$ | (CH$_2$)$_2$OCH$_2$-c-Pr | 1 | SO$_2$Et | |
| 1-481 | NO$_2$ | c-Pr | 2 | SO$_2$Et | |
| 1-482 | NO$_2$ | CH$_2$-c-Pr | 2 | SO$_2$Et | |
| 1-483 | NO$_2$ | (CH$_2$)$_2$OMe | 2 | SO$_2$Et | |
| 1-484 | NO$_2$ | (CH$_2$)$_3$OMe | 2 | SO$_2$Et | |
| 1-485 | NO$_2$ | (CH$_2$)$_2$OEt | 2 | SO$_2$Et | |
| 1-486 | NO$_2$ | (CH$_2$)$_2$OCH$_2$-c-Pr | 2 | SO$_2$Et | |
| 1-487 | SO$_2$Me | c-Pr | 0 | SO$_2$Et | |
| 1-488 | SO$_2$Me | CH$_2$-c-Pr | 0 | SO$_2$Et | |
| 1-489 | SO$_2$Me | (CH$_2$)$_2$OMe | 0 | SO$_2$Et | |
| 1-490 | SO$_2$Me | (CH$_2$)$_3$OMe | 0 | SO$_2$Et | |
| 1-491 | SO$_2$Me | (CH$_2$)$_2$OEt | 0 | SO$_2$Et | |
| 1-492 | SO$_2$Me | (CH$_2$)$_2$OCH$_2$-c-Pr | 0 | SO$_2$Et | |
| 1-493 | SO$_2$Me | c-Pr | 1 | SO$_2$Et | |
| 1-494 | SO$_2$Me | CH$_2$-c-Pr | 1 | SO$_2$Et | |
| 1-495 | SO$_2$Me | (CH$_2$)$_2$OMe | 1 | SO$_2$Et | |
| 1-496 | SO$_2$Me | (CH$_2$)$_3$OMe | 1 | SO$_2$Et | |
| 1-497 | SO$_2$Me | (CH$_2$)$_2$OEt | 1 | SO$_2$Et | |
| 1-498 | SO$_2$Me | (CH$_2$)$_2$OCH$_2$-c-Pr | 1 | SO$_2$Et | |
| 1-499 | SO$_2$Me | c-Pr | 2 | SO$_2$Et | |
| 1-500 | SO$_2$Me | CH$_2$-c-Pr | 2 | SO$_2$Et | |
| 1-501 | SO$_2$Me | (CH$_2$)$_2$OMe | 2 | SO$_2$Et | |
| 1-502 | SO$_2$Me | (CH$_2$)$_3$OMe | 2 | SO$_2$Et | |
| 1-503 | SO$_2$Me | (CH$_2$)$_2$OEt | 2 | SO$_2$Et | |
| 1-504 | SO$_2$Me | (CH$_2$)$_2$OCH$_2$-c-Pr | 2 | SO$_2$Et | |
| 1-505 | CH$_2$OMe | c-Pr | 0 | SO$_2$Et | |
| 1-506 | CH$_2$OMe | CH$_2$-c-Pr | 0 | SO$_2$Et | |
| 1-507 | CH$_2$OMe | (CH$_2$)$_2$OMe | 0 | SO$_2$Et | |
| 1-508 | CH$_2$OMe | (CH$_2$)$_3$OMe | 0 | SO$_2$Et | |
| 1-509 | CH$_2$OMe | (CH$_2$)$_2$OEt | 0 | SO$_2$Et | |
| 1-510 | CH$_2$OMe | (CH$_2$)$_2$OCH$_2$-c-Pr | 0 | SO$_2$Et | |
| 1-511 | CH$_2$OMe | c-Pr | 1 | SO$_2$Et | |
| 1-512 | CH$_2$OMe | CH$_2$-c-Pr | 1 | SO$_2$Et | |
| 1-513 | CH$_2$OMe | (CH$_2$)$_2$OMe | 1 | SO$_2$Et | |
| 1-514 | CH$_2$OMe | (CH$_2$)$_3$OMe | 1 | SO$_2$Et | |
| 1-515 | CH$_2$OMe | (CH$_2$)$_2$OEt | 1 | SO$_2$Et | |
| 1-516 | CH$_2$OMe | (CH$_2$)$_2$OCH$_2$-c-Pr | 1 | SO$_2$Et | |
| 1-517 | CH$_2$OMe | c-Pr | 2 | SO$_2$Et | |
| 1-518 | CH$_2$OMe | CH$_2$-c-Pr | 2 | SO$_2$Et | |
| 1-519 | CH$_2$OMe | (CH$_2$)$_2$OMe | 2 | SO$_2$Et | |
| 1-520 | CH$_2$OMe | (CH$_2$)$_3$OMe | 2 | SO$_2$Et | |
| 1-521 | CH$_2$OMe | (CH$_2$)$_2$OEt | 2 | SO$_2$Et | |
| 1-522 | CH$_2$OMe | (CH$_2$)$_2$OCH$_2$-c-Pr | 2 | SO$_2$Et | |
| 1-523 | CH$_2$SO$_2$Me | c-Pr | 0 | SO$_2$Et | |
| 1-524 | CH$_2$SO$_2$Me | CH$_2$-c-Pr | 0 | SO$_2$Et | |
| 1-525 | CH$_2$SO$_2$Me | (CH$_2$)$_2$OMe | 0 | SO$_2$Et | |
| 1-526 | CH$_2$SO$_2$Me | (CH$_2$)$_3$OMe | 0 | SO$_2$Et | |
| 1-527 | CH$_2$SO$_2$Me | (CH$_2$)$_2$OEt | 0 | SO$_2$Et | |

TABLE A-continued

Compounds according to the invention of the general formula (I) in which $R^1$ is methyl, $R^4$ is hydrogen and q is zero

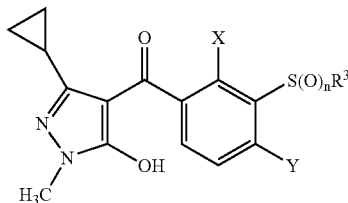

| No. | X | $R^3$ | n | Y | Physical data: $^1$H-NMR: δ[CDCl$_3$] |
|---|---|---|---|---|---|
| 1-528 | CH$_2$SO$_2$Me | (CH$_2$)$_2$OCH$_2$-c-Pr | 0 | SO$_2$Et | |
| 1-529 | CH$_2$SO$_2$Me | c-Pr | 1 | SO$_2$Et | |
| 1-530 | CH$_2$SO$_2$Me | CH$_2$-c-Pr | 1 | SO$_2$Et | |
| 1-531 | CH$_2$SO$_2$Me | (CH$_2$)$_2$OMe | 1 | SO$_2$Et | |
| 1-532 | CH$_2$SO$_2$Me | (CH$_2$)$_3$OMe | 1 | SO$_2$Et | |
| 1-533 | CH$_2$SO$_2$Me | (CH$_2$)$_2$OEt | 1 | SO$_2$Et | |
| 1-534 | CH$_2$SO$_2$Me | (CH$_2$)$_2$OCH$_2$-c-Pr | 1 | SO$_2$Et | |
| 1-535 | CH$_2$SO$_2$Me | c-Pr | 2 | SO$_2$Et | |
| 1-536 | CH$_2$SO$_2$Me | CH$_2$-c-Pr | 2 | SO$_2$Et | |
| 1-537 | CH$_2$SO$_2$Me | (CH$_2$)$_2$OMe | 2 | SO$_2$Et | |
| 1-538 | CH$_2$SO$_2$Me | (CH$_2$)$_3$OMe | 2 | SO$_2$Et | |
| 1-539 | CH$_2$SO$_2$Me | (CH$_2$)$_2$OEt | 2 | SO$_2$Et | |
| 1-540 | CH$_2$SO$_2$Me | (CH$_2$)$_2$OCH$_2$-c-Pr | 2 | SO$_2$Et | |
| 1-541 | CH$_2$O(CH$_2$)$_2$OMe | c-Pr | 0 | SO$_2$Et | |
| 1-542 | CH$_2$O(CH$_2$)$_2$OMe | CH$_2$-c-Pr | 0 | SO$_2$Et | |
| 1-543 | CH$_2$O(CH$_2$)$_2$OMe | (CH$_2$)$_2$OMe | 0 | SO$_2$Et | |
| 1-544 | CH$_2$O(CH$_2$)$_2$OMe | (CH$_2$)$_3$OMe | 0 | SO$_2$Et | |
| 1-545 | CH$_2$O(CH$_2$)$_2$OMe | (CH$_2$)$_2$OEt | 0 | SO$_2$Et | |
| 1-546 | CH$_2$O(CH$_2$)$_2$OMe | (CH$_2$)$_2$OCH$_2$-c-Pr | 0 | SO$_2$Et | |
| 1-547 | CH$_2$O(CH$_2$)$_2$OMe | c-Pr | 1 | SO$_2$Et | |
| 1-548 | CH$_2$O(CH$_2$)$_2$OMe | CH$_2$-c-Pr | 1 | SO$_2$Et | |
| 1-549 | CH$_2$O(CH$_2$)$_2$OMe | (CH$_2$)$_2$OMe | 1 | SO$_2$Et | |
| 1-550 | CH$_2$O(CH$_2$)$_2$OMe | (CH$_2$)$_3$OMe | 1 | SO$_2$Et | |
| 1-551 | CH$_2$O(CH$_2$)$_2$OMe | (CH$_2$)$_2$OEt | 1 | SO$_2$Et | |
| 1-552 | CH$_2$O(CH$_2$)$_2$OMe | (CH$_2$)$_2$OCH$_2$-c-Pr | 1 | SO$_2$Et | |
| 1-553 | CH$_2$O(CH$_2$)$_2$OMe | c-Pr | 2 | SO$_2$Et | |
| 1-554 | CH$_2$O(CH$_2$)$_2$OMe | CH$_2$-c-Pr | 2 | SO$_2$Et | |
| 1-555 | CH$_2$O(CH$_2$)$_2$OMe | (CH$_2$)$_2$OMe | 2 | SO$_2$Et | |
| 1-556 | CH$_2$O(CH$_2$)$_2$OMe | (CH$_2$)$_3$OMe | 2 | SO$_2$Et | |
| 1-557 | CH$_2$O(CH$_2$)$_2$OMe | (CH$_2$)$_2$OEt | 2 | SO$_2$Et | |
| 1-558 | CH$_2$O(CH$_2$)$_2$OMe | (CH$_2$)$_2$OCH$_2$-c-Pr | 2 | SO$_2$Et | |
| 1-559 | CH$_2$O(CH$_2$)$_2$OEt | c-Pr | 0 | SO$_2$Et | |
| 1-560 | CH$_2$O(CH$_2$)$_2$OEt | CH$_2$-c-Pr | 0 | SO$_2$Et | |
| 1-561 | CH$_2$O(CH$_2$)$_2$OEt | (CH$_2$)$_2$OMe | 0 | SO$_2$Et | |
| 1-562 | CH$_2$O(CH$_2$)$_2$OEt | (CH$_2$)$_3$OMe | 0 | SO$_2$Et | |
| 1-563 | CH$_2$O(CH$_2$)$_2$OEt | (CH$_2$)$_2$OEt | 0 | SO$_2$Et | |
| 1-564 | CH$_2$O(CH$_2$)$_2$OEt | (CH$_2$)$_2$OCH$_2$-c-Pr | 0 | SO$_2$Et | |
| 1-565 | CH$_2$O(CH$_2$)$_2$OEt | c-Pr | 1 | SO$_2$Et | |
| 1-566 | CH$_2$O(CH$_2$)$_2$OEt | CH$_2$-c-Pr | 1 | SO$_2$Et | |
| 1-567 | CH$_2$O(CH$_2$)$_2$OEt | (CH$_2$)$_2$OMe | 1 | SO$_2$Et | |
| 1-568 | CH$_2$O(CH$_2$)$_2$OEt | (CH$_2$)$_3$OMe | 1 | SO$_2$Et | |
| 1-569 | CH$_2$O(CH$_2$)$_2$OEt | (CH$_2$)$_2$OEt | 1 | SO$_2$Et | |
| 1-570 | CH$_2$O(CH$_2$)$_2$OEt | (CH$_2$)$_2$OCH$_2$-c-Pr | 1 | SO$_2$Et | |
| 1-571 | CH$_2$O(CH$_2$)$_2$OEt | c-Pr | 2 | SO$_2$Et | |
| 1-572 | CH$_2$O(CH$_2$)$_2$OEt | CH$_2$-c-Pr | 2 | SO$_2$Et | |
| 1-573 | CH$_2$O(CH$_2$)$_2$OEt | (CH$_2$)$_2$OMe | 2 | SO$_2$Et | |
| 1-574 | CH$_2$O(CH$_2$)$_2$OEt | (CH$_2$)$_3$OMe | 2 | SO$_2$Et | |
| 1-575 | CH$_2$O(CH$_2$)$_2$OEt | (CH$_2$)$_2$OEt | 2 | SO$_2$Et | |
| 1-576 | CH$_2$O(CH$_2$)$_2$OEt | (CH$_2$)$_2$OCH$_2$-c-Pr | 2 | SO$_2$Et | |
| 1-577 | CH$_2$O(CH$_2$)$_3$OMe | c-Pr | 0 | SO$_2$Et | |
| 1-578 | CH$_2$O(CH$_2$)$_3$OMe | CH$_2$-c-Pr | 0 | SO$_2$Et | |
| 1-579 | CH$_2$O(CH$_2$)$_3$OMe | (CH$_2$)$_2$OMe | 0 | SO$_2$Et | |
| 1-580 | CH$_2$O(CH$_2$)$_3$OMe | (CH$_2$)$_3$OMe | 0 | SO$_2$Et | |
| 1-581 | CH$_2$O(CH$_2$)$_3$OMe | (CH$_2$)$_2$OEt | 0 | SO$_2$Et | |
| 1-582 | CH$_2$O(CH$_2$)$_3$OMe | (CH$_2$)$_2$OCH$_2$-c-Pr | 0 | SO$_2$Et | |
| 1-583 | CH$_2$O(CH$_2$)$_3$OMe | c-Pr | 1 | SO$_2$Et | |
| 1-584 | CH$_2$O(CH$_2$)$_3$OMe | CH$_2$-c-Pr | 1 | SO$_2$Et | |
| 1-585 | CH$_2$O(CH$_2$)$_3$OMe | (CH$_2$)$_2$OMe | 1 | SO$_2$Et | |
| 1-586 | CH$_2$O(CH$_2$)$_3$OMe | (CH$_2$)$_3$OMe | 1 | SO$_2$Et | |
| 1-587 | CH$_2$O(CH$_2$)$_3$OMe | (CH$_2$)$_2$OEt | 1 | SO$_2$Et | |
| 1-588 | CH$_2$O(CH$_2$)$_3$OMe | (CH$_2$)$_2$OCH$_2$-c-Pr | 1 | SO$_2$Et | |
| 1-589 | CH$_2$O(CH$_2$)$_3$OMe | c-Pr | 2 | SO$_2$Et | |
| 1-590 | CH$_2$O(CH$_2$)$_3$OMe | CH$_2$-c-Pr | 2 | SO$_2$Et | |

TABLE A-continued

Compounds according to the invention of the general formula (I) in which $R^1$ is methyl, $R^4$ is hydrogen and q is zero

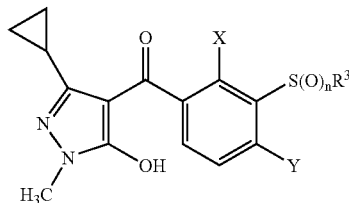

| No. | X | $R^3$ | n | Y | Physical data: $^1$H-NMR: δ[CDCl$_3$] |
|---|---|---|---|---|---|
| 1-591 | CH$_2$O(CH$_2$)$_3$OMe | (CH$_2$)$_2$OMe | 2 | SO$_2$Et | |
| 1-592 | CH$_2$O(CH$_2$)$_3$OMe | (CH$_2$)$_3$OMe | 2 | SO$_2$Et | |
| 1-593 | CH$_2$O(CH$_2$)$_3$OMe | (CH$_2$)$_2$OEt | 2 | SO$_2$Et | |
| 1-594 | CH$_2$O(CH$_2$)$_3$OMe | (CH$_2$)$_2$OCH$_2$-c-Pr | 2 | SO$_2$Et | |
| 1-595 | CH$_2$OCH$_2$OMe | c-Pr | 0 | SO$_2$Et | |
| 1-596 | CH$_2$OCH$_2$OMe | CH$_2$-c-Pr | 0 | SO$_2$Et | |
| 1-597 | CH$_2$OCH$_2$OMe | (CH$_2$)$_2$OMe | 0 | SO$_2$Et | |
| 1-598 | CH$_2$OCH$_2$OMe | (CH$_2$)$_3$OMe | 0 | SO$_2$Et | |
| 1-599 | CH$_2$OCH$_2$OMe | (CH$_2$)$_2$OEt | 0 | SO$_2$Et | |
| 1-600 | CH$_2$OCH$_2$OMe | (CH$_2$)$_2$OCH$_2$-c-Pr | 0 | SO$_2$Et | |
| 1-601 | CH$_2$OCH$_2$OMe | c-Pr | 1 | SO$_2$Et | |
| 1-602 | CH$_2$OCH$_2$OMe | CH$_2$-c-Pr | 1 | SO$_2$Et | |
| 1-603 | CH$_2$OCH$_2$OMe | (CH$_2$)$_2$OMe | 1 | SO$_2$Et | |
| 1-604 | CH$_2$OCH$_2$OMe | (CH$_2$)$_3$OMe | 1 | SO$_2$Et | |
| 1-605 | CH$_2$OCH$_2$OMe | (CH$_2$)$_2$OEt | 1 | SO$_2$Et | |
| 1-606 | CH$_2$OCH$_2$OMe | (CH$_2$)$_2$OCH$_2$-c-Pr | 1 | SO$_2$Et | |
| 1-607 | CH$_2$OCH$_2$OMe | c-Pr | 2 | SO$_2$Et | |
| 1-608 | CH$_2$OCH$_2$OMe | CH$_2$-c-Pr | 2 | SO$_2$Et | |
| 1-609 | CH$_2$OCH$_2$OMe | (CH$_2$)$_2$OMe | 2 | SO$_2$Et | |
| 1-610 | CH$_2$OCH$_2$OMe | (CH$_2$)$_3$OMe | 2 | SO$_2$Et | |
| 1-611 | CH$_2$OCH$_2$OMe | (CH$_2$)$_2$OEt | 2 | SO$_2$Et | |
| 1-612 | CH$_2$OCH$_2$OMe | (CH$_2$)$_2$OCH$_2$-c-Pr | 2 | SO$_2$Et | |
| 1-613 | CH$_2$OCH$_2$OEt | c-Pr | 0 | SO$_2$Et | |
| 1-614 | CH$_2$OCH$_2$OEt | CH$_2$-c-Pr | 0 | SO$_2$Et | |
| 1-615 | CH$_2$OCH$_2$OEt | (CH$_2$)$_2$OMe | 0 | SO$_2$Et | |
| 1-616 | CH$_2$OCH$_2$OEt | (CH$_2$)$_3$OMe | 0 | SO$_2$Et | |
| 1-617 | CH$_2$OCH$_2$OEt | (CH$_2$)$_2$OEt | 0 | SO$_2$Et | |
| 1-618 | CH$_2$OCH$_2$OEt | (CH$_2$)$_2$OCH$_2$-c-Pr | 0 | SO$_2$Et | |
| 1-619 | CH$_2$OCH$_2$OEt | c-Pr | 1 | SO$_2$Et | |
| 1-620 | CH$_2$OCH$_2$OEt | CH$_2$-c-Pr | 1 | SO$_2$Et | |
| 1-621 | CH$_2$OCH$_2$OEt | (CH$_2$)$_2$OMe | 1 | SO$_2$Et | |
| 1-622 | CH$_2$OCH$_2$OEt | (CH$_2$)$_3$OMe | 1 | SO$_2$Et | |
| 1-623 | CH$_2$OCH$_2$OEt | (CH$_2$)$_2$OEt | 1 | SO$_2$Et | |
| 1-624 | CH$_2$OCH$_2$OEt | (CH$_2$)$_2$OCH$_2$-c-Pr | 1 | SO$_2$Et | |
| 1-625 | CH$_2$OCH$_2$OEt | c-Pr | 2 | SO$_2$Et | |
| 1-626 | CH$_2$OCH$_2$OEt | CH$_2$-c-Pr | 2 | SO$_2$Et | |
| 1-627 | CH$_2$OCH$_2$OEt | (CH$_2$)$_2$OMe | 2 | SO$_2$Et | |
| 1-628 | CH$_2$OCH$_2$OEt | (CH$_2$)$_3$OMe | 2 | SO$_2$Et | |
| 1-629 | CH$_2$OCH$_2$OEt | (CH$_2$)$_2$OEt | 2 | SO$_2$Et | |
| 1-630 | CH$_2$OCH$_2$OEt | (CH$_2$)$_2$OCH$_2$-c-Pr | 2 | SO$_2$Et | |
| 1-631 | CH$_2$O(CH$_2$)$_2$SO$_2$Me | c-Pr | 0 | SO$_2$Et | |
| 1-632 | CH$_2$O(CH$_2$)$_2$SO$_2$Me | CH$_2$-c-Pr | 0 | SO$_2$Et | |
| 1-633 | CH$_2$O(CH$_2$)$_2$SO$_2$Me | (CH$_2$)$_2$OMe | 0 | SO$_2$Et | |
| 1-634 | CH$_2$O(CH$_2$)$_2$SO$_2$Me | (CH$_2$)$_3$OMe | 0 | SO$_2$Et | |
| 1-635 | CH$_2$O(CH$_2$)$_2$SO$_2$Me | (CH$_2$)$_2$OEt | 0 | SO$_2$Et | |
| 1-636 | CH$_2$O(CH$_2$)$_2$SO$_2$Me | (CH$_2$)$_2$OCH$_2$-c-Pr | 0 | SO$_2$Et | |
| 1-637 | CH$_2$O(CH$_2$)$_2$SO$_2$Me | c-Pr | 1 | SO$_2$Et | |
| 1-638 | CH$_2$O(CH$_2$)$_2$SO$_2$Me | CH$_2$-c-Pr | 1 | SO$_2$Et | |
| 1-639 | CH$_2$O(CH$_2$)$_2$SO$_2$Me | (CH$_2$)$_2$OMe | 1 | SO$_2$Et | |
| 1-640 | CH$_2$O(CH$_2$)$_2$SO$_2$Me | (CH$_2$)$_3$OMe | 1 | SO$_2$Et | |
| 1-641 | CH$_2$O(CH$_2$)$_2$SO$_2$Me | (CH$_2$)$_2$OEt | 1 | SO$_2$Et | |
| 1-642 | CH$_2$O(CH$_2$)$_2$SO$_2$Me | (CH$_2$)$_2$OCH$_2$-c-Pr | 1 | SO$_2$Et | |
| 1-643 | CH$_2$O(CH$_2$)$_2$SO$_2$Me | c-Pr | 2 | SO$_2$Et | |
| 1-644 | CH$_2$O(CH$_2$)$_2$SO$_2$Me | CH$_2$-c-Pr | 2 | SO$_2$Et | |
| 1-645 | CH$_2$O(CH$_2$)$_2$SO$_2$Me | (CH$_2$)$_2$OMe | 2 | SO$_2$Et | |
| 1-646 | CH$_2$O(CH$_2$)$_2$SO$_2$Me | (CH$_2$)$_3$OMe | 2 | SO$_2$Et | |
| 1-647 | CH$_2$O(CH$_2$)$_2$SO$_2$Me | (CH$_2$)$_2$OEt | 2 | SO$_2$Et | |
| 1-648 | CH$_2$O(CH$_2$)$_2$SO$_2$Me | (CH$_2$)$_2$OCH$_2$-c-Pr | 2 | SO$_2$Et | |
| 1-649 | CH$_2$SO$_2$(CH$_2$)$_2$OMe | c-Pr | 0 | SO$_2$Et | |
| 1-650 | CH$_2$SO$_2$(CH$_2$)$_2$OMe | CH$_2$-c-Pr | 0 | SO$_2$Et | |
| 1-651 | CH$_2$SO$_2$(CH$_2$)$_2$OMe | (CH$_2$)$_2$OMe | 0 | SO$_2$Et | |
| 1-652 | CH$_2$SO$_2$(CH$_2$)$_2$OMe | (CH$_2$)$_3$OMe | 0 | SO$_2$Et | |
| 1-653 | CH$_2$SO$_2$(CH$_2$)$_2$OMe | (CH$_2$)$_2$OEt | 0 | SO$_2$Et | |

TABLE A-continued

Compounds according to the invention of the general formula (I) in which $R^1$ is methyl, $R^4$ is hydrogen and q is zero

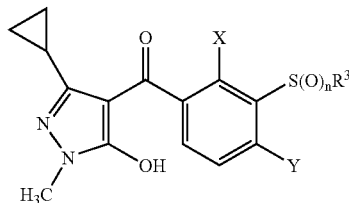

| No. | X | $R^3$ | n | Y | Physical data: $^1$H-NMR: δ[CDCl$_3$] |
|---|---|---|---|---|---|
| 1-654 | CH$_2$SO$_2$(CH$_2$)$_2$OMe | (CH$_2$)$_2$OCH$_2$-c-Pr | 0 | SO$_2$Et | |
| 1-655 | CH$_2$SO$_2$(CH$_2$)$_2$OMe | c-Pr | 1 | SO$_2$Et | |
| 1-656 | CH$_2$SO$_2$(CH$_2$)$_2$OMe | CH$_2$-c-Pr | 1 | SO$_2$Et | |
| 1-657 | CH$_2$SO$_2$(CH$_2$)$_2$OMe | (CH$_2$)$_2$OMe | 1 | SO$_2$Et | |
| 1-658 | CH$_2$SO$_2$(CH$_2$)$_2$OMe | (CH$_2$)$_3$OMe | 1 | SO$_2$Et | |
| 1-659 | CH$_2$SO$_2$(CH$_2$)$_2$OMe | (CH$_2$)$_2$OEt | 1 | SO$_2$Et | |
| 1-660 | CH$_2$SO$_2$(CH$_2$)$_2$OMe | (CH$_2$)$_2$OCH$_2$-c-Pr | 1 | SO$_2$Et | |
| 1-661 | CH$_2$SO$_2$(CH$_2$)$_2$OMe | c-Pr | 2 | SO$_2$Et | |
| 1-662 | CH$_2$SO$_2$(CH$_2$)$_2$OMe | CH$_2$-c-Pr | 2 | SO$_2$Et | |
| 1-663 | CH$_2$SO$_2$(CH$_2$)$_2$OMe | (CH$_2$)$_2$OMe | 2 | SO$_2$Et | |
| 1-664 | CH$_2$SO$_2$(CH$_2$)$_2$OMe | (CH$_2$)$_3$OMe | 2 | SO$_2$Et | |
| 1-665 | CH$_2$SO$_2$(CH$_2$)$_2$OMe | (CH$_2$)$_2$OEt | 2 | SO$_2$Et | |
| 1-666 | CH$_2$SO$_2$(CH$_2$)$_2$OMe | (CH$_2$)$_2$OCH$_2$-c-Pr | 2 | SO$_2$Et | |
| 1-667 | CH$_2$SO$_2$(CH$_2$)$_2$SO$_2$Me | c-Pr | 0 | SO$_2$Et | |
| 1-668 | CH$_2$SO$_2$(CH$_2$)$_2$SO$_2$Me | CH$_2$-c-Pr | 0 | SO$_2$Et | |
| 1-669 | CH$_2$SO$_2$(CH$_2$)$_2$SO$_2$Me | (CH$_2$)$_2$OMe | 0 | SO$_2$Et | |
| 1-670 | CH$_2$SO$_2$(CH$_2$)$_2$SO$_2$Me | (CH$_2$)$_3$OMe | 0 | SO$_2$Et | |
| 1-671 | CH$_2$SO$_2$(CH$_2$)$_2$SO$_2$Me | (CH$_2$)$_2$OEt | 0 | SO$_2$Et | |
| 1-672 | CH$_2$SO$_2$(CH$_2$)$_2$SO$_2$Me | (CH$_2$)$_2$OCH$_2$-c-Pr | 0 | SO$_2$Et | |
| 1-673 | CH$_2$SO$_2$(CH$_2$)$_2$SO$_2$Me | c-Pr | 1 | SO$_2$Et | |
| 1-674 | CH$_2$SO$_2$(CH$_2$)$_2$SO$_2$Me | CH$_2$-c-Pr | 1 | SO$_2$Et | |
| 1-675 | CH$_2$SO$_2$(CH$_2$)$_2$SO$_2$Me | (CH$_2$)$_2$OMe | 1 | SO$_2$Et | |
| 1-676 | CH$_2$SO$_2$(CH$_2$)$_2$SO$_2$Me | (CH$_2$)$_3$OMe | 1 | SO$_2$Et | |
| 1-677 | CH$_2$SO$_2$(CH$_2$)$_2$SO$_2$Me | (CH$_2$)$_2$OEt | 1 | SO$_2$Et | |
| 1-678 | CH$_2$SO$_2$(CH$_2$)$_2$SO$_2$Me | (CH$_2$)$_2$OCH$_2$-c-Pr | 1 | SO$_2$Et | |
| 1-679 | CH$_2$SO$_2$(CH$_2$)$_2$SO$_2$Me | c-Pr | 2 | SO$_2$Et | |
| 1-680 | CH$_2$SO$_2$(CH$_2$)$_2$SO$_2$Me | CH$_2$-c-Pr | 2 | SO$_2$Et | |
| 1-681 | CH$_2$SO$_2$(CH$_2$)$_2$SO$_2$Me | (CH$_2$)$_2$OMe | 2 | SO$_2$Et | |
| 1-682 | CH$_2$SO$_2$(CH$_2$)$_2$SO$_2$Me | (CH$_2$)$_3$OMe | 2 | SO$_2$Et | |
| 1-683 | CH$_2$SO$_2$(CH$_2$)$_2$SO$_2$Me | (CH$_2$)$_2$OEt | 2 | SO$_2$Et | |
| 1-684 | CH$_2$SO$_2$(CH$_2$)$_2$SO$_2$Me | (CH$_2$)$_2$OCH$_2$-c-Pr | 2 | SO$_2$Et | |
| 1-685 | Cl | c-Pr | 0 | OMe | |
| 1-686 | Cl | CH$_2$-c-Pr | 0 | OMe | |
| 1-687 | Cl | (CH$_2$)$_2$OMe | 0 | OMe | |
| 1-688 | Cl | (CH$_2$)$_3$OMe | 0 | OMe | |
| 1-689 | Cl | (CH$_2$)$_2$OEt | 0 | OMe | |
| 1-690 | Cl | (CH$_2$)$_2$OCH$_2$-c-Pr | 0 | OMe | |
| 1-691 | Cl | c-Pr | 1 | OMe | |
| 1-692 | Cl | CH$_2$-c-Pr | 1 | OMe | |
| 1-693 | Cl | (CH$_2$)$_2$OMe | 1 | OMe | |
| 1-694 | Cl | (CH$_2$)$_3$OMe | 1 | OMe | |
| 1-695 | Cl | (CH$_2$)$_2$OEt | 1 | OMe | |
| 1-696 | Cl | (CH$_2$)$_2$OCH$_2$-c-Pr | 1 | OMe | |
| 1-697 | Cl | c-Pr | 2 | OMe | |
| 1-698 | Cl | CH$_2$-c-Pr | 2 | OMe | |
| 1-699 | Cl | (CH$_2$)$_2$OMe | 2 | OMe | |
| 1-700 | Cl | (CH$_2$)$_3$OMe | 2 | OMe | |
| 1-701 | Cl | (CH$_2$)$_2$OEt | 2 | OMe | |
| 1-702 | Cl | (CH$_2$)$_2$OCH$_2$-c-Pr | 2 | OMe | |
| 1-703 | Br | c-Pr | 0 | OMe | |
| 1-704 | Br | CH$_2$-c-Pr | 0 | OMe | |
| 1-705 | Br | (CH$_2$)$_2$OMe | 0 | OMe | |
| 1-706 | Br | (CH$_2$)$_3$OMe | 0 | OMe | |
| 1-707 | Br | (CH$_2$)$_2$OEt | 0 | OMe | |
| 1-708 | Br | (CH$_2$)$_2$OCH$_2$-c-Pr | 0 | OMe | |
| 1-709 | Br | c-Pr | 1 | OMe | |
| 1-710 | Br | CH$_2$-c-Pr | 1 | OMe | |
| 1-711 | Br | (CH$_2$)$_2$OMe | 1 | OMe | |
| 1-712 | Br | (CH$_2$)$_3$OMe | 1 | OMe | |
| 1-713 | Br | (CH$_2$)$_2$OEt | 1 | OMe | |
| 1-714 | Br | (CH$_2$)$_2$OCH$_2$-c-Pr | 1 | OMe | |
| 1-715 | Br | c-Pr | 2 | OMe | |
| 1-716 | Br | CH$_2$-c-Pr | 2 | OMe | |

TABLE A-continued

Compounds according to the invention of the general formula (I) in which $R^1$ is methyl, $R^4$ is hydrogen and q is zero

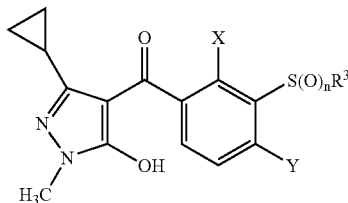

| No. | X | $R^3$ | n | Y | Physical data: $^1$H-NMR: δ[CDCl$_3$] |
|---|---|---|---|---|---|
| 1-717 | Br | (CH$_2$)$_2$OMe | 2 | OMe | |
| 1-718 | Br | (CH$_2$)$_3$OMe | 2 | OMe | |
| 1-719 | Br | (CH$_2$)$_2$OEt | 2 | OMe | |
| 1-720 | Br | (CH$_2$)$_2$OCH$_2$-c-Pr | 2 | OMe | |
| 1-721 | Me | c-Pr | 0 | OMe | |
| 1-722 | Me | CH$_2$-c-Pr | 0 | OMe | |
| 1-723 | Me | (CH$_2$)$_2$OMe | 0 | OMe | |
| 1-724 | Me | (CH$_2$)$_3$OMe | 0 | OMe | |
| 1-725 | Me | (CH$_2$)$_2$OEt | 0 | OMe | |
| 1-726 | Me | (CH$_2$)$_2$OCH$_2$-c-Pr | 0 | OMe | |
| 1-727 | Me | c-Pr | 1 | OMe | |
| 1-728 | Me | CH$_2$-c-Pr | 1 | OMe | |
| 1-729 | Me | (CH$_2$)$_2$OMe | 1 | OMe | |
| 1-730 | Me | (CH$_2$)$_3$OMe | 1 | OMe | |
| 1-731 | Me | (CH$_2$)$_2$OEt | 1 | OMe | |
| 1-732 | Me | (CH$_2$)$_2$OCH$_2$-c-Pr | 1 | OMe | |
| 1-733 | Me | c-Pr | 2 | OMe | |
| 1-734 | Me | CH$_2$-c-Pr | 2 | OMe | |
| 1-735 | Me | (CH$_2$)$_2$OMe | 2 | OMe | |
| 1-736 | Me | (CH$_2$)$_3$OMe | 2 | OMe | |
| 1-737 | Me | (CH$_2$)$_2$OEt | 2 | OMe | |
| 1-738 | Me | (CH$_2$)$_2$OCH$_2$-c-Pr | 2 | OMe | |
| 1-739 | Et | c-Pr | 0 | OMe | |
| 1-740 | Et | CH$_2$-c-Pr | 0 | OMe | |
| 1-741 | Et | (CH$_2$)$_2$OMe | 0 | OMe | |
| 1-742 | Et | (CH$_2$)$_3$OMe | 0 | OMe | |
| 1-743 | Et | (CH$_2$)$_2$OEt | 0 | OMe | |
| 1-744 | Et | (CH$_2$)$_2$OCH$_2$-c-Pr | 0 | OMe | |
| 1-745 | Et | c-Pr | 1 | OMe | |
| 1-746 | Et | CH$_2$-c-Pr | 1 | OMe | |
| 1-747 | Et | (CH$_2$)$_2$OMe | 1 | OMe | |
| 1-748 | Et | (CH$_2$)$_3$OMe | 1 | OMe | |
| 1-749 | Et | (CH$_2$)$_2$OEt | 1 | OMe | |
| 1-750 | Et | (CH$_2$)$_2$OCH$_2$-c-Pr | 1 | OMe | |
| 1-751 | Et | c-Pr | 2 | OMe | |
| 1-752 | Et | CH$_2$-c-Pr | 2 | OMe | |
| 1-753 | Et | (CH$_2$)$_2$OMe | 2 | OMe | |
| 1-754 | Et | (CH$_2$)$_3$OMe | 2 | OMe | |
| 1-755 | Et | (CH$_2$)$_2$OEt | 2 | OMe | |
| 1-756 | Et | (CH$_2$)$_2$OCH$_2$-c-Pr | 2 | OMe | |
| 1-757 | CF$_3$ | c-Pr | 0 | OMe | |
| 1-758 | CF$_3$ | CH$_2$-c-Pr | 0 | OMe | |
| 1-759 | CF$_3$ | (CH$_2$)$_2$OMe | 0 | OMe | |
| 1-760 | CF$_3$ | (CH$_2$)$_3$OMe | 0 | OMe | |
| 1-761 | CF$_3$ | (CH$_2$)$_2$OEt | 0 | OMe | |
| 1-762 | CF$_3$ | (CH$_2$)$_2$OCH$_2$-c-Pr | 0 | OMe | |
| 1-763 | CF$_3$ | c-Pr | 1 | OMe | |
| 1-764 | CF$_3$ | CH$_2$-c-Pr | 1 | OMe | |
| 1-765 | CF$_3$ | (CH$_2$)$_2$OMe | 1 | OMe | |
| 1-766 | CF$_3$ | (CH$_2$)$_3$OMe | 1 | OMe | |
| 1-767 | CF$_3$ | (CH$_2$)$_2$OEt | 1 | OMe | |
| 1-768 | CF$_3$ | (CH$_2$)$_2$OCH$_2$-c-Pr | 1 | OMe | |
| 1-769 | CF$_3$ | c-Pr | 2 | OMe | |
| 1-770 | CF$_3$ | CH$_2$-c-Pr | 2 | OMe | |
| 1-771 | CF$_3$ | (CH$_2$)$_2$OMe | 2 | OMe | |
| 1-772 | CF$_3$ | (CH$_2$)$_3$OMe | 2 | OMe | |
| 1-773 | CF$_3$ | (CH$_2$)$_2$OEt | 2 | OMe | |
| 1-774 | CF$_3$ | (CH$_2$)$_2$OCH$_2$-c-Pr | 2 | OMe | |
| 1-775 | OMe | c-Pr | 0 | OMe | |
| 1-776 | OMe | CH$_2$-c-Pr | 0 | OMe | |
| 1-777 | OMe | (CH$_2$)$_2$OMe | 0 | OMe | |
| 1-778 | OMe | (CH$_2$)$_3$OMe | 0 | OMe | |
| 1-779 | OMe | (CH$_2$)$_2$OEt | 0 | OMe | |

TABLE A-continued

Compounds according to the invention of the general formula (I) in which $R^1$ is methyl, $R^4$ is hydrogen and q is zero

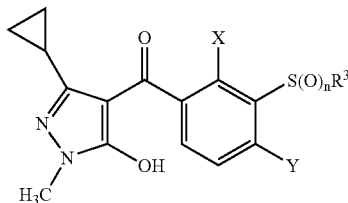

| No. | X | $R^3$ | n | Y | Physical data: $^1$H-NMR: δ[CDCl$_3$] |
|---|---|---|---|---|---|
| 1-780 | OMe | (CH$_2$)$_2$OCH$_2$-c-Pr | 0 | OMe | |
| 1-781 | OMe | c-Pr | 1 | OMe | |
| 1-782 | OMe | CH$_2$-c-Pr | 1 | OMe | |
| 1-783 | OMe | (CH$_2$)$_2$OMe | 1 | OMe | |
| 1-784 | OMe | (CH$_2$)$_3$OMe | 1 | OMe | |
| 1-785 | OMe | (CH$_2$)$_2$OEt | 1 | OMe | |
| 1-786 | OMe | (CH$_2$)$_2$OCH$_2$-c-Pr | 1 | OMe | |
| 1-787 | OMe | c-Pr | 2 | OMe | |
| 1-788 | OMe | CH$_2$-c-Pr | 2 | OMe | |
| 1-789 | OMe | (CH$_2$)$_2$OMe | 2 | OMe | |
| 1-790 | OMe | (CH$_2$)$_3$OMe | 2 | OMe | |
| 1-791 | OMe | (CH$_2$)$_2$OEt | 2 | OMe | |
| 1-792 | OMe | (CH$_2$)$_2$OCH$_2$-c-Pr | 2 | OMe | |
| 1-793 | OEt | c-Pr | 0 | OMe | |
| 1-794 | OEt | CH$_2$-c-Pr | 0 | OMe | |
| 1-795 | OEt | (CH$_2$)$_2$OMe | 0 | OMe | |
| 1-796 | OEt | (CH$_2$)$_3$OMe | 0 | OMe | |
| 1-797 | OEt | (CH$_2$)$_2$OEt | 0 | OMe | |
| 1-798 | OEt | (CH$_2$)$_2$OCH$_2$-c-Pr | 0 | OMe | |
| 1-799 | OEt | c-Pr | 1 | OMe | |
| 1-800 | OEt | CH$_2$-c-Pr | 1 | OMe | |
| 1-801 | OEt | (CH$_2$)$_2$OMe | 1 | OMe | |
| 1-802 | OEt | (CH$_2$)$_3$OMe | 1 | OMe | |
| 1-803 | OEt | (CH$_2$)$_2$OEt | 1 | OMe | |
| 1-804 | OEt | (CH$_2$)$_2$OCH$_2$-c-Pr | 1 | OMe | |
| 1-805 | OEt | c-Pr | 2 | OMe | |
| 1-806 | OEt | CH$_2$-c-Pr | 2 | OMe | |
| 1-807 | OEt | (CH$_2$)$_2$OMe | 2 | OMe | |
| 1-808 | OEt | (CH$_2$)$_3$OMe | 2 | OMe | |
| 1-809 | OEt | (CH$_2$)$_2$OEt | 2 | OMe | |
| 1-810 | OEt | (CH$_2$)$_2$OCH$_2$-c-Pr | 2 | OMe | |
| 1-811 | NO$_2$ | c-Pr | 0 | OMe | |
| 1-812 | NO$_2$ | CH$_2$-c-Pr | 0 | OMe | |
| 1-813 | NO$_2$ | (CH$_2$)$_2$OMe | 0 | OMe | |
| 1-814 | NO$_2$ | (CH$_2$)$_3$OMe | 0 | OMe | |
| 1-815 | NO$_2$ | (CH$_2$)$_2$OEt | 0 | OMe | |
| 1-816 | NO$_2$ | (CH$_2$)$_2$OCH$_2$-c-Pr | 0 | OMe | |
| 1-817 | NO$_2$ | c-Pr | 1 | OMe | |
| 1-818 | NO$_2$ | CH$_2$-c-Pr | 1 | OMe | |
| 1-819 | NO$_2$ | (CH$_2$)$_2$OMe | 1 | OMe | |
| 1-820 | NO$_2$ | (CH$_2$)$_3$OMe | 1 | OMe | |
| 1-821 | NO$_2$ | (CH$_2$)$_2$OEt | 1 | OMe | |
| 1-822 | NO$_2$ | (CH$_2$)$_2$OCH$_2$-c-Pr | 1 | OMe | |
| 1-823 | NO$_2$ | c-Pr | 2 | OMe | |
| 1-824 | NO$_2$ | CH$_2$-c-Pr | 2 | OMe | |
| 1-825 | NO$_2$ | (CH$_2$)$_2$OMe | 2 | OMe | |
| 1-826 | NO$_2$ | (CH$_2$)$_3$OMe | 2 | OMe | |
| 1-827 | NO$_2$ | (CH$_2$)$_2$OEt | 2 | OMe | |
| 1-828 | NO$_2$ | (CH$_2$)$_2$OCH$_2$-c-Pr | 2 | OMe | |
| 1-829 | SO$_2$Me | c-Pr | 0 | OMe | |
| 1-830 | SO$_2$Me | CH$_2$-c-Pr | 0 | OMe | |
| 1-831 | SO$_2$Me | (CH$_2$)$_2$OMe | 0 | OMe | |
| 1-832 | SO$_2$Me | (CH$_2$)$_3$OMe | 0 | OMe | |
| 1-833 | SO$_2$Me | (CH$_2$)$_2$OEt | 0 | OMe | |
| 1-834 | SO$_2$Me | (CH$_2$)$_2$OCH$_2$-c-Pr | 0 | OMe | |
| 1-835 | SO$_2$Me | c-Pr | 1 | OMe | |
| 1-836 | SO$_2$Me | CH$_2$-c-Pr | 1 | OMe | |
| 1-837 | SO$_2$Me | (CH$_2$)$_2$OMe | 1 | OMe | |
| 1-838 | SO$_2$Me | (CH$_2$)$_3$OMe | 1 | OMe | |
| 1-839 | SO$_2$Me | (CH$_2$)$_2$OEt | 1 | OMe | |
| 1-840 | SO$_2$Me | (CH$_2$)$_2$OCH$_2$-c-Pr | 1 | OMe | |
| 1-841 | SO$_2$Me | c-Pr | 2 | OMe | |
| 1-842 | SO$_2$Me | CH$_2$-c-Pr | 2 | OMe | |

TABLE A-continued

Compounds according to the invention of the general formula (I) in which $R^1$ is methyl, $R^4$ is hydrogen and q is zero

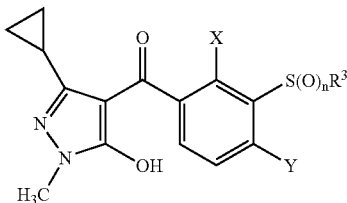

| No. | X | $R^3$ | n | Y | Physical data: $^1$H-NMR: δ[CDCl$_3$] |
|---|---|---|---|---|---|
| 1-843 | SO$_2$Me | (CH$_2$)$_2$OMe | 2 | OMe | |
| 1-844 | SO$_2$Me | (CH$_2$)$_3$OMe | 2 | OMe | |
| 1-845 | SO$_2$Me | (CH$_2$)$_2$OEt | 2 | OMe | |
| 1-846 | SO$_2$Me | (CH$_2$)$_2$OCH$_2$-c-Pr | 2 | OMe | |
| 1-847 | CH$_2$OMe | c-Pr | 0 | OMe | |
| 1-848 | CH$_2$OMe | CH$_2$-c-Pr | 0 | OMe | |
| 1-849 | CH$_2$OMe | (CH$_2$)$_2$OMe | 0 | OMe | |
| 1-850 | CH$_2$OMe | (CH$_2$)$_3$OMe | 0 | OMe | |
| 1-851 | CH$_2$OMe | (CH$_2$)$_2$OEt | 0 | OMe | |
| 1-852 | CH$_2$OMe | (CH$_2$)$_2$OCH$_2$-c-Pr | 0 | OMe | |
| 1-853 | CH$_2$OMe | c-Pr | 1 | OMe | |
| 1-854 | CH$_2$OMe | CH$_2$-c-Pr | 1 | OMe | |
| 1-855 | CH$_2$OMe | (CH$_2$)$_2$OMe | 1 | OMe | |
| 1-856 | CH$_2$OMe | (CH$_2$)$_3$OMe | 1 | OMe | |
| 1-857 | CH$_2$OMe | (CH$_2$)$_2$OEt | 1 | OMe | |
| 1-858 | CH$_2$OMe | (CH$_2$)$_2$OCH$_2$-c-Pr | 1 | OMe | |
| 1-859 | CH$_2$OMe | c-Pr | 2 | OMe | |
| 1-860 | CH$_2$OMe | CH$_2$-c-Pr | 2 | OMe | |
| 1-861 | CH$_2$OMe | (CH$_2$)$_2$OMe | 2 | OMe | |
| 1-862 | CH$_2$OMe | (CH$_2$)$_3$OMe | 2 | OMe | |
| 1-863 | CH$_2$OMe | (CH$_2$)$_2$OEt | 2 | OMe | |
| 1-864 | CH$_2$OMe | (CH$_2$)$_2$OCH$_2$-c-Pr | 2 | OMe | |
| 1-865 | CH$_2$SO$_2$Me | c-Pr | 0 | OMe | |
| 1-866 | CH$_2$SO$_2$Me | CH$_2$-c-Pr | 0 | OMe | |
| 1-867 | CH$_2$SO$_2$Me | (CH$_2$)$_2$OMe | 0 | OMe | |
| 1-868 | CH$_2$SO$_2$Me | (CH$_2$)$_3$OMe | 0 | OMe | |
| 1-869 | CH$_2$SO$_2$Me | (CH$_2$)$_2$OEt | 0 | OMe | |
| 1-870 | CH$_2$SO$_2$Me | (CH$_2$)$_2$OCH$_2$-c-Pr | 0 | OMe | |
| 1-871 | CH$_2$SO$_2$Me | c-Pr | 1 | OMe | |
| 1-872 | CH$_2$SO$_2$Me | CH$_2$-c-Pr | 1 | OMe | |
| 1-873 | CH$_2$SO$_2$Me | (CH$_2$)$_2$OMe | 1 | OMe | |
| 1-874 | CH$_2$SO$_2$Me | (CH$_2$)$_3$OMe | 1 | OMe | |
| 1-875 | CH$_2$SO$_2$Me | (CH$_2$)$_2$OEt | 1 | OMe | |
| 1-876 | CH$_2$SO$_2$Me | (CH$_2$)$_2$OCH$_2$-c-Pr | 1 | OMe | |
| 1-877 | CH$_2$SO$_2$Me | c-Pr | 2 | OMe | |
| 1-878 | CH$_2$SO$_2$Me | CH$_2$-c-Pr | 2 | OMe | |
| 1-879 | CH$_2$SO$_2$Me | (CH$_2$)$_2$OMe | 2 | OMe | |
| 1-880 | CH$_2$SO$_2$Me | (CH$_2$)$_3$OMe | 2 | OMe | |
| 1-881 | CH$_2$SO$_2$Me | (CH$_2$)$_2$OEt | 2 | OMe | |
| 1-882 | CH$_2$SO$_2$Me | (CH$_2$)$_2$OCH$_2$-c-Pr | 2 | OMe | |
| 1-883 | CH$_2$O(CH$_2$)$_2$OMe | c-Pr | 0 | OMe | |
| 1-884 | CH$_2$O(CH$_2$)$_2$OMe | CH$_2$-c-Pr | 0 | OMe | |
| 1-885 | CH$_2$O(CH$_2$)$_2$OMe | (CH$_2$)$_2$OMe | 0 | OMe | |
| 1-886 | CH$_2$O(CH$_2$)$_2$OMe | (CH$_2$)$_3$OMe | 0 | OMe | |
| 1-887 | CH$_2$O(CH$_2$)$_2$OMe | (CH$_2$)$_2$OEt | 0 | OMe | |
| 1-888 | CH$_2$O(CH$_2$)$_2$OMe | (CH$_2$)$_2$OCH$_2$-c-Pr | 0 | OMe | |
| 1-889 | CH$_2$O(CH$_2$)$_2$OMe | c-Pr | 1 | OMe | |
| 1-890 | CH$_2$O(CH$_2$)$_2$OMe | CH$_2$-c-Pr | 1 | OMe | |
| 1-891 | CH$_2$O(CH$_2$)$_2$OMe | (CH$_2$)$_2$OMe | 1 | OMe | |
| 1-892 | CH$_2$O(CH$_2$)$_2$OMe | (CH$_2$)$_3$OMe | 1 | OMe | |
| 1-893 | CH$_2$O(CH$_2$)$_2$OMe | (CH$_2$)$_2$OEt | 1 | OMe | |
| 1-894 | CH$_2$O(CH$_2$)$_2$OMe | (CH$_2$)$_2$OCH$_2$-c-Pr | 1 | OMe | |
| 1-895 | CH$_2$O(CH$_2$)$_2$OMe | c-Pr | 2 | OMe | |
| 1-896 | CH$_2$O(CH$_2$)$_2$OMe | CH$_2$-c-Pr | 2 | OMe | |
| 1-897 | CH$_2$O(CH$_2$)$_2$OMe | (CH$_2$)$_2$OMe | 2 | OMe | |
| 1-898 | CH$_2$O(CH$_2$)$_2$OMe | (CH$_2$)$_3$OMe | 2 | OMe | |
| 1-899 | CH$_2$O(CH$_2$)$_2$OMe | (CH$_2$)$_2$OEt | 2 | OMe | |
| 1-900 | CH$_2$O(CH$_2$)$_2$OMe | (CH$_2$)$_2$OCH$_2$-c-Pr | 2 | OMe | |
| 1-901 | CH$_2$O(CH$_2$)$_2$OEt | c-Pr | 0 | OMe | |
| 1-902 | CH$_2$O(CH$_2$)$_2$OEt | CH$_2$-c-Pr | 0 | OMe | |
| 1-903 | CH$_2$O(CH$_2$)$_2$OEt | (CH$_2$)$_2$OMe | 0 | OMe | |
| 1-904 | CH$_2$O(CH$_2$)$_2$OEt | (CH$_2$)$_3$OMe | 0 | OMe | |
| 1-905 | CH$_2$O(CH$_2$)$_2$OEt | (CH$_2$)$_2$OEt | 0 | OMe | |

TABLE A-continued

Compounds according to the invention of the general formula (I) in which $R^1$ is methyl, $R^4$ is hydrogen and q is zero

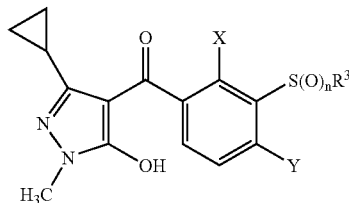

| No. | X | $R^3$ | n | Y | Physical data: $^1$H-NMR: δ[CDCl$_3$] |
|---|---|---|---|---|---|
| 1-906 | CH$_2$O(CH$_2$)$_2$OEt | (CH$_2$)$_2$OCH$_2$-c-Pr | 0 | OMe | |
| 1-907 | CH$_2$O(CH$_2$)$_2$OEt | c-Pr | 1 | OMe | |
| 1-908 | CH$_2$O(CH$_2$)$_2$OEt | CH$_2$-c-Pr | 1 | OMe | |
| 1-909 | CH$_2$O(CH$_2$)$_2$OEt | (CH$_2$)$_2$OMe | 1 | OMe | |
| 1-910 | CH$_2$O(CH$_2$)$_2$OEt | (CH$_2$)$_3$OMe | 1 | OMe | |
| 1-911 | CH$_2$O(CH$_2$)$_2$OEt | (CH$_2$)$_2$OEt | 1 | OMe | |
| 1-912 | CH$_2$O(CH$_2$)$_2$OEt | (CH$_2$)$_2$OCH$_2$-c-Pr | 1 | OMe | |
| 1-913 | CH$_2$O(CH$_2$)$_2$OEt | c-Pr | 2 | OMe | |
| 1-914 | CH$_2$O(CH$_2$)$_2$OEt | CH$_2$-c-Pr | 2 | OMe | |
| 1-915 | CH$_2$O(CH$_2$)$_2$OEt | (CH$_2$)$_2$OMe | 2 | OMe | |
| 1-916 | CH$_2$O(CH$_2$)$_2$OEt | (CH$_2$)$_3$OMe | 2 | OMe | |
| 1-917 | CH$_2$O(CH$_2$)$_2$OEt | (CH$_2$)$_2$OEt | 2 | OMe | |
| 1-918 | CH$_2$O(CH$_2$)$_2$OEt | (CH$_2$)$_2$OCH$_2$-c-Pr | 2 | OMe | |
| 1-919 | CH$_2$O(CH$_2$)$_3$OMe | c-Pr | 0 | OMe | |
| 1-920 | CH$_2$O(CH$_2$)$_3$OMe | CH$_2$-c-Pr | 0 | OMe | |
| 1-921 | CH$_2$O(CH$_2$)$_3$OMe | (CH$_2$)$_2$OMe | 0 | OMe | |
| 1-922 | CH$_2$O(CH$_2$)$_3$OMe | (CH$_2$)$_3$OMe | 0 | OMe | |
| 1-923 | CH$_2$O(CH$_2$)$_3$OMe | (CH$_2$)$_2$OEt | 0 | OMe | |
| 1-924 | CH$_2$O(CH$_2$)$_3$OMe | (CH$_2$)$_2$OCH$_2$-c-Pr | 0 | OMe | |
| 1-925 | CH$_2$O(CH$_2$)$_3$OMe | c-Pr | 1 | OMe | |
| 1-926 | CH$_2$O(CH$_2$)$_3$OMe | CH$_2$-c-Pr | 1 | OMe | |
| 1-927 | CH$_2$O(CH$_2$)$_3$OMe | (CH$_2$)$_2$OMe | 1 | OMe | |
| 1-928 | CH$_2$O(CH$_2$)$_3$OMe | (CH$_2$)$_3$OMe | 1 | OMe | |
| 1-929 | CH$_2$O(CH$_2$)$_3$OMe | (CH$_2$)$_2$OEt | 1 | OMe | |
| 1-930 | CH$_2$O(CH$_2$)$_3$OMe | (CH$_2$)$_2$OCH$_2$-c-Pr | 1 | OMe | |
| 1-931 | CH$_2$O(CH$_2$)$_3$OMe | c-Pr | 2 | OMe | |
| 1-932 | CH$_2$O(CH$_2$)$_3$OMe | CH$_2$-c-Pr | 2 | OMe | |
| 1-933 | CH$_2$O(CH$_2$)$_3$OMe | (CH$_2$)$_2$OMe | 2 | OMe | |
| 1-934 | CH$_2$O(CH$_2$)$_3$OMe | (CH$_2$)$_3$OMe | 2 | OMe | |
| 1-935 | CH$_2$O(CH$_2$)$_3$OMe | (CH$_2$)$_2$OEt | 2 | OMe | |
| 1-936 | CH$_2$O(CH$_2$)$_3$OMe | (CH$_2$)$_2$OCH$_2$-c-Pr | 2 | OMe | |
| 1-937 | CH$_2$OCH$_2$OMe | c-Pr | 0 | OMe | |
| 1-938 | CH$_2$OCH$_2$OMe | CH$_2$-c-Pr | 0 | OMe | |
| 1-939 | CH$_2$OCH$_2$OMe | (CH$_2$)$_2$OMe | 0 | OMe | |
| 1-940 | CH$_2$OCH$_2$OMe | (CH$_2$)$_3$OMe | 0 | OMe | |
| 1-941 | CH$_2$OCH$_2$OMe | (CH$_2$)$_2$OEt | 0 | OMe | |
| 1-942 | CH$_2$OCH$_2$OMe | (CH$_2$)$_2$OCH$_2$-c-Pr | 0 | OMe | |
| 1-943 | CH$_2$OCH$_2$OMe | c-Pr | 1 | OMe | |
| 1-944 | CH$_2$OCH$_2$OMe | CH$_2$-c-Pr | 1 | OMe | |
| 1-945 | CH$_2$OCH$_2$OMe | (CH$_2$)$_2$OMe | 1 | OMe | |
| 1-946 | CH$_2$OCH$_2$OMe | (CH$_2$)$_3$OMe | 1 | OMe | |
| 1-947 | CH$_2$OCH$_2$OMe | (CH$_2$)$_2$OEt | 1 | OMe | |
| 1-948 | CH$_2$OCH$_2$OMe | (CH$_2$)$_2$OCH$_2$-c-Pr | 1 | OMe | |
| 1-949 | CH$_2$OCH$_2$OMe | c-Pr | 2 | OMe | |
| 1-950 | CH$_2$OCH$_2$OMe | CH$_2$-c-Pr | 2 | OMe | |
| 1-951 | CH$_2$OCH$_2$OMe | (CH$_2$)$_2$OMe | 2 | OMe | |
| 1-952 | CH$_2$OCH$_2$OMe | (CH$_2$)$_3$OMe | 2 | OMe | |
| 1-953 | CH$_2$OCH$_2$OMe | (CH$_2$)$_2$OEt | 2 | OMe | |
| 1-954 | CH$_2$OCH$_2$OMe | (CH$_2$)$_2$OCH$_2$-c-Pr | 2 | OMe | |
| 1-955 | CH$_2$OCH$_2$OEt | c-Pr | 0 | OMe | |
| 1-956 | CH$_2$OCH$_2$OEt | CH$_2$-c-Pr | 0 | OMe | |
| 1-957 | CH$_2$OCH$_2$OEt | (CH$_2$)$_2$OMe | 0 | OMe | |
| 1-958 | CH$_2$OCH$_2$OEt | (CH$_2$)$_3$OMe | 0 | OMe | |
| 1-959 | CH$_2$OCH$_2$OEt | (CH$_2$)$_2$OEt | 0 | OMe | |
| 1-960 | CH$_2$OCH$_2$OEt | (CH$_2$)$_2$OCH$_2$-c-Pr | 0 | OMe | |
| 1-961 | CH$_2$OCH$_2$OEt | c-Pr | 1 | OMe | |
| 1-962 | CH$_2$OCH$_2$OEt | CH$_2$-c-Pr | 1 | OMe | |
| 1-963 | CH$_2$OCH$_2$OEt | (CH$_2$)$_2$OMe | 1 | OMe | |
| 1-964 | CH$_2$OCH$_2$OEt | (CH$_2$)$_3$OMe | 1 | OMe | |
| 1-965 | CH$_2$OCH$_2$OEt | (CH$_2$)$_2$OEt | 1 | OMe | |
| 1-966 | CH$_2$OCH$_2$OEt | (CH$_2$)$_2$OCH$_2$-c-Pr | 1 | OMe | |
| 1-967 | CH$_2$OCH$_2$OEt | c-Pr | 2 | OMe | |
| 1-968 | CH$_2$OCH$_2$OEt | CH$_2$-c-Pr | 2 | OMe | |

TABLE A-continued

Compounds according to the invention of the general formula (I) in which $R^1$ is methyl, $R^4$ is hydrogen and q is zero

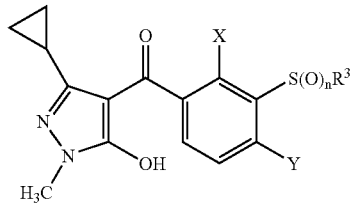

| No. | X | $R^3$ | n | Y | Physical data: $^1$H-NMR: δ[CDCl$_3$] |
|---|---|---|---|---|---|
| 1-969 | CH$_2$OCH$_2$OEt | (CH$_2$)$_2$OMe | 2 | OMe | |
| 1-970 | CH$_2$OCH$_2$OEt | (CH$_2$)$_3$OMe | 2 | OMe | |
| 1-971 | CH$_2$OCH$_2$OEt | (CH$_2$)$_2$OEt | 2 | OMe | |
| 1-972 | CH$_2$OCH$_2$OEt | (CH$_2$)$_2$OCH$_2$-c-Pr | 2 | OMe | |
| 1-973 | CH$_2$O(CH$_2$)$_2$SO$_2$Me | c-Pr | 0 | OMe | |
| 1-974 | CH$_2$O(CH$_2$)$_2$SO$_2$Me | CH$_2$-c-Pr | 0 | OMe | |
| 1-975 | CH$_2$O(CH$_2$)$_2$SO$_2$Me | (CH$_2$)$_2$OMe | 0 | OMe | |
| 1-976 | CH$_2$O(CH$_2$)$_2$SO$_2$Me | (CH$_2$)$_3$OMe | 0 | OMe | |
| 1-977 | CH$_2$O(CH$_2$)$_2$SO$_2$Me | (CH$_2$)$_2$OEt | 0 | OMe | |
| 1-978 | CH$_2$O(CH$_2$)$_2$SO$_2$Me | (CH$_2$)$_2$OCH$_2$-c-Pr | 0 | OMe | |
| 1-979 | CH$_2$O(CH$_2$)$_2$SO$_2$Me | c-Pr | 1 | OMe | |
| 1-980 | CH$_2$O(CH$_2$)$_2$SO$_2$Me | CH$_2$-c-Pr | 1 | OMe | |
| 1-981 | CH$_2$O(CH$_2$)$_2$SO$_2$Me | (CH$_2$)$_2$OMe | 1 | OMe | |
| 1-982 | CH$_2$O(CH$_2$)$_2$SO$_2$Me | (CH$_2$)$_3$OMe | 1 | OMe | |
| 1-983 | CH$_2$O(CH$_2$)$_2$SO$_2$Me | (CH$_2$)$_2$OEt | 1 | OMe | |
| 1-984 | CH$_2$O(CH$_2$)$_2$SO$_2$Me | (CH$_2$)$_2$OCH$_2$-c-Pr | 1 | OMe | |
| 1-985 | CH$_2$O(CH$_2$)$_2$SO$_2$Me | c-Pr | 2 | OMe | |
| 1-986 | CH$_2$O(CH$_2$)$_2$SO$_2$Me | CH$_2$-c-Pr | 2 | OMe | |
| 1-987 | CH$_2$O(CH$_2$)$_2$SO$_2$Me | (CH$_2$)$_2$OMe | 2 | OMe | |
| 1-988 | CH$_2$O(CH$_2$)$_2$SO$_2$Me | (CH$_2$)$_3$OMe | 2 | OMe | |
| 1-989 | CH$_2$O(CH$_2$)$_2$SO$_2$Me | (CH$_2$)$_2$OEt | 2 | OMe | |
| 1-990 | CH$_2$O(CH$_2$)$_2$SO$_2$Me | (CH$_2$)$_2$OCH$_2$-c-Pr | 2 | OMe | |
| 1-991 | CH$_2$SO$_2$(CH$_2$)$_2$OMe | c-Pr | 0 | OMe | |
| 1-992 | CH$_2$SO$_2$(CH$_2$)$_2$OMe | CH$_2$-c-Pr | 0 | OMe | |
| 1-993 | CH$_2$SO$_2$(CH$_2$)$_2$OMe | (CH$_2$)$_2$OMe | 0 | OMe | |
| 1-994 | CH$_2$SO$_2$(CH$_2$)$_2$OMe | (CH$_2$)$_3$OMe | 0 | OMe | |
| 1-995 | CH$_2$SO$_2$(CH$_2$)$_2$OMe | (CH$_2$)$_2$OEt | 0 | OMe | |
| 1-996 | CH$_2$SO$_2$(CH$_2$)$_2$OMe | (CH$_2$)$_2$OCH$_2$-c-Pr | 0 | OMe | |
| 1-997 | CH$_2$SO$_2$(CH$_2$)$_2$OMe | c-Pr | 1 | OMe | |
| 1-998 | CH$_2$SO$_2$(CH$_2$)$_2$OMe | CH$_2$-c-Pr | 1 | OMe | |
| 1-999 | CH$_2$SO$_2$(CH$_2$)$_2$OMe | (CH$_2$)$_2$OMe | 1 | OMe | |
| 1-1000 | CH$_2$SO$_2$(CH$_2$)$_2$OMe | (CH$_2$)$_3$OMe | 1 | OMe | |
| 1-1001 | CH$_2$SO$_2$(CH$_2$)$_2$OMe | (CH$_2$)$_2$OEt | 1 | OMe | |
| 1-1002 | CH$_2$SO$_2$(CH$_2$)$_2$OMe | (CH$_2$)$_2$OCH$_2$-c-Pr | 1 | OMe | |
| 1-1003 | CH$_2$SO$_2$(CH$_2$)$_2$OMe | c-Pr | 2 | OMe | |
| 1-1004 | CH$_2$SO$_2$(CH$_2$)$_2$OMe | CH$_2$-c-Pr | 2 | OMe | |
| 1-1005 | CH$_2$SO$_2$(CH$_2$)$_2$OMe | (CH$_2$)$_2$OMe | 2 | OMe | |
| 1-1006 | CH$_2$SO$_2$(CH$_2$)$_2$OMe | (CH$_2$)$_3$OMe | 2 | OMe | |
| 1-1007 | CH$_2$SO$_2$(CH$_2$)$_2$OMe | (CH$_2$)$_2$OEt | 2 | OMe | |
| 1-1008 | CH$_2$SO$_2$(CH$_2$)$_2$OMe | (CH$_2$)$_2$OCH$_2$-c-Pr | 2 | OMe | |
| 1-1009 | CH$_2$SO$_2$(CH$_2$)$_2$SO$_2$Me | c-Pr | 0 | OMe | |
| 1-1010 | CH$_2$SO$_2$(CH$_2$)$_2$SO$_2$Me | CH$_2$-c-Pr | 0 | OMe | |
| 1-1011 | CH$_2$SO$_2$(CH$_2$)$_2$SO$_2$Me | (CH$_2$)$_2$OMe | 0 | OMe | |
| 1-1012 | CH$_2$SO$_2$(CH$_2$)$_2$SO$_2$Me | (CH$_2$)$_3$OMe | 0 | OMe | |
| 1-1013 | CH$_2$SO$_2$(CH$_2$)$_2$SO$_2$Me | (CH$_2$)$_2$OEt | 0 | OMe | |
| 1-1014 | CH$_2$SO$_2$(CH$_2$)$_2$SO$_2$Me | (CH$_2$)$_2$OCH$_2$-c-Pr | 0 | OMe | |
| 1-1015 | CH$_2$SO$_2$(CH$_2$)$_2$SO$_2$Me | c-Pr | 1 | OMe | |
| 1-1016 | CH$_2$SO$_2$(CH$_2$)$_2$SO$_2$Me | CH$_2$-c-Pr | 1 | OMe | |
| 1-1017 | CH$_2$SO$_2$(CH$_2$)$_2$SO$_2$Me | (CH$_2$)$_2$OMe | 1 | OMe | |
| 1-1018 | CH$_2$SO$_2$(CH$_2$)$_2$SO$_2$Me | (CH$_2$)$_3$OMe | 1 | OMe | |
| 1-1019 | CH$_2$SO$_2$(CH$_2$)$_2$SO$_2$Me | (CH$_2$)$_2$OEt | 1 | OMe | |
| 1-1020 | CH$_2$SO$_2$(CH$_2$)$_2$SO$_2$Me | (CH$_2$)$_2$OCH$_2$-c-Pr | 1 | OMe | |
| 1-1021 | CH$_2$SO$_2$(CH$_2$)$_2$SO$_2$Me | c-Pr | 2 | OMe | |
| 1-1022 | CH$_2$SO$_2$(CH$_2$)$_2$SO$_2$Me | CH$_2$-c-Pr | 2 | OMe | |
| 1-1023 | CH$_2$SO$_2$(CH$_2$)$_2$SO$_2$Me | (CH$_2$)$_2$OMe | 2 | OMe | |
| 1-1024 | CH$_2$SO$_2$(CH$_2$)$_2$SO$_2$Me | (CH$_2$)$_3$OMe | 2 | OMe | |
| 1-1025 | CH$_2$SO$_2$(CH$_2$)$_2$SO$_2$Me | (CH$_2$)$_2$OEt | 2 | OMe | |
| 1-1026 | CH$_2$SO$_2$(CH$_2$)$_2$SO$_2$Me | (CH$_2$)$_2$OCH$_2$-c-Pr | 2 | OMe | |
| 1-1027 | Cl | c-Pr | 0 | F | |
| 1-1028 | Cl | CH$_2$-c-Pr | 0 | F | |
| 1-1029 | Cl | (CH$_2$)$_2$OMe | 0 | F | |
| 1-1030 | Cl | (CH$_2$)$_3$OMe | 0 | F | |
| 1-1031 | Cl | (CH$_2$)$_2$OEt | 0 | F | |

TABLE A-continued

Compounds according to the invention of the general formula (I) in which $R^1$ is methyl, $R^4$ is hydrogen and q is zero

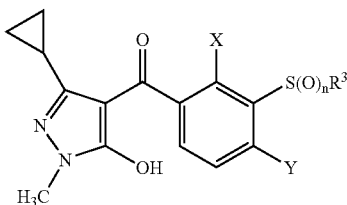

| No. | X | $R^3$ | n | Y | Physical data: $^1$H-NMR: δ[CDCl$_3$] |
|---|---|---|---|---|---|
| 1-1032 | Cl | (CH$_2$)$_2$OCH$_2$-c-Pr | 0 | F | |
| 1-1033 | Cl | c-Pr | 1 | F | |
| 1-1034 | Cl | CH$_2$-c-Pr | 1 | F | |
| 1-1035 | Cl | (CH$_2$)$_2$OMe | 1 | F | |
| 1-1036 | Cl | (CH$_2$)$_3$OMe | 1 | F | |
| 1-1037 | Cl | (CH$_2$)$_2$OEt | 1 | F | |
| 1-1038 | Cl | (CH$_2$)$_2$OCH$_2$-c-Pr | 1 | F | |
| 1-1039 | Cl | c-Pr | 2 | F | |
| 1-1040 | Cl | CH$_2$-c-Pr | 2 | F | |
| 1-1041 | Cl | (CH$_2$)$_2$OMe | 2 | F | |
| 1-1042 | Cl | (CH$_2$)$_3$OMe | 2 | F | |
| 1-1043 | Cl | (CH$_2$)$_2$OEt | 2 | F | |
| 1-1044 | Cl | (CH$_2$)$_2$OCH$_2$-c-Pr | 2 | F | |
| 1-1045 | Br | c-Pr | 0 | F | |
| 1-1046 | Br | CH$_2$-c-Pr | 0 | F | |
| 1-1047 | Br | (CH$_2$)$_2$OMe | 0 | F | |
| 1-1048 | Br | (CH$_2$)$_3$OMe | 0 | F | |
| 1-1049 | Br | (CH$_2$)$_2$OEt | 0 | F | |
| 1-1050 | Br | (CH$_2$)$_2$OCH$_2$-c-Pr | 0 | F | |
| 1-1051 | Br | c-Pr | 1 | F | |
| 1-1052 | Br | CH$_2$-c-Pr | 1 | F | |
| 1-1053 | Br | (CH$_2$)$_2$OMe | 1 | F | |
| 1-1054 | Br | (CH$_2$)$_3$OMe | 1 | F | |
| 1-1055 | Br | (CH$_2$)$_2$OEt | 1 | F | |
| 1-1056 | Br | (CH$_2$)$_2$OCH$_2$-c-Pr | 1 | F | |
| 1-1057 | Br | c-Pr | 2 | F | |
| 1-1058 | Br | CH$_2$-c-Pr | 2 | F | |
| 1-1059 | Br | (CH$_2$)$_2$OMe | 2 | F | |
| 1-1060 | Br | (CH$_2$)$_3$OMe | 2 | F | |
| 1-1061 | Br | (CH$_2$)$_2$OEt | 2 | F | |
| 1-1062 | Br | (CH$_2$)$_2$OCH$_2$-c-Pr | 2 | F | |
| 1-1063 | Me | c-Pr | 0 | F | |
| 1-1064 | Me | CH$_2$-c-Pr | 0 | F | |
| 1-1065 | Me | (CH$_2$)$_2$OMe | 0 | F | |
| 1-1066 | Me | (CH$_2$)$_3$OMe | 0 | F | |
| 1-1067 | Me | (CH$_2$)$_2$OEt | 0 | F | |
| 1-1068 | Me | (CH$_2$)$_2$OCH$_2$-c-Pr | 0 | F | |
| 1-1069 | Me | c-Pr | 1 | F | |
| 1-1070 | Me | CH$_2$-c-Pr | 1 | F | |
| 1-1071 | Me | (CH$_2$)$_2$OMe | 1 | F | |
| 1-1072 | Me | (CH$_2$)$_3$OMe | 1 | F | |
| 1-1073 | Me | (CH$_2$)$_2$OEt | 1 | F | |
| 1-1074 | Me | (CH$_2$)$_2$OCH$_2$-c-Pr | 1 | F | |
| 1-1075 | Me | c-Pr | 2 | F | |
| 1-1076 | Me | CH$_2$-c-Pr | 2 | F | |
| 1-1077 | Me | (CH$_2$)$_2$OMe | 2 | F | |
| 1-1078 | Me | (CH$_2$)$_3$OMe | 2 | F | |
| 1-1079 | Me | (CH$_2$)$_2$OEt | 2 | F | |
| 1-1080 | Me | (CH$_2$)$_2$OCH$_2$-c-Pr | 2 | F | |
| 1-1081 | Et | c-Pr | 0 | F | |
| 1-1082 | Et | CH$_2$-c-Pr | 0 | F | |
| 1-1083 | Et | (CH$_2$)$_2$OMe | 0 | F | |
| 1-1084 | Et | (CH$_2$)$_3$OMe | 0 | F | |
| 1-1085 | Et | (CH$_2$)$_2$OEt | 0 | F | |
| 1-1086 | Et | (CH$_2$)$_2$OCH$_2$-c-Pr | 0 | F | |
| 1-1087 | Et | c-Pr | 1 | F | |
| 1-1088 | Et | CH$_2$-c-Pr | 1 | F | |
| 1-1089 | Et | (CH$_2$)$_2$OMe | 1 | F | |
| 1-1090 | Et | (CH$_2$)$_3$OMe | 1 | F | |
| 1-1091 | Et | (CH$_2$)$_2$OEt | 1 | F | |
| 1-1092 | Et | (CH$_2$)$_2$OCH$_2$-c-Pr | 1 | F | |
| 1-1093 | Et | c-Pr | 2 | F | |
| 1-1094 | Et | CH$_2$-c-Pr | 2 | F | |

TABLE A-continued

Compounds according to the invention of the general formula (I) in which $R^1$ is methyl, $R^4$ is hydrogen and q is zero

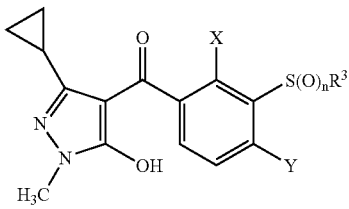

| No. | X | $R^3$ | n | Y | Physical data: $^1$H-NMR: δ[CDCl$_3$] |
|---|---|---|---|---|---|
| 1-1095 | Et | (CH$_2$)$_2$OMe | 2 | F | |
| 1-1096 | Et | (CH$_2$)$_3$OMe | 2 | F | |
| 1-1097 | Et | (CH$_2$)$_2$OEt | 2 | F | |
| 1-1098 | Et | (CH$_2$)$_2$OCH$_2$-c-Pr | 2 | F | |
| 1-1099 | CF$_3$ | c-Pr | 0 | F | |
| 1-1100 | CF$_3$ | CH$_2$-c-Pr | 0 | F | |
| 1-1101 | CF$_3$ | (CH$_2$)$_2$OMe | 0 | F | |
| 1-1102 | CF$_3$ | (CH$_2$)$_3$OMe | 0 | F | |
| 1-1103 | CF$_3$ | (CH$_2$)$_2$OEt | 0 | F | |
| 1-1104 | CF$_3$ | (CH$_2$)$_2$OCH$_2$-c-Pr | 0 | F | |
| 1-1105 | CF$_3$ | c-Pr | 1 | F | |
| 1-1106 | CF$_3$ | CH$_2$-c-Pr | 1 | F | |
| 1-1107 | CF$_3$ | (CH$_2$)$_2$OMe | 1 | F | |
| 1-1108 | CF$_3$ | (CH$_2$)$_3$OMe | 1 | F | |
| 1-1109 | CF$_3$ | (CH$_2$)$_2$OEt | 1 | F | |
| 1-1110 | CF$_3$ | (CH$_2$)$_2$OCH$_2$-c-Pr | 1 | F | |
| 1-1111 | CF$_3$ | c-Pr | 2 | F | |
| 1-1112 | CF$_3$ | CH$_2$-c-Pr | 2 | F | |
| 1-1113 | CF$_3$ | (CH$_2$)$_2$OMe | 2 | F | |
| 1-1114 | CF$_3$ | (CH$_2$)$_3$OMe | 2 | F | |
| 1-1115 | CF$_3$ | (CH$_2$)$_2$OEt | 2 | F | |
| 1-1116 | CF$_3$ | (CH$_2$)$_2$OCH$_2$-c-Pr | 2 | F | |
| 1-1117 | OMe | c-Pr | 0 | F | |
| 1-1118 | OMe | CH$_2$-c-Pr | 0 | F | |
| 1-1119 | OMe | (CH$_2$)$_2$OMe | 0 | F | |
| 1-1120 | OMe | (CH$_2$)$_3$OMe | 0 | F | |
| 1-1121 | OMe | (CH$_2$)$_2$OEt | 0 | F | |
| 1-1122 | OMe | (CH$_2$)$_2$OCH$_2$-c-Pr | 0 | F | |
| 1-1123 | OMe | c-Pr | 1 | F | |
| 1-1124 | OMe | CH$_2$-c-Pr | 1 | F | |
| 1-1125 | OMe | (CH$_2$)$_2$OMe | 1 | F | |
| 1-1126 | OMe | (CH$_2$)$_3$OMe | 1 | F | |
| 1-1127 | OMe | (CH$_2$)$_2$OEt | 1 | F | |
| 1-1128 | OMe | (CH$_2$)$_2$OCH$_2$-c-Pr | 1 | F | |
| 1-1129 | OMe | c-Pr | 2 | F | |
| 1-1130 | OMe | CH$_2$-c-Pr | 2 | F | |
| 1-1131 | OMe | (CH$_2$)$_2$OMe | 2 | F | |
| 1-1132 | OMe | (CH$_2$)$_3$OMe | 2 | F | |
| 1-1133 | OMe | (CH$_2$)$_2$OEt | 2 | F | |
| 1-1134 | OMe | (CH$_2$)$_2$OCH$_2$-c-Pr | 2 | F | |
| 1-1135 | OEt | c-Pr | 0 | F | |
| 1-1136 | OEt | CH$_2$-c-Pr | 0 | F | |
| 1-1137 | OEt | (CH$_2$)$_2$OMe | 0 | F | |
| 1-1138 | OEt | (CH$_2$)$_3$OMe | 0 | F | |
| 1-1139 | OEt | (CH$_2$)$_2$OEt | 0 | F | |
| 1-1140 | OEt | (CH$_2$)$_2$OCH$_2$-c-Pr | 0 | F | |
| 1-1141 | OEt | c-Pr | 1 | F | |
| 1-1142 | OEt | CH$_2$-c-Pr | 1 | F | |
| 1-1143 | OEt | (CH$_2$)$_2$OMe | 1 | F | |
| 1-1144 | OEt | (CH$_2$)$_3$OMe | 1 | F | |
| 1-1145 | OEt | (CH$_2$)$_2$OEt | 1 | F | |
| 1-1146 | OEt | (CH$_2$)$_2$OCH$_2$-c-Pr | 1 | F | |
| 1-1147 | OEt | c-Pr | 2 | F | |
| 1-1148 | OEt | CH$_2$-c-Pr | 2 | F | |
| 1-1149 | OEt | (CH$_2$)$_2$OMe | 2 | F | |
| 1-1150 | OEt | (CH$_2$)$_3$OMe | 2 | F | |
| 1-1151 | OEt | (CH$_2$)$_2$OEt | 2 | F | |
| 1-1152 | OEt | (CH$_2$)$_2$OCH$_2$-c-Pr | 2 | F | |
| 1-1153 | NO$_2$ | c-Pr | 0 | F | |
| 1-1154 | NO$_2$ | CH$_2$-c-Pr | 0 | F | |
| 1-1155 | NO$_2$ | (CH$_2$)$_2$OMe | 0 | F | |
| 1-1156 | NO$_2$ | (CH$_2$)$_3$OMe | 0 | F | |
| 1-1157 | NO$_2$ | (CH$_2$)$_2$OEt | 0 | F | |

TABLE A-continued

Compounds according to the invention of the general formula (I) in which $R^1$ is methyl, $R^4$ is hydrogen and q is zero

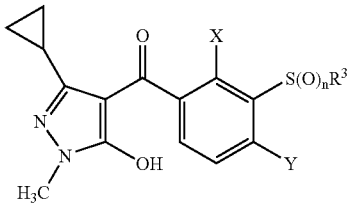

| No. | X | $R^3$ | n | Y | Physical data: $^1$H-NMR: δ[CDCl$_3$] |
|---|---|---|---|---|---|
| 1-1158 | NO$_2$ | (CH$_2$)$_2$OCH$_2$-c-Pr | 0 | F | |
| 1-1159 | NO$_2$ | c-Pr | 1 | F | |
| 1-1160 | NO$_2$ | CH$_2$-c-Pr | 1 | F | |
| 1-1161 | NO$_2$ | (CH$_2$)$_2$OMe | 1 | F | |
| 1-1162 | NO$_2$ | (CH$_2$)$_3$OMe | 1 | F | |
| 1-1163 | NO$_2$ | (CH$_2$)$_2$OEt | 1 | F | |
| 1-1164 | NO$_2$ | (CH$_2$)$_2$OCH$_2$-c-Pr | 1 | F | |
| 1-1165 | NO$_2$ | c-Pr | 2 | F | |
| 1-1166 | NO$_2$ | CH$_2$-c-Pr | 2 | F | |
| 1-1167 | NO$_2$ | (CH$_2$)$_2$OMe | 2 | F | |
| 1-1168 | NO$_2$ | (CH$_2$)$_3$OMe | 2 | F | |
| 1-1169 | NO$_2$ | (CH$_2$)$_2$OEt | 2 | F | |
| 1-1170 | NO$_2$ | (CH$_2$)$_2$OCH$_2$-c-Pr | 2 | F | |
| 1-1171 | SO$_2$Me | c-Pr | 0 | F | |
| 1-1172 | SO$_2$Me | CH$_2$-c-Pr | 0 | F | |
| 1-1173 | SO$_2$Me | (CH$_2$)$_2$OMe | 0 | F | |
| 1-1174 | SO$_2$Me | (CH$_2$)$_3$OMe | 0 | F | |
| 1-1175 | SO$_2$Me | (CH$_2$)$_2$OEt | 0 | F | |
| 1-1176 | SO$_2$Me | (CH$_2$)$_2$OCH$_2$-c-Pr | 0 | F | |
| 1-1177 | SO$_2$Me | c-Pr | 1 | F | |
| 1-1178 | SO$_2$Me | CH$_2$-c-Pr | 1 | F | |
| 1-1179 | SO$_2$Me | (CH$_2$)$_2$OMe | 1 | F | |
| 1-1180 | SO$_2$Me | (CH$_2$)$_3$OMe | 1 | F | |
| 1-1181 | SO$_2$Me | (CH$_2$)$_2$OEt | 1 | F | |
| 1-1182 | SO$_2$Me | (CH$_2$)$_2$OCH$_2$-c-Pr | 1 | F | |
| 1-1183 | SO$_2$Me | c-Pr | 2 | F | |
| 1-1184 | SO$_2$Me | CH$_2$-c-Pr | 2 | F | |
| 1-1185 | SO$_2$Me | (CH$_2$)$_2$OMe | 2 | F | |
| 1-1186 | SO$_2$Me | (CH$_2$)$_3$OMe | 2 | F | |
| 1-1187 | SO$_2$Me | (CH$_2$)$_2$OEt | 2 | F | |
| 1-1188 | SO$_2$Me | (CH$_2$)$_2$OCH$_2$-c-Pr | 2 | F | |
| 1-1189 | CH$_2$OMe | c-Pr | 0 | F | |
| 1-1190 | CH$_2$OMe | CH$_2$-c-Pr | 0 | F | |
| 1-1191 | CH$_2$OMe | (CH$_2$)$_2$OMe | 0 | F | |
| 1-1192 | CH$_2$OMe | (CH$_2$)$_3$OMe | 0 | F | |
| 1-1193 | CH$_2$OMe | (CH$_2$)$_2$OEt | 0 | F | |
| 1-1194 | CH$_2$OMe | (CH$_2$)$_2$OCH$_2$-c-Pr | 0 | F | |
| 1-1195 | CH$_2$OMe | c-Pr | 1 | F | |
| 1-1196 | CH$_2$OMe | CH$_2$-c-Pr | 1 | F | |
| 1-1197 | CH$_2$OMe | (CH$_2$)$_2$OMe | 1 | F | |
| 1-1198 | CH$_2$OMe | (CH$_2$)$_3$OMe | 1 | F | |
| 1-1199 | CH$_2$OMe | (CH$_2$)$_2$OEt | 1 | F | |
| 1-1200 | CH$_2$OMe | (CH$_2$)$_2$OCH$_2$-c-Pr | 1 | F | |
| 1-1201 | CH$_2$OMe | c-Pr | 2 | F | |
| 1-1202 | CH$_2$OMe | CH$_2$-c-Pr | 2 | F | |
| 1-1203 | CH$_2$OMe | (CH$_2$)$_2$OMe | 2 | F | |
| 1-1204 | CH$_2$OMe | (CH$_2$)$_3$OMe | 2 | F | |
| 1-1205 | CH$_2$OMe | (CH$_2$)$_2$OEt | 2 | F | |
| 1-1206 | CH$_2$OMe | (CH$_2$)$_2$OCH$_2$-c-Pr | 2 | F | |
| 1-1207 | CH$_2$SO$_2$Me | c-Pr | 0 | F | |
| 1-1208 | CH$_2$SO$_2$Me | CH$_2$-c-Pr | 0 | F | |
| 1-1209 | CH$_2$SO$_2$Me | (CH$_2$)$_2$OMe | 0 | F | |
| 1-1210 | CH$_2$SO$_2$Me | (CH$_2$)$_3$OMe | 0 | F | |
| 1-1211 | CH$_2$SO$_2$Me | (CH$_2$)$_2$OEt | 0 | F | |
| 1-1212 | CH$_2$SO$_2$Me | (CH$_2$)$_2$OCH$_2$-c-Pr | 0 | F | |
| 1-1213 | CH$_2$SO$_2$Me | c-Pr | 1 | F | |
| 1-1214 | CH$_2$SO$_2$Me | CH$_2$-c-Pr | 1 | F | |
| 1-1215 | CH$_2$SO$_2$Me | (CH$_2$)$_2$OMe | 1 | F | |
| 1-1216 | CH$_2$SO$_2$Me | (CH$_2$)$_3$OMe | 1 | F | |
| 1-1217 | CH$_2$SO$_2$Me | (CH$_2$)$_2$OEt | 1 | F | |
| 1-1218 | CH$_2$SO$_2$Me | (CH$_2$)$_2$OCH$_2$-c-Pr | 1 | F | |
| 1-1219 | CH$_2$SO$_2$Me | c-Pr | 2 | F | |
| 1-1220 | CH$_2$SO$_2$Me | CH$_2$-c-Pr | 2 | F | |

TABLE A-continued

Compounds according to the invention of the general formula (I) in which $R^1$ is methyl, $R^4$ is hydrogen and q is zero

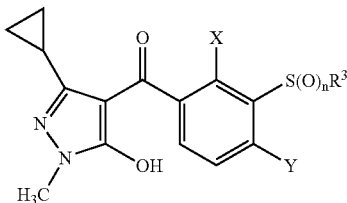

| No. | X | $R^3$ | n | Y | Physical data: $^1$H-NMR: δ[CDCl$_3$] |
|---|---|---|---|---|---|
| 1-1221 | CH$_2$SO$_2$Me | (CH$_2$)$_2$OMe | 2 | F | |
| 1-1222 | CH$_2$SO$_2$Me | (CH$_2$)$_3$OMe | 2 | F | |
| 1-1223 | CH$_2$SO$_2$Me | (CH$_2$)$_2$OEt | 2 | F | |
| 1-1224 | CH$_2$SO$_2$Me | (CH$_2$)$_2$OCH$_2$-c-Pr | 2 | F | |
| 1-1225 | CH$_2$O(CH$_2$)$_2$OMe | c-Pr | 0 | F | |
| 1-1226 | CH$_2$O(CH$_2$)$_2$OMe | CH$_2$-c-Pr | 0 | F | |
| 1-1227 | CH$_2$O(CH$_2$)$_2$OMe | (CH$_2$)$_2$OMe | 0 | F | |
| 1-1228 | CH$_2$O(CH$_2$)$_2$OMe | (CH$_2$)$_3$OMe | 0 | F | |
| 1-1229 | CH$_2$O(CH$_2$)$_2$OMe | (CH$_2$)$_2$OEt | 0 | F | |
| 1-1230 | CH$_2$O(CH$_2$)$_2$OMe | (CH$_2$)$_2$OCH$_2$-c-Pr | 0 | F | |
| 1-1231 | CH$_2$O(CH$_2$)$_2$OMe | c-Pr | 1 | F | |
| 1-1232 | CH$_2$O(CH$_2$)$_2$OMe | CH$_2$-c-Pr | 1 | F | |
| 1-1233 | CH$_2$O(CH$_2$)$_2$OMe | (CH$_2$)$_2$OMe | 1 | F | |
| 1-1234 | CH$_2$O(CH$_2$)$_2$OMe | (CH$_2$)$_3$OMe | 1 | F | |
| 1-1235 | CH$_2$O(CH$_2$)$_2$OMe | (CH$_2$)$_2$OEt | 1 | F | |
| 1-1236 | CH$_2$O(CH$_2$)$_2$OMe | (CH$_2$)$_2$OCH$_2$-c-Pr | 1 | F | |
| 1-1237 | CH$_2$O(CH$_2$)$_2$OMe | c-Pr | 2 | F | |
| 1-1238 | CH$_2$O(CH$_2$)$_2$OMe | CH$_2$-c-Pr | 2 | F | |
| 1-1239 | CH$_2$O(CH$_2$)$_2$OMe | (CH$_2$)$_2$OMe | 2 | F | |
| 1-1240 | CH$_2$O(CH$_2$)$_2$OMe | (CH$_2$)$_3$OMe | 2 | F | |
| 1-1241 | CH$_2$O(CH$_2$)$_2$OMe | (CH$_2$)$_2$OEt | 2 | F | |
| 1-1242 | CH$_2$O(CH$_2$)$_2$OMe | (CH$_2$)$_2$OCH$_2$-c-Pr | 2 | F | |
| 1-1243 | CH$_2$O(CH$_2$)$_2$OEt | c-Pr | 0 | F | |
| 1-1244 | CH$_2$O(CH$_2$)$_2$OEt | CH$_2$-c-Pr | 0 | F | |
| 1-1245 | CH$_2$O(CH$_2$)$_2$OEt | (CH$_2$)$_2$OMe | 0 | F | |
| 1-1246 | CH$_2$O(CH$_2$)$_2$OEt | (CH$_2$)$_3$OMe | 0 | F | |
| 1-1247 | CH$_2$O(CH$_2$)$_2$OEt | (CH$_2$)$_2$OEt | 0 | F | |
| 1-1248 | CH$_2$O(CH$_2$)$_2$OEt | (CH$_2$)$_2$OCH$_2$-c-Pr | 0 | F | |
| 1-1249 | CH$_2$O(CH$_2$)$_2$OEt | c-Pr | 1 | F | |
| 1-1250 | CH$_2$O(CH$_2$)$_2$OEt | CH$_2$-c-Pr | 1 | F | |
| 1-1251 | CH$_2$O(CH$_2$)$_2$OEt | (CH$_2$)$_2$OMe | 1 | F | |
| 1-1252 | CH$_2$O(CH$_2$)$_2$OEt | (CH$_2$)$_3$OMe | 1 | F | |
| 1-1253 | CH$_2$O(CH$_2$)$_2$OEt | (CH$_2$)$_2$OEt | 1 | F | |
| 1-1254 | CH$_2$O(CH$_2$)$_2$OEt | (CH$_2$)$_2$OCH$_2$-c-Pr | 1 | F | |
| 1-1255 | CH$_2$O(CH$_2$)$_2$OEt | c-Pr | 2 | F | |
| 1-1256 | CH$_2$O(CH$_2$)$_2$OEt | CH$_2$-c-Pr | 2 | F | |
| 1-1257 | CH$_2$O(CH$_2$)$_2$OEt | (CH$_2$)$_2$OMe | 2 | F | |
| 1-1258 | CH$_2$O(CH$_2$)$_2$OEt | (CH$_2$)$_3$OMe | 2 | F | |
| 1-1259 | CH$_2$O(CH$_2$)$_2$OEt | (CH$_2$)$_2$OEt | 2 | F | |
| 1-1260 | CH$_2$O(CH$_2$)$_2$OEt | (CH$_2$)$_2$OCH$_2$-c-Pr | 2 | F | |
| 1-1261 | CH$_2$O(CH$_2$)$_3$OMe | c-Pr | 0 | F | |
| 1-1262 | CH$_2$O(CH$_2$)$_3$OMe | CH$_2$-c-Pr | 0 | F | |
| 1-1263 | CH$_2$O(CH$_2$)$_3$OMe | (CH$_2$)$_2$OMe | 0 | F | |
| 1-1264 | CH$_2$O(CH$_2$)$_3$OMe | (CH$_2$)$_3$OMe | 0 | F | |
| 1-1265 | CH$_2$O(CH$_2$)$_3$OMe | (CH$_2$)$_2$OEt | 0 | F | |
| 1-1266 | CH$_2$O(CH$_2$)$_3$OMe | (CH$_2$)$_2$OCH$_2$-c-Pr | 0 | F | |
| 1-1267 | CH$_2$O(CH$_2$)$_3$OMe | c-Pr | 1 | F | |
| 1-1268 | CH$_2$O(CH$_2$)$_3$OMe | CH$_2$-c-Pr | 1 | F | |
| 1-1269 | CH$_2$O(CH$_2$)$_3$OMe | (CH$_2$)$_2$OMe | 1 | F | |
| 1-1270 | CH$_2$O(CH$_2$)$_3$OMe | (CH$_2$)$_3$OMe | 1 | F | |
| 1-1271 | CH$_2$O(CH$_2$)$_3$OMe | (CH$_2$)$_2$OEt | 1 | F | |
| 1-1272 | CH$_2$O(CH$_2$)$_3$OMe | (CH$_2$)$_2$OCH$_2$-c-Pr | 1 | F | |
| 1-1273 | CH$_2$O(CH$_2$)$_3$OMe | c-Pr | 2 | F | |
| 1-1274 | CH$_2$O(CH$_2$)$_3$OMe | CH$_2$-c-Pr | 2 | F | |
| 1-1275 | CH$_2$O(CH$_2$)$_3$OMe | (CH$_2$)$_2$OMe | 2 | F | |
| 1-1276 | CH$_2$O(CH$_2$)$_3$OMe | (CH$_2$)$_3$OMe | 2 | F | |
| 1-1277 | CH$_2$O(CH$_2$)$_3$OMe | (CH$_2$)$_2$OEt | 2 | F | |
| 1-1278 | CH$_2$O(CH$_2$)$_3$OMe | (CH$_2$)$_2$OCH$_2$-c-Pr | 2 | F | |
| 1-1279 | CH$_2$OCH$_2$OMe | c-Pr | 0 | F | |
| 1-1280 | CH$_2$OCH$_2$OMe | CH$_2$-c-Pr | 0 | F | |
| 1-1281 | CH$_2$OCH$_2$OMe | (CH$_2$)$_2$OMe | 0 | F | |
| 1-1282 | CH$_2$OCH$_2$OMe | (CH$_2$)$_3$OMe | 0 | F | |
| 1-1283 | CH$_2$OCH$_2$OMe | (CH$_2$)$_2$OEt | 0 | F | |

TABLE A-continued

Compounds according to the invention of the general formula (I) in which $R^1$ is methyl, $R^4$ is hydrogen and q is zero

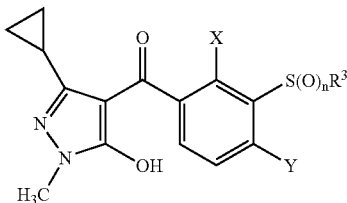

| No. | X | $R^3$ | n | Y | Physical data: $^1$H-NMR: δ[CDCl$_3$] |
|---|---|---|---|---|---|
| 1-1284 | CH$_2$OCH$_2$OMe | (CH$_2$)$_2$OCH$_2$-c-Pr | 0 | F | |
| 1-1285 | CH$_2$OCH$_2$OMe | c-Pr | 1 | F | |
| 1-1286 | CH$_2$OCH$_2$OMe | CH$_2$-c-Pr | 1 | F | |
| 1-1287 | CH$_2$OCH$_2$OMe | (CH$_2$)$_2$OMe | 1 | F | |
| 1-1288 | CH$_2$OCH$_2$OMe | (CH$_2$)$_3$OMe | 1 | F | |
| 1-1289 | CH$_2$OCH$_2$OMe | (CH$_2$)$_2$OEt | 1 | F | |
| 1-1290 | CH$_2$OCH$_2$OMe | (CH$_2$)$_2$OCH$_2$-c-Pr | 1 | F | |
| 1-1291 | CH$_2$OCH$_2$OMe | c-Pr | 2 | F | |
| 1-1292 | CH$_2$OCH$_2$OMe | CH$_2$-c-Pr | 2 | F | |
| 1-1293 | CH$_2$OCH$_2$OMe | (CH$_2$)$_2$OMe | 2 | F | |
| 1-1294 | CH$_2$OCH$_2$OMe | (CH$_2$)$_3$OMe | 2 | F | |
| 1-1295 | CH$_2$OCH$_2$OMe | (CH$_2$)$_2$OEt | 2 | F | |
| 1-1296 | CH$_2$OCH$_2$OMe | (CH$_2$)$_2$OCH$_2$-c-Pr | 2 | F | |
| 1-1297 | CH$_2$OCH$_2$OEt | c-Pr | 0 | F | |
| 1-1298 | CH$_2$OCH$_2$OEt | CH$_2$-c-Pr | 0 | F | |
| 1-1299 | CH$_2$OCH$_2$OEt | (CH$_2$)$_2$OMe | 0 | F | |
| 1-1300 | CH$_2$OCH$_2$OEt | (CH$_2$)$_3$OMe | 0 | F | |
| 1-1301 | CH$_2$OCH$_2$OEt | (CH$_2$)$_2$OEt | 0 | F | |
| 1-1302 | CH$_2$OCH$_2$OEt | (CH$_2$)$_2$OCH$_2$-c-Pr | 0 | F | |
| 1-1303 | CH$_2$OCH$_2$OEt | c-Pr | 1 | F | |
| 1-1304 | CH$_2$OCH$_2$OEt | CH$_2$-c-Pr | 1 | F | |
| 1-1305 | CH$_2$OCH$_2$OEt | (CH$_2$)$_2$OMe | 1 | F | |
| 1-1306 | CH$_2$OCH$_2$OEt | (CH$_2$)$_3$OMe | 1 | F | |
| 1-1307 | CH$_2$OCH$_2$OEt | (CH$_2$)$_2$OEt | 1 | F | |
| 1-1308 | CH$_2$OCH$_2$OEt | (CH$_2$)$_2$OCH$_2$-c-Pr | 1 | F | |
| 1-1309 | CH$_2$OCH$_2$OEt | c-Pr | 2 | F | |
| 1-1310 | CH$_2$OCH$_2$OEt | CH$_2$-c-Pr | 2 | F | |
| 1-1311 | CH$_2$OCH$_2$OEt | (CH$_2$)$_2$OMe | 2 | F | |
| 1-1312 | CH$_2$OCH$_2$OEt | (CH$_2$)$_3$OMe | 2 | F | |
| 1-1313 | CH$_2$OCH$_2$OEt | (CH$_2$)$_2$OEt | 2 | F | |
| 1-1314 | CH$_2$OCH$_2$OEt | (CH$_2$)$_2$OCH$_2$-c-Pr | 2 | F | |
| 1-1315 | CH$_2$O(CH$_2$)$_2$SO$_2$Me | c-Pr | 0 | F | |
| 1-1316 | CH$_2$O(CH$_2$)$_2$SO$_2$Me | CH$_2$-c-Pr | 0 | F | |
| 1-1317 | CH$_2$O(CH$_2$)$_2$SO$_2$Me | (CH$_2$)$_2$OMe | 0 | F | |
| 1-1318 | CH$_2$O(CH$_2$)$_2$SO$_2$Me | (CH$_2$)$_3$OMe | 0 | F | |
| 1-1319 | CH$_2$O(CH$_2$)$_2$SO$_2$Me | (CH$_2$)$_2$OEt | 0 | F | |
| 1-1320 | CH$_2$O(CH$_2$)$_2$SO$_2$Me | (CH$_2$)$_2$OCH$_2$-c-Pr | 0 | F | |
| 1-1321 | CH$_2$O(CH$_2$)$_2$SO$_2$Me | c-Pr | 1 | F | |
| 1-1322 | CH$_2$O(CH$_2$)$_2$SO$_2$Me | CH$_2$-c-Pr | 1 | F | |
| 1-1323 | CH$_2$O(CH$_2$)$_2$SO$_2$Me | (CH$_2$)$_2$OMe | 1 | F | |
| 1-1324 | CH$_2$O(CH$_2$)$_2$SO$_2$Me | (CH$_2$)$_3$OMe | 1 | F | |
| 1-1325 | CH$_2$O(CH$_2$)$_2$SO$_2$Me | (CH$_2$)$_2$OEt | 1 | F | |
| 1-1326 | CH$_2$O(CH$_2$)$_2$SO$_2$Me | (CH$_2$)$_2$OCH$_2$-c-Pr | 1 | F | |
| 1-1327 | CH$_2$O(CH$_2$)$_2$SO$_2$Me | c-Pr | 2 | F | |
| 1-1328 | CH$_2$O(CH$_2$)$_2$SO$_2$Me | CH$_2$-c-Pr | 2 | F | |
| 1-1329 | CH$_2$O(CH$_2$)$_2$SO$_2$Me | (CH$_2$)$_2$OMe | 2 | F | |
| 1-1330 | CH$_2$O(CH$_2$)$_2$SO$_2$Me | (CH$_2$)$_3$OMe | 2 | F | |
| 1-1331 | CH$_2$O(CH$_2$)$_2$SO$_2$Me | (CH$_2$)$_2$OEt | 2 | F | |
| 1-1332 | CH$_2$O(CH$_2$)$_2$SO$_2$Me | (CH$_2$)$_2$OCH$_2$-c-Pr | 2 | F | |
| 1-1333 | CH$_2$SO$_2$(CH$_2$)$_2$OMe | c-Pr | 0 | F | |
| 1-1334 | CH$_2$SO$_2$(CH$_2$)$_2$OMe | CH$_2$-c-Pr | 0 | F | |
| 1-1335 | CH$_2$SO$_2$(CH$_2$)$_2$OMe | (CH$_2$)$_2$OMe | 0 | F | |
| 1-1336 | CH$_2$SO$_2$(CH$_2$)$_2$OMe | (CH$_2$)$_3$OMe | 0 | F | |
| 1-1337 | CH$_2$SO$_2$(CH$_2$)$_2$OMe | (CH$_2$)$_2$OEt | 0 | F | |
| 1-1338 | CH$_2$SO$_2$(CH$_2$)$_2$OMe | (CH$_2$)$_2$OCH$_2$-c-Pr | 0 | F | |
| 1-1339 | CH$_2$SO$_2$(CH$_2$)$_2$OMe | c-Pr | 1 | F | |
| 1-1340 | CH$_2$SO$_2$(CH$_2$)$_2$OMe | CH$_2$-c-Pr | 1 | F | |
| 1-1341 | CH$_2$SO$_2$(CH$_2$)$_2$OMe | (CH$_2$)$_2$OMe | 1 | F | |
| 1-1342 | CH$_2$SO$_2$(CH$_2$)$_2$OMe | (CH$_2$)$_3$OMe | 1 | F | |
| 1-1343 | CH$_2$SO$_2$(CH$_2$)$_2$OMe | (CH$_2$)$_2$OEt | 1 | F | |
| 1-1344 | CH$_2$SO$_2$(CH$_2$)$_2$OMe | (CH$_2$)$_2$OCH$_2$-c-Pr | 1 | F | |
| 1-1345 | CH$_2$SO$_2$(CH$_2$)$_2$OMe | c-Pr | 2 | F | |
| 1-1346 | CH$_2$SO$_2$(CH$_2$)$_2$OMe | CH$_2$-c-Pr | 2 | F | |

TABLE A-continued

Compounds according to the invention of the general formula (I) in which $R^1$ is methyl, $R^4$ is hydrogen and q is zero

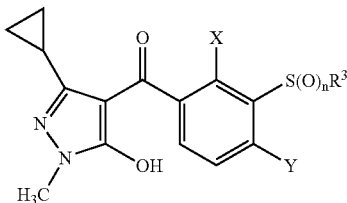

| No. | X | $R^3$ | n | Y | Physical data: $^1$H-NMR: δ[CDCl$_3$] |
|---|---|---|---|---|---|
| 1-1347 | CH$_2$SO$_2$(CH$_2$)$_2$OMe | (CH$_2$)$_2$OMe | 2 | F | |
| 1-1348 | CH$_2$SO$_2$(CH$_2$)$_2$OMe | (CH$_2$)$_3$OMe | 2 | F | |
| 1-1349 | CH$_2$SO$_2$(CH$_2$)$_2$OMe | (CH$_2$)$_2$OEt | 2 | F | |
| 1-1350 | CH$_2$SO$_2$(CH$_2$)$_2$OMe | (CH$_2$)$_2$OCH$_2$-c-Pr | 2 | F | |
| 1-1351 | CH$_2$SO$_2$(CH$_2$)$_2$SO$_2$Me | c-Pr | 0 | F | |
| 1-1352 | CH$_2$SO$_2$(CH$_2$)$_2$SO$_2$Me | CH$_2$-c-Pr | 0 | F | |
| 1-1353 | CH$_2$SO$_2$(CH$_2$)$_2$SO$_2$Me | (CH$_2$)$_2$OMe | 0 | F | |
| 1-1354 | CH$_2$SO$_2$(CH$_2$)$_2$SO$_2$Me | (CH$_2$)$_3$OMe | 0 | F | |
| 1-1355 | CH$_2$SO$_2$(CH$_2$)$_2$SO$_2$Me | (CH$_2$)$_2$OEt | 0 | F | |
| 1-1356 | CH$_2$SO$_2$(CH$_2$)$_2$SO$_2$Me | (CH$_2$)$_2$OCH$_2$-c-Pr | 0 | F | |
| 1-1357 | CH$_2$SO$_2$(CH$_2$)$_2$SO$_2$Me | c-Pr | 1 | F | |
| 1-1358 | CH$_2$SO$_2$(CH$_2$)$_2$SO$_2$Me | CH$_2$-c-Pr | 1 | F | |
| 1-1359 | CH$_2$SO$_2$(CH$_2$)$_2$SO$_2$Me | (CH$_2$)$_2$OMe | 1 | F | |
| 1-1360 | CH$_2$SO$_2$(CH$_2$)$_2$SO$_2$Me | (CH$_2$)$_3$OMe | 1 | F | |
| 1-1361 | CH$_2$SO$_2$(CH$_2$)$_2$SO$_2$Me | (CH$_2$)$_2$OEt | 1 | F | |
| 1-1362 | CH$_2$SO$_2$(CH$_2$)$_2$SO$_2$Me | (CH$_2$)$_2$OCH$_2$-c-Pr | 1 | F | |
| 1-1363 | CH$_2$SO$_2$(CH$_2$)$_2$SO$_2$Me | c-Pr | 2 | F | |
| 1-1364 | CH$_2$SO$_2$(CH$_2$)$_2$SO$_2$Me | CH$_2$-c-Pr | 2 | F | |
| 1-1365 | CH$_2$SO$_2$(CH$_2$)$_2$SO$_2$Me | (CH$_2$)$_2$OMe | 2 | F | |
| 1-1366 | CH$_2$SO$_2$(CH$_2$)$_2$SO$_2$Me | (CH$_2$)$_3$OMe | 2 | F | |
| 1-1367 | CH$_2$SO$_2$(CH$_2$)$_2$SO$_2$Me | (CH$_2$)$_2$OEt | 2 | F | |
| 1-1368 | CH$_2$SO$_2$(CH$_2$)$_2$SO$_2$Me | (CH$_2$)$_2$OCH$_2$-c-Pr | 2 | F | |
| 1-1369 | Cl | c-Pr | 0 | Cl | |
| 1-1370 | Cl | CH$_2$-c-Pr | 0 | Cl | 7.48 (d, 1H), 7.25 (d, 1H), 3.60 (s, 3H), 2.84 (d, 2H), 1.02-0.95 (m, 2H), 0.77 (m, 2H), 0.52-0.45 (m, 4H), 0.15 (m, 2H) |
| 1-1371 | Cl | (CH$_2$)$_2$OMe | 0 | Cl | |
| 1-1372 | Cl | (CH$_2$)$_3$OMe | 0 | Cl | |
| 1-1373 | Cl | (CH$_2$)$_2$OEt | 0 | Cl | |
| 1-1374 | Cl | (CH$_2$)$_2$OCH$_2$-c-Pr | 0 | Cl | |
| 1-1375 | Cl | c-Pr | 1 | Cl | |
| 1-1376 | Cl | CH$_2$-c-Pr | 1 | Cl | |
| 1-1377 | Cl | (CH$_2$)$_2$OMe | 1 | Cl | |
| 1-1378 | Cl | (CH$_2$)$_3$OMe | 1 | Cl | |
| 1-1379 | Cl | (CH$_2$)$_2$OEt | 1 | Cl | |
| 1-1380 | Cl | (CH$_2$)$_2$OCH$_2$-c-Pr | 1 | Cl | |
| 1-1381 | Cl | c-Pr | 2 | Cl | |
| 1-1382 | Cl | CH$_2$-c-Pr | 2 | Cl | 7.62 (d, 1H), 7.44 (d, 1H), 3.61 (s, 3H), 3.38 (d, 2H), 1.15 (m, 1H), 0.97 (m, 1H), 0.79 (m, 2H), 0.68-0.52 (m, 4H), 0.28 (m, 2H) |
| 1-1383 | Cl | (CH$_2$)$_2$OMe | 2 | Cl | |
| 1-1384 | Cl | (CH$_2$)$_3$OMe | 2 | Cl | |
| 1-1385 | Cl | (CH$_2$)$_2$OEt | 2 | Cl | |
| 1-1386 | Cl | (CH$_2$)$_2$OCH$_2$-c-Pr | 2 | Cl | |
| 1-1387 | Br | c-Pr | 0 | Cl | |
| 1-1388 | Br | CH$_2$-c-Pr | 0 | Cl | |
| 1-1389 | Br | (CH$_2$)$_2$OMe | 0 | Cl | |
| 1-1390 | Br | (CH$_2$)$_3$OMe | 0 | Cl | |
| 1-1391 | Br | (CH$_2$)$_2$OEt | 0 | Cl | |
| 1-1392 | Br | (CH$_2$)$_2$OCH$_2$-c-Pr | 0 | Cl | |
| 1-1393 | Br | c-Pr | 1 | Cl | |
| 1-1394 | Br | CH$_2$-c-Pr | 1 | Cl | |
| 1-1395 | Br | (CH$_2$)$_2$OMe | 1 | Cl | |
| 1-1396 | Br | (CH$_2$)$_3$OMe | 1 | Cl | |
| 1-1397 | Br | (CH$_2$)$_2$OEt | 1 | Cl | |
| 1-1398 | Br | (CH$_2$)$_2$OCH$_2$-c-Pr | 1 | Cl | |
| 1-1399 | Br | c-Pr | 2 | Cl | |
| 1-1400 | Br | CH$_2$-c-Pr | 2 | Cl | |
| 1-1401 | Br | (CH$_2$)$_2$OMe | 2 | Cl | |

TABLE A-continued

Compounds according to the invention of the general formula (I) in which R$^1$ is methyl, R$^4$ is hydrogen and q is zero

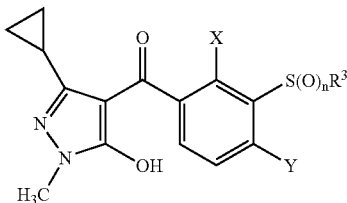

| No. | X | R$^3$ | n | Y | Physical data: $^1$H-NMR: δ[CDCl$_3$] |
|---|---|---|---|---|---|
| 1-1402 | Br | (CH$_2$)$_3$OMe | 2 | Cl | |
| 1-1403 | Br | (CH$_2$)$_2$OEt | 2 | Cl | |
| 1-1404 | Br | (CH$_2$)$_2$OCH$_2$-c-Pr | 2 | Cl | |
| 1-1405 | Me | c-Pr | 0 | Cl | |
| 1-1406 | Me | CH$_2$-c-Pr | 0 | Cl | 7.40 (d, 1H), 7.21 (d, 1H), 3.58 (s, 3H), 2.75 (d, 2H), 2.62 (s, 3H), 0.99-0.90 (m, 2H), 0.77 (m, 2H), 0.51 (m, 4H), 0.13 (m, 2H) |
| 1-1407 | Me | (CH$_2$)$_2$OMe | 0 | Cl | 7.41 (d, 1H), 7.22 (d, 1H), 3.59 (s, 3H), 3.47 (t, 2H), 3.31 (s, 3H), 3.02 (t, 2H), 2.60 (s, 3H), 0.94 (m, 1H), 0.77 (m, 2H), 0.52 (m, 2H) |
| 1-1408 | Me | (CH$_2$)$_3$OMe | 0 | Cl | |
| 1-1409 | Me | (CH$_2$)$_2$OEt | 0 | Cl | |
| 1-1410 | Me | (CH$_2$)$_2$OCH$_2$-c-Pr | 0 | Cl | |
| 1-1411 | Me | c-Pr | 1 | Cl | |
| 1-1412 | Me | CH$_2$-c-Pr | 1 | Cl | |
| 1-1413 | Me | (CH$_2$)$_2$OMe | 1 | Cl | 7.33 (s, 2H), 3.92 (m, 1H), 3.76 (m, 1H), 3.60-3.54 (m, 1H), 3.59 (s, 3H), 3.39 (s, 3H), 3.32 (m, 1H), 2.64 (s, 3H), 0.94 (m, 1H), 0.79 (m, 2H), 0.57 (m, 2H) |
| 1-1414 | Me | (CH$_2$)$_3$OMe | 1 | Cl | |
| 1-1415 | Me | (CH$_2$)$_2$OEt | 1 | Cl | |
| 1-1416 | Me | (CH$_2$)$_2$OCH$_2$-c-Pr | 1 | Cl | |
| 1-1417 | Me | c-Pr | 2 | Cl | |
| 1-1418 | Me | CH$_2$-c-Pr | 2 | Cl | 7.51 (d, 1H), 7.41 (d, 1H), 3.60 (s, 3H), 3.37 (d, 2H), 2.77 (s, 3H), 1.08 (m, 1H), 0.88 (m, 1H), 0.78 (m, 2H), 0.62-0.51 (m, 4H), 0.26 (m, 2H) |
| 1-1419 | Me | (CH$_2$)$_2$OMe | 2 | Cl | 7.51 (d, 1H), 7.39 (d, 1H), 3.83 (t, 2H), 3.71 (t, 2H), 3.59 (s, 3H), 3.22 (s, 3H), 2.72 (s, 3H), 0.88 (m, 1H), 0.78 (m, 2H), 0.54 (m, 2H) |
| 1-1420 | Me | (CH$_2$)$_3$OMe | 2 | Cl | |
| 1-1421 | Me | (CH$_2$)$_2$OEt | 2 | Cl | |
| 1-1422 | Me | (CH$_2$)$_2$OCH$_2$-c-Pr | 2 | Cl | |
| 1-1423 | Et | c-Pr | 0 | Cl | |
| 1-1424 | Et | CH$_2$-c-Pr | 0 | Cl | |
| 1-1425 | Et | (CH$_2$)$_2$OMe | 0 | Cl | |
| 1-1426 | Et | (CH$_2$)$_3$OMe | 0 | Cl | |
| 1-1427 | Et | (CH$_2$)$_2$OEt | 0 | Cl | |
| 1-1428 | Et | (CH$_2$)$_2$OCH$_2$-c-Pr | 0 | Cl | |
| 1-1429 | Et | c-Pr | 1 | Cl | |
| 1-1430 | Et | CH$_2$-c-Pr | 1 | Cl | |
| 1-1431 | Et | (CH$_2$)$_2$OMe | 1 | Cl | |
| 1-1432 | Et | (CH$_2$)$_3$OMe | 1 | Cl | |
| 1-1433 | Et | (CH$_2$)$_2$OEt | 1 | Cl | |
| 1-1434 | Et | (CH$_2$)$_2$OCH$_2$-c-Pr | 1 | Cl | |
| 1-1435 | Et | c-Pr | 2 | Cl | |
| 1-1436 | Et | CH$_2$-c-Pr | 2 | Cl | |
| 1-1437 | Et | (CH$_2$)$_2$OMe | 2 | Cl | |
| 1-1438 | Et | (CH$_2$)$_3$OMe | 2 | Cl | |
| 1-1439 | Et | (CH$_2$)$_2$OEt | 2 | Cl | |
| 1-1440 | Et | (CH$_2$)$_2$OCH$_2$-c-Pr | 2 | Cl | |
| 1-1441 | CF$_3$ | c-Pr | 0 | Cl | |
| 1-1442 | CF$_3$ | CH$_2$-c-Pr | 0 | Cl | |
| 1-1443 | CF$_3$ | (CH$_2$)$_2$OMe | 0 | Cl | |

TABLE A-continued

Compounds according to the invention of the general formula (I) in which $R^1$ is methyl, $R^4$ is hydrogen and q is zero

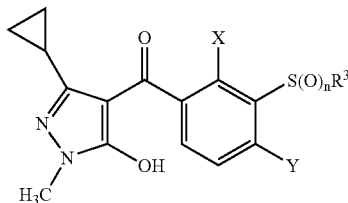

| No. | X | $R^3$ | n | Y | Physical data: $^1$H-NMR: δ[CDCl$_3$] |
|---|---|---|---|---|---|
| 1-1444 | CF$_3$ | (CH$_2$)$_3$OMe | 0 | Cl | |
| 1-1445 | CF$_3$ | (CH$_2$)$_2$OEt | 0 | Cl | |
| 1-1446 | CF$_3$ | (CH$_2$)$_2$OCH$_2$-c-Pr | 0 | Cl | |
| 1-1447 | CF$_3$ | c-Pr | 1 | Cl | |
| 1-1448 | CF$_3$ | CH$_2$-c-Pr | 1 | Cl | |
| 1-1449 | CF$_3$ | (CH$_2$)$_2$OMe | 1 | Cl | |
| 1-1450 | CF$_3$ | (CH$_2$)$_3$OMe | 1 | Cl | |
| 1-1451 | CF$_3$ | (CH$_2$)$_2$OEt | 1 | Cl | |
| 1-1452 | CF$_3$ | (CH$_2$)$_2$OCH$_2$-c-Pr | 1 | Cl | |
| 1-1453 | CF$_3$ | c-Pr | 2 | Cl | |
| 1-1454 | CF$_3$ | CH$_2$-c-Pr | 2 | Cl | |
| 1-1455 | CF$_3$ | (CH$_2$)$_2$OMe | 2 | Cl | |
| 1-1456 | CF$_3$ | (CH$_2$)$_3$OMe | 2 | Cl | |
| 1-1457 | CF$_3$ | (CH$_2$)$_2$OEt | 2 | Cl | |
| 1-1458 | CF$_3$ | (CH$_2$)$_2$OCH$_2$-c-Pr | 2 | Cl | |
| 1-1459 | OMe | c-Pr | 0 | Cl | |
| 1-1460 | OMe | CH$_2$-c-Pr | 0 | Cl | |
| 1-1461 | OMe | (CH$_2$)$_2$OMe | 0 | Cl | |
| 1-1462 | OMe | (CH$_2$)$_3$OMe | 0 | Cl | |
| 1-1463 | OMe | (CH$_2$)$_2$OEt | 0 | Cl | |
| 1-1464 | OMe | (CH$_2$)$_2$OCH$_2$-c-Pr | 0 | Cl | |
| 1-1465 | OMe | c-Pr | 1 | Cl | |
| 1-1466 | OMe | CH$_2$-c-Pr | 1 | Cl | |
| 1-1467 | OMe | (CH$_2$)$_2$OMe | 1 | Cl | |
| 1-1468 | OMe | (CH$_2$)$_3$OMe | 1 | Cl | |
| 1-1469 | OMe | (CH$_2$)$_2$OEt | 1 | Cl | |
| 1-1470 | OMe | (CH$_2$)$_2$OCH$_2$-c-Pr | 1 | Cl | |
| 1-1471 | OMe | c-Pr | 2 | Cl | |
| 1-1472 | OMe | CH$_2$-c-Pr | 2 | Cl | |
| 1-1473 | OMe | (CH$_2$)$_2$OMe | 2 | Cl | |
| 1-1474 | OMe | (CH$_2$)$_3$OMe | 2 | Cl | |
| 1-1475 | OMe | (CH$_2$)$_2$OEt | 2 | Cl | |
| 1-1476 | OMe | (CH$_2$)$_2$OCH$_2$-c-Pr | 2 | Cl | |
| 1-1477 | OEt | c-Pr | 0 | Cl | |
| 1-1478 | OEt | CH$_2$-c-Pr | 0 | Cl | |
| 1-1479 | OEt | (CH$_2$)$_2$OMe | 0 | Cl | |
| 1-1480 | OEt | (CH$_2$)$_3$OMe | 0 | Cl | |
| 1-1481 | OEt | (CH$_2$)$_2$OEt | 0 | Cl | |
| 1-1482 | OEt | (CH$_2$)$_2$OCH$_2$-c-Pr | 0 | Cl | |
| 1-1483 | OEt | c-Pr | 1 | Cl | |
| 1-1484 | OEt | CH$_2$-c-Pr | 1 | Cl | |
| 1-1485 | OEt | (CH$_2$)$_2$OMe | 1 | Cl | |
| 1-1486 | OEt | (CH$_2$)$_3$OMe | 1 | Cl | |
| 1-1487 | OEt | (CH$_2$)$_2$OEt | 1 | Cl | |
| 1-1488 | OEt | (CH$_2$)$_2$OCH$_2$-c-Pr | 1 | Cl | |
| 1-1489 | OEt | c-Pr | 2 | Cl | |
| 1-1490 | OEt | CH$_2$-c-Pr | 2 | Cl | |
| 1-1491 | OEt | (CH$_2$)$_2$OMe | 2 | Cl | |
| 1-1492 | OEt | (CH$_2$)$_3$OMe | 2 | Cl | |
| 1-1493 | OEt | (CH$_2$)$_2$OEt | 2 | Cl | |
| 1-1494 | OEt | (CH$_2$)$_2$OCH$_2$-c-Pr | 2 | Cl | |
| 1-1495 | NO$_2$ | c-Pr | 0 | Cl | |
| 1-1496 | NO$_2$ | CH$_2$-c-Pr | 0 | Cl | |
| 1-1497 | NO$_2$ | (CH$_2$)$_2$OMe | 0 | Cl | |
| 1-1498 | NO$_2$ | (CH$_2$)$_3$OMe | 0 | Cl | |
| 1-1499 | NO$_2$ | (CH$_2$)$_2$OEt | 0 | Cl | |
| 1-1500 | NO$_2$ | (CH$_2$)$_2$OCH$_2$-c-Pr | 0 | Cl | |
| 1-1501 | NO$_2$ | c-Pr | 1 | Cl | |
| 1-1502 | NO$_2$ | CH$_2$-c-Pr | 1 | Cl | |
| 1-1503 | NO$_2$ | (CH$_2$)$_2$OMe | 1 | Cl | |
| 1-1504 | NO$_2$ | (CH$_2$)$_3$OMe | 1 | Cl | |
| 1-1505 | NO$_2$ | (CH$_2$)$_2$OEt | 1 | Cl | |
| 1-1506 | NO$_2$ | (CH$_2$)$_2$OCH$_2$-c-Pr | 1 | Cl | |

TABLE A-continued

Compounds according to the invention of the general formula (I) in which $R^1$ is methyl, $R^4$ is hydrogen and q is zero

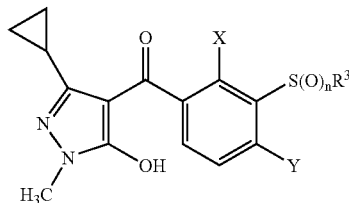

| No. | X | $R^3$ | n | Y | Physical data: $^1$H-NMR: δ[CDCl$_3$] |
|---|---|---|---|---|---|
| 1-1507 | NO$_2$ | c-Pr | 2 | Cl | |
| 1-1508 | NO$_2$ | CH$_2$-c-Pr | 2 | Cl | |
| 1-1509 | NO$_2$ | (CH$_2$)$_2$OMe | 2 | Cl | |
| 1-1510 | NO$_2$ | (CH$_2$)$_3$OMe | 2 | Cl | |
| 1-1511 | NO$_2$ | (CH$_2$)$_2$OEt | 2 | Cl | |
| 1-1512 | NO$_2$ | (CH$_2$)$_2$OCH$_2$-c-Pr | 2 | Cl | |
| 1-1513 | SO$_2$Me | c-Pr | 0 | Cl | |
| 1-1514 | SO$_2$Me | CH$_2$-c-Pr | 0 | Cl | |
| 1-1515 | SO$_2$Me | (CH$_2$)$_2$OMe | 0 | Cl | |
| 1-1516 | SO$_2$Me | (CH$_2$)$_3$OMe | 0 | Cl | |
| 1-1517 | SO$_2$Me | (CH$_2$)$_2$OEt | 0 | Cl | |
| 1-1518 | SO$_2$Me | (CH$_2$)$_2$OCH$_2$-c-Pr | 0 | Cl | |
| 1-1519 | SO$_2$Me | c-Pr | 1 | Cl | |
| 1-1520 | SO$_2$Me | CH$_2$-c-Pr | 1 | Cl | |
| 1-1521 | SO$_2$Me | (CH$_2$)$_2$OMe | 1 | Cl | |
| 1-1522 | SO$_2$Me | (CH$_2$)$_3$OMe | 1 | Cl | |
| 1-1523 | SO$_2$Me | (CH$_2$)$_2$OEt | 1 | Cl | |
| 1-1524 | SO$_2$Me | (CH$_2$)$_2$OCH$_2$-c-Pr | 1 | Cl | |
| 1-1525 | SO$_2$Me | c-Pr | 2 | Cl | |
| 1-1526 | SO$_2$Me | CH$_2$-c-Pr | 2 | Cl | |
| 1-1527 | SO$_2$Me | (CH$_2$)$_2$OMe | 2 | Cl | |
| 1-1528 | SO$_2$Me | (CH$_2$)$_3$OMe | 2 | Cl | |
| 1-1529 | SO$_2$Me | (CH$_2$)$_2$OEt | 2 | Cl | |
| 1-1530 | SO$_2$Me | (CH$_2$)$_2$OCH$_2$-c-Pr | 2 | Cl | |
| 1-1531 | CH$_2$OMe | c-Pr | 0 | Cl | |
| 1-1532 | CH$_2$OMe | CH$_2$-c-Pr | 0 | Cl | |
| 1-1533 | CH$_2$OMe | (CH$_2$)$_2$OMe | 0 | Cl | |
| 1-1534 | CH$_2$OMe | (CH$_2$)$_3$OMe | 0 | Cl | |
| 1-1535 | CH$_2$OMe | (CH$_2$)$_2$OEt | 0 | Cl | |
| 1-1536 | CH$_2$OMe | (CH$_2$)$_2$OCH$_2$-c-Pr | 0 | Cl | |
| 1-1537 | CH$_2$OMe | c-Pr | 1 | Cl | |
| 1-1538 | CH$_2$OMe | CH$_2$-c-Pr | 1 | Cl | |
| 1-1539 | CH$_2$OMe | (CH$_2$)$_2$OMe | 1 | Cl | |
| 1-1540 | CH$_2$OMe | (CH$_2$)$_3$OMe | 1 | Cl | |
| 1-1541 | CH$_2$OMe | (CH$_2$)$_2$OEt | 1 | Cl | |
| 1-1542 | CH$_2$OMe | (CH$_2$)$_2$OCH$_2$-c-Pr | 1 | Cl | |
| 1-1543 | CH$_2$OMe | c-Pr | 2 | Cl | |
| 1-1544 | CH$_2$OMe | CH$_2$-c-Pr | 2 | Cl | |
| 1-1545 | CH$_2$OMe | (CH$_2$)$_2$OMe | 2 | Cl | |
| 1-1546 | CH$_2$OMe | (CH$_2$)$_3$OMe | 2 | Cl | |
| 1-1547 | CH$_2$OMe | (CH$_2$)$_2$OEt | 2 | Cl | |
| 1-1548 | CH$_2$OMe | (CH$_2$)$_2$OCH$_2$-c-Pr | 2 | Cl | |
| 1-1549 | CH$_2$SO$_2$Me | c-Pr | 0 | Cl | |
| 1-1550 | CH$_2$SO$_2$Me | CH$_2$-c-Pr | 0 | Cl | |
| 1-1551 | CH$_2$SO$_2$Me | (CH$_2$)$_2$OMe | 0 | Cl | |
| 1-1552 | CH$_2$SO$_2$Me | (CH$_2$)$_3$OMe | 0 | Cl | |
| 1-1553 | CH$_2$SO$_2$Me | (CH$_2$)$_2$OEt | 0 | Cl | |
| 1-1554 | CH$_2$SO$_2$Me | (CH$_2$)$_2$OCH$_2$-c-Pr | 0 | Cl | |
| 1-1555 | CH$_2$SO$_2$Me | c-Pr | 1 | Cl | |
| 1-1556 | CH$_2$SO$_2$Me | CH$_2$-c-Pr | 1 | Cl | |
| 1-1557 | CH$_2$SO$_2$Me | (CH$_2$)$_2$OMe | 1 | Cl | |
| 1-1558 | CH$_2$SO$_2$Me | (CH$_2$)$_3$OMe | 1 | Cl | |
| 1-1559 | CH$_2$SO$_2$Me | (CH$_2$)$_2$OEt | 1 | Cl | |
| 1-1560 | CH$_2$SO$_2$Me | (CH$_2$)$_2$OCH$_2$-c-Pr | 1 | Cl | |
| 1-1561 | CH$_2$SO$_2$Me | c-Pr | 2 | Cl | |
| 1-1562 | CH$_2$SO$_2$Me | CH$_2$-c-Pr | 2 | Cl | |
| 1-1563 | CH$_2$SO$_2$Me | (CH$_2$)$_2$OMe | 2 | Cl | |
| 1-1564 | CH$_2$SO$_2$Me | (CH$_2$)$_3$OMe | 2 | Cl | |
| 1-1565 | CH$_2$SO$_2$Me | (CH$_2$)$_2$OEt | 2 | Cl | |
| 1-1566 | CH$_2$SO$_2$Me | (CH$_2$)$_2$OCH$_2$-c-Pr | 2 | Cl | |
| 1-1567 | CH$_2$O(CH$_2$)$_2$OMe | c-Pr | 0 | Cl | |
| 1-1568 | CH$_2$O(CH$_2$)$_2$OMe | CH$_2$-c-Pr | 0 | Cl | |
| 1-1569 | CH$_2$O(CH$_2$)$_2$OMe | (CH$_2$)$_2$OMe | 0 | Cl | |

TABLE A-continued

Compounds according to the invention of the general formula (I) in which $R^1$ is methyl, $R^4$ is hydrogen and q is zero

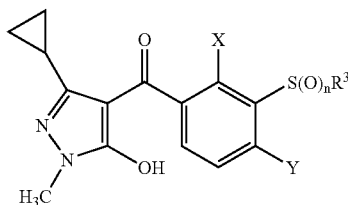

| No. | X | $R^3$ | n | Y | Physical data: $^1$H-NMR: δ[CDCl$_3$] |
|---|---|---|---|---|---|
| 1-1570 | CH$_2$O(CH$_2$)$_2$OMe | (CH$_2$)$_3$OMe | 0 | Cl | |
| 1-1571 | CH$_2$O(CH$_2$)$_2$OMe | (CH$_2$)$_2$OEt | 0 | Cl | |
| 1-1572 | CH$_2$O(CH$_2$)$_2$OMe | (CH$_2$)$_2$OCH$_2$-c-Pr | 0 | Cl | |
| 1-1573 | CH$_2$O(CH$_2$)$_2$OMe | c-Pr | 1 | Cl | |
| 1-1574 | CH$_2$O(CH$_2$)$_2$OMe | CH$_2$-c-Pr | 1 | Cl | |
| 1-1575 | CH$_2$O(CH$_2$)$_2$OMe | (CH$_2$)$_2$OMe | 1 | Cl | |
| 1-1576 | CH$_2$O(CH$_2$)$_2$OMe | (CH$_2$)$_3$OMe | 1 | Cl | |
| 1-1577 | CH$_2$O(CH$_2$)$_2$OMe | (CH$_2$)$_2$OEt | 1 | Cl | |
| 1-1578 | CH$_2$O(CH$_2$)$_2$OMe | (CH$_2$)$_2$OCH$_2$-c-Pr | 1 | Cl | |
| 1-1579 | CH$_2$O(CH$_2$)$_2$OMe | c-Pr | 2 | Cl | |
| 1-1580 | CH$_2$O(CH$_2$)$_2$OMe | CH$_2$-c-Pr | 2 | Cl | |
| 1-1581 | CH$_2$O(CH$_2$)$_2$OMe | (CH$_2$)$_2$OMe | 2 | Cl | |
| 1-1582 | CH$_2$O(CH$_2$)$_2$OMe | (CH$_2$)$_3$OMe | 2 | Cl | |
| 1-1583 | CH$_2$O(CH$_2$)$_2$OMe | (CH$_2$)$_2$OEt | 2 | Cl | |
| 1-1584 | CH$_2$O(CH$_2$)$_2$OMe | (CH$_2$)$_2$OCH$_2$-c-Pr | 2 | Cl | |
| 1-1585 | CH$_2$O(CH$_2$)$_2$OEt | c-Pr | 0 | Cl | |
| 1-1586 | CH$_2$O(CH$_2$)$_2$OEt | CH$_2$-c-Pr | 0 | Cl | |
| 1-1587 | CH$_2$O(CH$_2$)$_2$OEt | (CH$_2$)$_2$OMe | 0 | Cl | |
| 1-1588 | CH$_2$O(CH$_2$)$_2$OEt | (CH$_2$)$_3$OMe | 0 | Cl | |
| 1-1589 | CH$_2$O(CH$_2$)$_2$OEt | (CH$_2$)$_2$OEt | 0 | Cl | |
| 1-1590 | CH$_2$O(CH$_2$)$_2$OEt | (CH$_2$)$_2$OCH$_2$-c-Pr | 0 | Cl | |
| 1-1591 | CH$_2$O(CH$_2$)$_2$OEt | c-Pr | 1 | Cl | |
| 1-1592 | CH$_2$O(CH$_2$)$_2$OEt | CH$_2$-c-Pr | 1 | Cl | |
| 1-1593 | CH$_2$O(CH$_2$)$_2$OEt | (CH$_2$)$_2$OMe | 1 | Cl | |
| 1-1594 | CH$_2$O(CH$_2$)$_2$OEt | (CH$_2$)$_3$OMe | 1 | Cl | |
| 1-1595 | CH$_2$O(CH$_2$)$_2$OEt | (CH$_2$)$_2$OEt | 1 | Cl | |
| 1-1596 | CH$_2$O(CH$_2$)$_2$OEt | (CH$_2$)$_2$OCH$_2$-c-Pr | 1 | Cl | |
| 1-1597 | CH$_2$O(CH$_2$)$_2$OEt | c-Pr | 2 | Cl | |
| 1-1598 | CH$_2$O(CH$_2$)$_2$OEt | CH$_2$-c-Pr | 2 | Cl | |
| 1-1599 | CH$_2$O(CH$_2$)$_2$OEt | (CH$_2$)$_2$OMe | 2 | Cl | |
| 1-1600 | CH$_2$O(CH$_2$)$_2$OEt | (CH$_2$)$_3$OMe | 2 | Cl | |
| 1-1601 | CH$_2$O(CH$_2$)$_2$OEt | (CH$_2$)$_2$OEt | 2 | Cl | |
| 1-1602 | CH$_2$O(CH$_2$)$_2$OEt | (CH$_2$)$_2$OCH$_2$-c-Pr | 2 | Cl | |
| 1-1603 | CH$_2$O(CH$_2$)$_3$OMe | c-Pr | 0 | Cl | |
| 1-1604 | CH$_2$O(CH$_2$)$_3$OMe | CH$_2$-c-Pr | 0 | Cl | |
| 1-1605 | CH$_2$O(CH$_2$)$_3$OMe | (CH$_2$)$_2$OMe | 0 | Cl | |
| 1-1606 | CH$_2$O(CH$_2$)$_3$OMe | (CH$_2$)$_3$OMe | 0 | Cl | |
| 1-1607 | CH$_2$O(CH$_2$)$_3$OMe | (CH$_2$)$_2$OEt | 0 | Cl | |
| 1-1608 | CH$_2$O(CH$_2$)$_3$OMe | (CH$_2$)$_2$OCH$_2$-c-Pr | 0 | Cl | |
| 1-1609 | CH$_2$O(CH$_2$)$_3$OMe | c-Pr | 1 | Cl | |
| 1-1610 | CH$_2$O(CH$_2$)$_3$OMe | CH$_2$-c-Pr | 1 | Cl | |
| 1-1611 | CH$_2$O(CH$_2$)$_3$OMe | (CH$_2$)$_2$OMe | 1 | Cl | |
| 1-1612 | CH$_2$O(CH$_2$)$_3$OMe | (CH$_2$)$_3$OMe | 1 | Cl | |
| 1-1613 | CH$_2$O(CH$_2$)$_3$OMe | (CH$_2$)$_2$OEt | 1 | Cl | |
| 1-1614 | CH$_2$O(CH$_2$)$_3$OMe | (CH$_2$)$_2$OCH$_2$-c-Pr | 1 | Cl | |
| 1-1615 | CH$_2$O(CH$_2$)$_3$OMe | c-Pr | 2 | Cl | |
| 1-1616 | CH$_2$O(CH$_2$)$_3$OMe | CH$_2$-c-Pr | 2 | Cl | |
| 1-1617 | CH$_2$O(CH$_2$)$_3$OMe | (CH$_2$)$_2$OMe | 2 | Cl | |
| 1-1618 | CH$_2$O(CH$_2$)$_3$OMe | (CH$_2$)$_3$OMe | 2 | Cl | |
| 1-1619 | CH$_2$O(CH$_2$)$_3$OMe | (CH$_2$)$_2$OEt | 2 | Cl | |
| 1-1620 | CH$_2$O(CH$_2$)$_3$OMe | (CH$_2$)$_2$OCH$_2$-c-Pr | 2 | Cl | |
| 1-1621 | CH$_2$OCH$_2$OMe | c-Pr | 0 | Cl | |
| 1-1622 | CH$_2$OCH$_2$OMe | CH$_2$-c-Pr | 0 | Cl | |
| 1-1623 | CH$_2$OCH$_2$OMe | (CH$_2$)$_2$OMe | 0 | Cl | |
| 1-1624 | CH$_2$OCH$_2$OMe | (CH$_2$)$_3$OMe | 0 | Cl | |
| 1-1625 | CH$_2$OCH$_2$OMe | (CH$_2$)$_2$OEt | 0 | Cl | |
| 1-1626 | CH$_2$OCH$_2$OMe | (CH$_2$)$_2$OCH$_2$-c-Pr | 0 | Cl | |
| 1-1627 | CH$_2$OCH$_2$OMe | c-Pr | 1 | Cl | |
| 1-1628 | CH$_2$OCH$_2$OMe | CH$_2$-c-Pr | 1 | Cl | |
| 1-1629 | CH$_2$OCH$_2$OMe | (CH$_2$)$_2$OMe | 1 | Cl | |
| 1-1630 | CH$_2$OCH$_2$OMe | (CH$_2$)$_3$OMe | 1 | Cl | |
| 1-1631 | CH$_2$OCH$_2$OMe | (CH$_2$)$_2$OEt | 1 | Cl | |
| 1-1632 | CH$_2$OCH$_2$OMe | (CH$_2$)$_2$OCH$_2$-c-Pr | 1 | Cl | |

TABLE A-continued

Compounds according to the invention of the general formula (I) in which $R^1$ is methyl, $R^4$ is hydrogen and q is zero

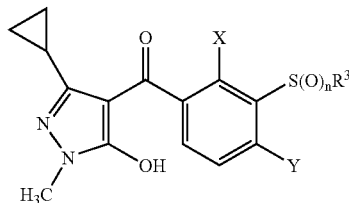

| No. | X | $R^3$ | n | Y | Physical data: $^1$H-NMR: δ[CDCl$_3$] |
|---|---|---|---|---|---|
| 1-1633 | CH$_2$OCH$_2$OMe | c-Pr | 2 | Cl | |
| 1-1634 | CH$_2$OCH$_2$OMe | CH$_2$-c-Pr | 2 | Cl | |
| 1-1635 | CH$_2$OCH$_2$OMe | (CH$_2$)$_2$OMe | 2 | Cl | |
| 1-1636 | CH$_2$OCH$_2$OMe | (CH$_2$)$_3$OMe | 2 | Cl | |
| 1-1637 | CH$_2$OCH$_2$OMe | (CH$_2$)$_2$OEt | 2 | Cl | |
| 1-1638 | CH$_2$OCH$_2$OMe | (CH$_2$)$_2$OCH$_2$-c-Pr | 2 | Cl | |
| 1-1639 | CH$_2$OCH$_2$OEt | c-Pr | 0 | Cl | |
| 1-1640 | CH$_2$OCH$_2$OEt | CH$_2$-c-Pr | 0 | Cl | |
| 1-1641 | CH$_2$OCH$_2$OEt | (CH$_2$)$_2$OMe | 0 | Cl | |
| 1-1642 | CH$_2$OCH$_2$OEt | (CH$_2$)$_3$OMe | 0 | Cl | |
| 1-1643 | CH$_2$OCH$_2$OEt | (CH$_2$)$_2$OEt | 0 | Cl | |
| 1-1644 | CH$_2$OCH$_2$OEt | (CH$_2$)$_2$OCH$_2$-c-Pr | 0 | Cl | |
| 1-1645 | CH$_2$OCH$_2$OEt | c-Pr | 1 | Cl | |
| 1-1646 | CH$_2$OCH$_2$OEt | CH$_2$-c-Pr | 1 | Cl | |
| 1-1647 | CH$_2$OCH$_2$OEt | (CH$_2$)$_2$OMe | 1 | Cl | |
| 1-1648 | CH$_2$OCH$_2$OEt | (CH$_2$)$_3$OMe | 1 | Cl | |
| 1-1649 | CH$_2$OCH$_2$OEt | (CH$_2$)$_2$OEt | 1 | Cl | |
| 1-1650 | CH$_2$OCH$_2$OEt | (CH$_2$)$_2$OCH$_2$-c-Pr | 1 | Cl | |
| 1-1651 | CH$_2$OCH$_2$OEt | c-Pr | 2 | Cl | |
| 1-1652 | CH$_2$OCH$_2$OEt | CH$_2$-c-Pr | 2 | Cl | |
| 1-1653 | CH$_2$OCH$_2$OEt | (CH$_2$)$_2$OMe | 2 | Cl | |
| 1-1654 | CH$_2$OCH$_2$OEt | (CH$_2$)$_3$OMe | 2 | Cl | |
| 1-1655 | CH$_2$OCH$_2$OEt | (CH$_2$)$_2$OEt | 2 | Cl | |
| 1-1656 | CH$_2$OCH$_2$OEt | (CH$_2$)$_2$OCH$_2$-c-Pr | 2 | Cl | |
| 1-1657 | CH$_2$O(CH$_2$)$_2$SO$_2$Me | c-Pr | 0 | Cl | |
| 1-1658 | CH$_2$O(CH$_2$)$_2$SO$_2$Me | CH$_2$-c-Pr | 0 | Cl | |
| 1-1659 | CH$_2$O(CH$_2$)$_2$SO$_2$Me | (CH$_2$)$_2$OMe | 0 | Cl | |
| 1-1660 | CH$_2$O(CH$_2$)$_2$SO$_2$Me | (CH$_2$)$_3$OMe | 0 | Cl | |
| 1-1661 | CH$_2$O(CH$_2$)$_2$SO$_2$Me | (CH$_2$)$_2$OEt | 0 | Cl | |
| 1-1662 | CH$_2$O(CH$_2$)$_2$SO$_2$Me | (CH$_2$)$_2$OCH$_2$-c-Pr | 0 | Cl | |
| 1-1663 | CH$_2$O(CH$_2$)$_2$SO$_2$Me | c-Pr | 1 | Cl | |
| 1-1664 | CH$_2$O(CH$_2$)$_2$SO$_2$Me | CH$_2$-c-Pr | 1 | Cl | |
| 1-1665 | CH$_2$O(CH$_2$)$_2$SO$_2$Me | (CH$_2$)$_2$OMe | 1 | Cl | |
| 1-1666 | CH$_2$O(CH$_2$)$_2$SO$_2$Me | (CH$_2$)$_3$OMe | 1 | Cl | |
| 1-1667 | CH$_2$O(CH$_2$)$_2$SO$_2$Me | (CH$_2$)$_2$OEt | 1 | Cl | |
| 1-1668 | CH$_2$O(CH$_2$)$_2$SO$_2$Me | (CH$_2$)$_2$OCH$_2$-c-Pr | 1 | Cl | |
| 1-1669 | CH$_2$O(CH$_2$)$_2$SO$_2$Me | c-Pr | 2 | Cl | |
| 1-1670 | CH$_2$O(CH$_2$)$_2$SO$_2$Me | CH$_2$-c-Pr | 2 | Cl | |
| 1-1671 | CH$_2$O(CH$_2$)$_2$SO$_2$Me | (CH$_2$)$_2$OMe | 2 | Cl | |
| 1-1672 | CH$_2$O(CH$_2$)$_2$SO$_2$Me | (CH$_2$)$_3$OMe | 2 | Cl | |
| 1-1673 | CH$_2$O(CH$_2$)$_2$SO$_2$Me | (CH$_2$)$_2$OEt | 2 | Cl | |
| 1-1674 | CH$_2$O(CH$_2$)$_2$SO$_2$Me | (CH$_2$)$_2$OCH$_2$-c-Pr | 2 | Cl | |
| 1-1675 | CH$_2$SO$_2$(CH$_2$)$_2$OMe | c-Pr | 0 | Cl | |
| 1-1676 | CH$_2$SO$_2$(CH$_2$)$_2$OMe | CH$_2$-c-Pr | 0 | Cl | |
| 1-1677 | CH$_2$SO$_2$(CH$_2$)$_2$OMe | (CH$_2$)$_2$OMe | 0 | Cl | |
| 1-1678 | CH$_2$SO$_2$(CH$_2$)$_2$OMe | (CH$_2$)$_3$OMe | 0 | Cl | |
| 1-1679 | CH$_2$SO$_2$(CH$_2$)$_2$OMe | (CH$_2$)$_2$OEt | 0 | Cl | |
| 1-1680 | CH$_2$SO$_2$(CH$_2$)$_2$OMe | (CH$_2$)$_2$OCH$_2$-c-Pr | 0 | Cl | |
| 1-1681 | CH$_2$SO$_2$(CH$_2$)$_2$OMe | c-Pr | 1 | Cl | |
| 1-1682 | CH$_2$SO$_2$(CH$_2$)$_2$OMe | CH$_2$-c-Pr | 1 | Cl | |
| 1-1683 | CH$_2$SO$_2$(CH$_2$)$_2$OMe | (CH$_2$)$_2$OMe | 1 | Cl | |
| 1-1684 | CH$_2$SO$_2$(CH$_2$)$_2$OMe | (CH$_2$)$_3$OMe | 1 | Cl | |
| 1-1685 | CH$_2$SO$_2$(CH$_2$)$_2$OMe | (CH$_2$)$_2$OEt | 1 | Cl | |
| 1-1686 | CH$_2$SO$_2$(CH$_2$)$_2$OMe | (CH$_2$)$_2$OCH$_2$-c-Pr | 1 | Cl | |
| 1-1687 | CH$_2$SO$_2$(CH$_2$)$_2$OMe | c-Pr | 2 | Cl | |
| 1-1688 | CH$_2$SO$_2$(CH$_2$)$_2$OMe | CH$_2$-c-Pr | 2 | Cl | |
| 1-1689 | CH$_2$SO$_2$(CH$_2$)$_2$OMe | (CH$_2$)$_2$OMe | 2 | Cl | |
| 1-1690 | CH$_2$SO$_2$(CH$_2$)$_2$OMe | (CH$_2$)$_3$OMe | 2 | Cl | |
| 1-1691 | CH$_2$SO$_2$(CH$_2$)$_2$OMe | (CH$_2$)$_2$OEt | 2 | Cl | |
| 1-1692 | CH$_2$SO$_2$(CH$_2$)$_2$OMe | (CH$_2$)$_2$OCH$_2$-c-Pr | 2 | Cl | |
| 1-1693 | CH$_2$SO$_2$(CH$_2$)$_2$SO$_2$Me | c-Pr | 0 | Cl | |
| 1-1694 | CH$_2$SO$_2$(CH$_2$)$_2$SO$_2$Me | CH$_2$-c-Pr | 0 | Cl | |
| 1-1695 | CH$_2$SO$_2$(CH$_2$)$_2$SO$_2$Me | (CH$_2$)$_2$OMe | 0 | Cl | |

TABLE A-continued

Compounds according to the invention of the general formula (I) in which $R^1$ is methyl, $R^4$ is hydrogen and q is zero

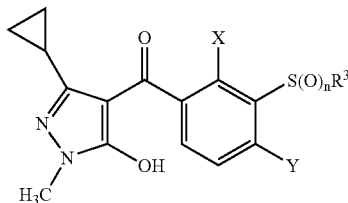

| No. | X | $R^3$ | n | Y | Physical data: $^1$H-NMR: δ[CDCl$_3$] |
|---|---|---|---|---|---|
| 1-1696 | CH$_2$SO$_2$(CH$_2$)$_2$SO$_2$Me | (CH$_2$)$_3$OMe | 0 | Cl | |
| 1-1697 | CH$_2$SO$_2$(CH$_2$)$_2$SO$_2$Me | (CH$_2$)$_2$OEt | 0 | Cl | |
| 1-1698 | CH$_2$SO$_2$(CH$_2$)$_2$SO$_2$Me | (CH$_2$)$_2$OCH$_2$-c-Pr | 0 | Cl | |
| 1-1699 | CH$_2$SO$_2$(CH$_2$)$_2$SO$_2$Me | c-Pr | 1 | Cl | |
| 1-1700 | CH$_2$SO$_2$(CH$_2$)$_2$SO$_2$Me | CH$_2$-c-Pr | 1 | Cl | |
| 1-1701 | CH$_2$SO$_2$(CH$_2$)$_2$SO$_2$Me | (CH$_2$)$_2$OMe | 1 | Cl | |
| 1-1702 | CH$_2$SO$_2$(CH$_2$)$_2$SO$_2$Me | (CH$_2$)$_3$OMe | 1 | Cl | |
| 1-1703 | CH$_2$SO$_2$(CH$_2$)$_2$SO$_2$Me | (CH$_2$)$_2$OEt | 1 | Cl | |
| 1-1704 | CH$_2$SO$_2$(CH$_2$)$_2$SO$_2$Me | (CH$_2$)$_2$OCH$_2$-c-Pr | 1 | Cl | |
| 1-1705 | CH$_2$SO$_2$(CH$_2$)$_2$SO$_2$Me | c-Pr | 2 | Cl | |
| 1-1706 | CH$_2$SO$_2$(CH$_2$)$_2$SO$_2$Me | CH$_2$-c-Pr | 2 | Cl | |
| 1-1707 | CH$_2$SO$_2$(CH$_2$)$_2$SO$_2$Me | (CH$_2$)$_2$OMe | 2 | Cl | |
| 1-1708 | CH$_2$SO$_2$(CH$_2$)$_2$SO$_2$Me | (CH$_2$)$_3$OMe | 2 | Cl | |
| 1-1709 | CH$_2$SO$_2$(CH$_2$)$_2$SO$_2$Me | (CH$_2$)$_2$OEt | 2 | Cl | |
| 1-1710 | CH$_2$SO$_2$(CH$_2$)$_2$SO$_2$Me | (CH$_2$)$_2$OCH$_2$-c-Pr | 2 | Cl | |
| 1-1711 | Cl | c-Pr | 0 | Br | |
| 1-1712 | Cl | CH$_2$-c-Pr | 0 | Br | |
| 1-1713 | Cl | (CH$_2$)$_2$OMe | 0 | Br | |
| 1-1714 | Cl | (CH$_2$)$_3$OMe | 0 | Br | |
| 1-1715 | Cl | (CH$_2$)$_2$OEt | 0 | Br | |
| 1-1716 | Cl | (CH$_2$)$_2$OCH$_2$-c-Pr | 0 | Br | |
| 1-1717 | Cl | c-Pr | 1 | Br | |
| 1-1718 | Cl | CH$_2$-c-Pr | 1 | Br | |
| 1-1719 | Cl | (CH$_2$)$_2$OMe | 1 | Br | |
| 1-1720 | Cl | (CH$_2$)$_3$OMe | 1 | Br | |
| 1-1721 | Cl | (CH$_2$)$_2$OEt | 1 | Br | |
| 1-1722 | Cl | (CH$_2$)$_2$OCH$_2$-c-Pr | 1 | Br | |
| 1-1723 | Cl | c-Pr | 2 | Br | |
| 1-1724 | Cl | CH$_2$-c-Pr | 2 | Br | |
| 1-1725 | Cl | (CH$_2$)$_2$OMe | 2 | Br | |
| 1-1726 | Cl | (CH$_2$)$_3$OMe | 2 | Br | |
| 1-1727 | Cl | (CH$_2$)$_2$OEt | 2 | Br | |
| 1-1728 | Cl | (CH$_2$)$_2$OCH$_2$-c-Pr | 2 | Br | |
| 1-1729 | Br | c-Pr | 0 | Br | |
| 1-1730 | Br | CH$_2$-c-Pr | 0 | Br | |
| 1-1731 | Br | (CH$_2$)$_2$OMe | 0 | Br | |
| 1-1732 | Br | (CH$_2$)$_3$OMe | 0 | Br | |
| 1-1733 | Br | (CH$_2$)$_2$OEt | 0 | Br | |
| 1-1734 | Br | (CH$_2$)$_2$OCH$_2$-c-Pr | 0 | Br | |
| 1-1735 | Br | c-Pr | 1 | Br | |
| 1-1736 | Br | CH$_2$-c-Pr | 1 | Br | |
| 1-1737 | Br | (CH$_2$)$_2$OMe | 1 | Br | |
| 1-1738 | Br | (CH$_2$)$_3$OMe | 1 | Br | |
| 1-1739 | Br | (CH$_2$)$_2$OEt | 1 | Br | |
| 1-1740 | Br | (CH$_2$)$_2$OCH$_2$-c-Pr | 1 | Br | |
| 1-1741 | Br | c-Pr | 2 | Br | |
| 1-1742 | Br | CH$_2$-c-Pr | 2 | Br | |
| 1-1743 | Br | (CH$_2$)$_2$OMe | 2 | Br | |
| 1-1744 | Br | (CH$_2$)$_3$OMe | 2 | Br | |
| 1-1745 | Br | (CH$_2$)$_2$OEt | 2 | Br | |
| 1-1746 | Br | (CH$_2$)$_2$OCH$_2$-c-Pr | 2 | Br | |
| 1-1747 | Me | c-Pr | 0 | Br | |
| 1-1748 | Me | CH$_2$-c-Pr | 0 | Br | |
| 1-1749 | Me | (CH$_2$)$_2$OMe | 0 | Br | |
| 1-1750 | Me | (CH$_2$)$_3$OMe | 0 | Br | |
| 1-1751 | Me | (CH$_2$)$_2$OEt | 0 | Br | |
| 1-1752 | Me | (CH$_2$)$_2$OCH$_2$-c-Pr | 0 | Br | |
| 1-1753 | Me | c-Pr | 1 | Br | |
| 1-1754 | Me | CH$_2$-c-Pr | 1 | Br | |
| 1-1755 | Me | (CH$_2$)$_2$OMe | 1 | Br | |
| 1-1756 | Me | (CH$_2$)$_3$OMe | 1 | Br | |
| 1-1757 | Me | (CH$_2$)$_2$OEt | 1 | Br | |
| 1-1758 | Me | (CH$_2$)$_2$OCH$_2$-c-Pr | 1 | Br | |

TABLE A-continued

Compounds according to the invention of the general formula (I) in which $R^1$ is methyl, $R^4$ is hydrogen and q is zero

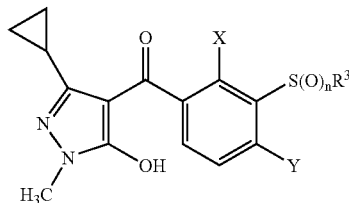

| No. | X | $R^3$ | n | Y | Physical data: $^1$H-NMR: δ[CDCl$_3$] |
|---|---|---|---|---|---|
| 1-1759 | Me | c-Pr | 2 | Br | |
| 1-1760 | Me | CH$_2$-c-Pr | 2 | Br | |
| 1-1761 | Me | (CH$_2$)$_2$OMe | 2 | Br | |
| 1-1762 | Me | (CH$_2$)$_3$OMe | 2 | Br | |
| 1-1763 | Me | (CH$_2$)$_2$OEt | 2 | Br | |
| 1-1764 | Me | (CH$_2$)$_2$OCH$_2$-c-Pr | 2 | Br | |
| 1-1765 | Et | c-Pr | 0 | Br | |
| 1-1766 | Et | CH$_2$-c-Pr | 0 | Br | |
| 1-1767 | Et | (CH$_2$)$_2$OMe | 0 | Br | |
| 1-1768 | Et | (CH$_2$)$_3$OMe | 0 | Br | |
| 1-1769 | Et | (CH$_2$)$_2$OEt | 0 | Br | |
| 1-1770 | Et | (CH$_2$)$_2$OCH$_2$-c-Pr | 0 | Br | |
| 1-1771 | Et | c-Pr | 1 | Br | |
| 1-1772 | Et | CH$_2$-c-Pr | 1 | Br | |
| 1-1773 | Et | (CH$_2$)$_2$OMe | 1 | Br | |
| 1-1774 | Et | (CH$_2$)$_3$OMe | 1 | Br | |
| 1-1775 | Et | (CH$_2$)$_2$OEt | 1 | Br | |
| 1-1776 | Et | (CH$_2$)$_2$OCH$_2$-c-Pr | 1 | Br | |
| 1-1777 | Et | c-Pr | 2 | Br | |
| 1-1778 | Et | CH$_2$-c-Pr | 2 | Br | |
| 1-1779 | Et | (CH$_2$)$_2$OMe | 2 | Br | |
| 1-1780 | Et | (CH$_2$)$_3$OMe | 2 | Br | |
| 1-1781 | Et | (CH$_2$)$_2$OEt | 2 | Br | |
| 1-1782 | Et | (CH$_2$)$_2$OCH$_2$-c-Pr | 2 | Br | |
| 1-1783 | CF$_3$ | c-Pr | 0 | Br | |
| 1-1784 | CF$_3$ | CH$_2$-c-Pr | 0 | Br | |
| 1-1785 | CF$_3$ | (CH$_2$)$_2$OMe | 0 | Br | |
| 1-1786 | CF$_3$ | (CH$_2$)$_3$OMe | 0 | Br | |
| 1-1787 | CF$_3$ | (CH$_2$)$_2$OEt | 0 | Br | |
| 1-1788 | CF$_3$ | (CH$_2$)$_2$OCH$_2$-c-Pr | 0 | Br | |
| 1-1789 | CF$_3$ | c-Pr | 1 | Br | |
| 1-1790 | CF$_3$ | CH$_2$-c-Pr | 1 | Br | |
| 1-1791 | CF$_3$ | (CH$_2$)$_2$OMe | 1 | Br | |
| 1-1792 | CF$_3$ | (CH$_2$)$_3$OMe | 1 | Br | |
| 1-1793 | CF$_3$ | (CH$_2$)$_2$OEt | 1 | Br | |
| 1-1794 | CF$_3$ | (CH$_2$)$_2$OCH$_2$-c-Pr | 1 | Br | |
| 1-1795 | CF$_3$ | c-Pr | 2 | Br | |
| 1-1796 | CF$_3$ | CH$_2$-c-Pr | 2 | Br | |
| 1-1797 | CF$_3$ | (CH$_2$)$_2$OMe | 2 | Br | |
| 1-1798 | CF$_3$ | (CH$_2$)$_3$OMe | 2 | Br | |
| 1-1799 | CF$_3$ | (CH$_2$)$_2$OEt | 2 | Br | |
| 1-1800 | CF$_3$ | (CH$_2$)$_2$OCH$_2$-c-Pr | 2 | Br | |
| 1-1801 | OMe | c-Pr | 0 | Br | |
| 1-1802 | OMe | CH$_2$-c-Pr | 0 | Br | |
| 1-1803 | OMe | (CH$_2$)$_2$OMe | 0 | Br | |
| 1-1804 | OMe | (CH$_2$)$_3$OMe | 0 | Br | |
| 1-1805 | OMe | (CH$_2$)$_2$OEt | 0 | Br | |
| 1-1806 | OMe | (CH$_2$)$_2$OCH$_2$-c-Pr | 0 | Br | |
| 1-1807 | OMe | c-Pr | 1 | Br | |
| 1-1808 | OMe | CH$_2$-c-Pr | 1 | Br | |
| 1-1809 | OMe | (CH$_2$)$_2$OMe | 1 | Br | |
| 1-1810 | OMe | (CH$_2$)$_3$OMe | 1 | Br | |
| 1-1811 | OMe | (CH$_2$)$_2$OEt | 1 | Br | |
| 1-1812 | OMe | (CH$_2$)$_2$OCH$_2$-c-Pr | 1 | Br | |
| 1-1813 | OMe | c-Pr | 2 | Br | |
| 1-1814 | OMe | CH$_2$-c-Pr | 2 | Br | |
| 1-1815 | OMe | (CH$_2$)$_2$OMe | 2 | Br | |
| 1-1816 | OMe | (CH$_2$)$_3$OMe | 2 | Br | |
| 1-1817 | OMe | (CH$_2$)$_2$OEt | 2 | Br | |
| 1-1818 | OMe | (CH$_2$)$_2$OCH$_2$-c-Pr | 2 | Br | |
| 1-1819 | OEt | c-Pr | 0 | Br | |
| 1-1820 | OEt | CH$_2$-c-Pr | 0 | Br | |
| 1-1821 | OEt | (CH$_2$)$_2$OMe | 0 | Br | |

TABLE A-continued

Compounds according to the invention of the general formula (I) in which $R^1$ is methyl, $R^4$ is hydrogen and q is zero

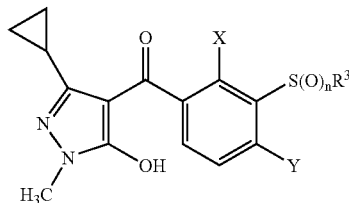

| No. | X | $R^3$ | n | Y | Physical data: $^1$H-NMR: δ[CDCl$_3$] |
|---|---|---|---|---|---|
| 1-1822 | OEt | (CH$_2$)$_3$OMe | 0 | Br | |
| 1-1823 | OEt | (CH$_2$)$_2$OEt | 0 | Br | |
| 1-1824 | OEt | (CH$_2$)$_2$OCH$_2$-c-Pr | 0 | Br | |
| 1-1825 | OEt | c-Pr | 1 | Br | |
| 1-1826 | OEt | CH$_2$-c-Pr | 1 | Br | |
| 1-1827 | OEt | (CH$_2$)$_2$OMe | 1 | Br | |
| 1-1828 | OEt | (CH$_2$)$_3$OMe | 1 | Br | |
| 1-1829 | OEt | (CH$_2$)$_2$OEt | 1 | Br | |
| 1-1830 | OEt | (CH$_2$)$_2$OCH$_2$-c-Pr | 1 | Br | |
| 1-1831 | OEt | c-Pr | 2 | Br | |
| 1-1832 | OEt | CH$_2$-c-Pr | 2 | Br | |
| 1-1833 | OEt | (CH$_2$)$_2$OMe | 2 | Br | |
| 1-1834 | OEt | (CH$_2$)$_3$OMe | 2 | Br | |
| 1-1835 | OEt | (CH$_2$)$_2$OEt | 2 | Br | |
| 1-1836 | OEt | (CH$_2$)$_2$OCH$_2$-c-Pr | 2 | Br | |
| 1-1837 | NO$_2$ | c-Pr | 0 | Br | |
| 1-1838 | NO$_2$ | CH$_2$-c-Pr | 0 | Br | |
| 1-1839 | NO$_2$ | (CH$_2$)$_2$OMe | 0 | Br | |
| 1-1840 | NO$_2$ | (CH$_2$)$_3$OMe | 0 | Br | |
| 1-1841 | NO$_2$ | (CH$_2$)$_2$OEt | 0 | Br | |
| 1-1842 | NO$_2$ | (CH$_2$)$_2$OCH$_2$-c-Pr | 0 | Br | |
| 1-1843 | NO$_2$ | c-Pr | 1 | Br | |
| 1-1844 | NO$_2$ | CH$_2$-c-Pr | 1 | Br | |
| 1-1845 | NO$_2$ | (CH$_2$)$_2$OMe | 1 | Br | |
| 1-1846 | NO$_2$ | (CH$_2$)$_3$OMe | 1 | Br | |
| 1-1847 | NO$_2$ | (CH$_2$)$_2$OEt | 1 | Br | |
| 1-1848 | NO$_2$ | (CH$_2$)$_2$OCH$_2$-c-Pr | 1 | Br | |
| 1-1849 | NO$_2$ | c-Pr | 2 | Br | |
| 1-1850 | NO$_2$ | CH$_2$-c-Pr | 2 | Br | |
| 1-1851 | NO$_2$ | (CH$_2$)$_2$OMe | 2 | Br | |
| 1-1852 | NO$_2$ | (CH$_2$)$_3$OMe | 2 | Br | |
| 1-1853 | NO$_2$ | (CH$_2$)$_2$OEt | 2 | Br | |
| 1-1854 | NO$_2$ | (CH$_2$)$_2$OCH$_2$-c-Pr | 2 | Br | |
| 1-1855 | SO$_2$Me | c-Pr | 0 | Br | |
| 1-1856 | SO$_2$Me | CH$_2$-c-Pr | 0 | Br | |
| 1-1857 | SO$_2$Me | (CH$_2$)$_2$OMe | 0 | Br | |
| 1-1858 | SO$_2$Me | (CH$_2$)$_3$OMe | 0 | Br | |
| 1-1859 | SO$_2$Me | (CH$_2$)$_2$OEt | 0 | Br | |
| 1-1860 | SO$_2$Me | (CH$_2$)$_2$OCH$_2$-c-Pr | 0 | Br | |
| 1-1861 | SO$_2$Me | c-Pr | 1 | Br | |
| 1-1862 | SO$_2$Me | CH$_2$-c-Pr | 1 | Br | |
| 1-1863 | SO$_2$Me | (CH$_2$)$_2$OMe | 1 | Br | |
| 1-1864 | SO$_2$Me | (CH$_2$)$_3$OMe | 1 | Br | |
| 1-1865 | SO$_2$Me | (CH$_2$)$_2$OEt | 1 | Br | |
| 1-1866 | SO$_2$Me | (CH$_2$)$_2$OCH$_2$-c-Pr | 1 | Br | |
| 1-1867 | SO$_2$Me | c-Pr | 2 | Br | |
| 1-1868 | SO$_2$Me | CH$_2$-c-Pr | 2 | Br | |
| 1-1869 | SO$_2$Me | (CH$_2$)$_2$OMe | 2 | Br | |
| 1-1870 | SO$_2$Me | (CH$_2$)$_3$OMe | 2 | Br | |
| 1-1871 | SO$_2$Me | (CH$_2$)$_2$OEt | 2 | Br | |
| 1-1872 | SO$_2$Me | (CH$_2$)$_2$OCH$_2$-c-Pr | 2 | Br | |
| 1-1873 | CH$_2$OMe | c-Pr | 0 | Br | |
| 1-1874 | CH$_2$OMe | CH$_2$-c-Pr | 0 | Br | |
| 1-1875 | CH$_2$OMe | (CH$_2$)$_2$OMe | 0 | Br | |
| 1-1876 | CH$_2$OMe | (CH$_2$)$_3$OMe | 0 | Br | |
| 1-1877 | CH$_2$OMe | (CH$_2$)$_2$OEt | 0 | Br | |
| 1-1878 | CH$_2$OMe | (CH$_2$)$_2$OCH$_2$-c-Pr | 0 | Br | |
| 1-1879 | CH$_2$OMe | c-Pr | 1 | Br | |
| 1-1880 | CH$_2$OMe | CH$_2$-c-Pr | 1 | Br | |
| 1-1881 | CH$_2$OMe | (CH$_2$)$_2$OMe | 1 | Br | |
| 1-1882 | CH$_2$OMe | (CH$_2$)$_3$OMe | 1 | Br | |
| 1-1883 | CH$_2$OMe | (CH$_2$)$_2$OEt | 1 | Br | |
| 1-1884 | CH$_2$OMe | (CH$_2$)$_2$OCH$_2$-c-Pr | 1 | Br | |

TABLE A-continued

Compounds according to the invention of the general formula (I) in which $R^1$ is methyl, $R^4$ is hydrogen and q is zero

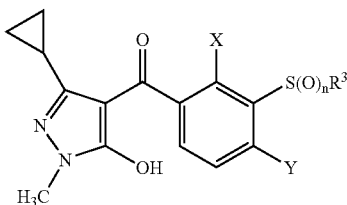

| No. | X | $R^3$ | n | Y | Physical data: $^1$H-NMR: δ[CDCl$_3$] |
|---|---|---|---|---|---|
| 1-1885 | CH$_2$OMe | c-Pr | 2 | Br | |
| 1-1886 | CH$_2$OMe | CH$_2$-c-Pr | 2 | Br | |
| 1-1887 | CH$_2$OMe | (CH$_2$)$_2$OMe | 2 | Br | |
| 1-1888 | CH$_2$OMe | (CH$_2$)$_3$OMe | 2 | Br | |
| 1-1889 | CH$_2$OMe | (CH$_2$)$_2$OEt | 2 | Br | |
| 1-1890 | CH$_2$OMe | (CH$_2$)$_2$OCH$_2$-c-Pr | 2 | Br | |
| 1-1891 | CH$_2$SO$_2$Me | c-Pr | 0 | Br | |
| 1-1892 | CH$_2$SO$_2$Me | CH$_2$-c-Pr | 0 | Br | |
| 1-1893 | CH$_2$SO$_2$Me | (CH$_2$)$_2$OMe | 0 | Br | |
| 1-1894 | CH$_2$SO$_2$Me | (CH$_2$)$_3$OMe | 0 | Br | |
| 1-1895 | CH$_2$SO$_2$Me | (CH$_2$)$_2$OEt | 0 | Br | |
| 1-1896 | CH$_2$SO$_2$Me | (CH$_2$)$_2$OCH$_2$-c-Pr | 0 | Br | |
| 1-1897 | CH$_2$SO$_2$Me | c-Pr | 1 | Br | |
| 1-1898 | CH$_2$SO$_2$Me | CH$_2$-c-Pr | 1 | Br | |
| 1-1899 | CH$_2$SO$_2$Me | (CH$_2$)$_2$OMe | 1 | Br | |
| 1-1900 | CH$_2$SO$_2$Me | (CH$_2$)$_3$OMe | 1 | Br | |
| 1-1901 | CH$_2$SO$_2$Me | (CH$_2$)$_2$OEt | 1 | Br | |
| 1-1902 | CH$_2$SO$_2$Me | (CH$_2$)$_2$OCH$_2$-c-Pr | 1 | Br | |
| 1-1903 | CH$_2$SO$_2$Me | c-Pr | 2 | Br | |
| 1-1904 | CH$_2$SO$_2$Me | CH$_2$-c-Pr | 2 | Br | |
| 1-1905 | CH$_2$SO$_2$Me | (CH$_2$)$_2$OMe | 2 | Br | |
| 1-1906 | CH$_2$SO$_2$Me | (CH$_2$)$_3$OMe | 2 | Br | |
| 1-1907 | CH$_2$SO$_2$Me | (CH$_2$)$_2$OEt | 2 | Br | |
| 1-1908 | CH$_2$SO$_2$Me | (CH$_2$)$_2$OCH$_2$-c-Pr | 2 | Br | |
| 1-1909 | CH$_2$O(CH$_2$)$_2$OMe | c-Pr | 0 | Br | |
| 1-1910 | CH$_2$O(CH$_2$)$_2$OMe | CH$_2$-c-Pr | 0 | Br | |
| 1-1911 | CH$_2$O(CH$_2$)$_2$OMe | (CH$_2$)$_2$OMe | 0 | Br | |
| 1-1912 | CH$_2$O(CH$_2$)$_2$OMe | (CH$_2$)$_3$OMe | 0 | Br | |
| 1-1913 | CH$_2$O(CH$_2$)$_2$OMe | (CH$_2$)$_2$OEt | 0 | Br | |
| 1-1914 | CH$_2$O(CH$_2$)$_2$OMe | (CH$_2$)$_2$OCH$_2$-c-Pr | 0 | Br | |
| 1-1915 | CH$_2$O(CH$_2$)$_2$OMe | c-Pr | 1 | Br | |
| 1-1916 | CH$_2$O(CH$_2$)$_2$OMe | CH$_2$-c-Pr | 1 | Br | |
| 1-1917 | CH$_2$O(CH$_2$)$_2$OMe | (CH$_2$)$_2$OMe | 1 | Br | |
| 1-1918 | CH$_2$O(CH$_2$)$_2$OMe | (CH$_2$)$_3$OMe | 1 | Br | |
| 1-1919 | CH$_2$O(CH$_2$)$_2$OMe | (CH$_2$)$_2$OEt | 1 | Br | |
| 1-1920 | CH$_2$O(CH$_2$)$_2$OMe | (CH$_2$)$_2$OCH$_2$-c-Pr | 1 | Br | |
| 1-1921 | CH$_2$O(CH$_2$)$_2$OMe | c-Pr | 2 | Br | |
| 1-1922 | CH$_2$O(CH$_2$)$_2$OMe | CH$_2$-c-Pr | 2 | Br | |
| 1-1923 | CH$_2$O(CH$_2$)$_2$OMe | (CH$_2$)$_2$OMe | 2 | Br | |
| 1-1924 | CH$_2$O(CH$_2$)$_2$OMe | (CH$_2$)$_3$OMe | 2 | Br | |
| 1-1925 | CH$_2$O(CH$_2$)$_2$OMe | (CH$_2$)$_2$OEt | 2 | Br | |
| 1-1926 | CH$_2$O(CH$_2$)$_2$OMe | (CH$_2$)$_2$OCH$_2$-c-Pr | 2 | Br | |
| 1-1927 | CH$_2$O(CH$_2$)$_2$OEt | c-Pr | 0 | Br | |
| 1-1928 | CH$_2$O(CH$_2$)$_2$OEt | CH$_2$-c-Pr | 0 | Br | |
| 1-1929 | CH$_2$O(CH$_2$)$_2$OEt | (CH$_2$)$_2$OMe | 0 | Br | |
| 1-1930 | CH$_2$O(CH$_2$)$_2$OEt | (CH$_2$)$_3$OMe | 0 | Br | |
| 1-1931 | CH$_2$O(CH$_2$)$_2$OEt | (CH$_2$)$_2$OEt | 0 | Br | |
| 1-1932 | CH$_2$O(CH$_2$)$_2$OEt | (CH$_2$)$_2$OCH$_2$-c-Pr | 0 | Br | |
| 1-1933 | CH$_2$O(CH$_2$)$_2$OEt | c-Pr | 1 | Br | |
| 1-1934 | CH$_2$O(CH$_2$)$_2$OEt | CH$_2$-c-Pr | 1 | Br | |
| 1-1935 | CH$_2$O(CH$_2$)$_2$OEt | (CH$_2$)$_2$OMe | 1 | Br | |
| 1-1936 | CH$_2$O(CH$_2$)$_2$OEt | (CH$_2$)$_3$OMe | 1 | Br | |
| 1-1937 | CH$_2$O(CH$_2$)$_2$OEt | (CH$_2$)$_2$OEt | 1 | Br | |
| 1-1938 | CH$_2$O(CH$_2$)$_2$OEt | (CH$_2$)$_2$OCH$_2$-c-Pr | 1 | Br | |
| 1-1939 | CH$_2$O(CH$_2$)$_2$OEt | c-Pr | 2 | Br | |
| 1-1940 | CH$_2$O(CH$_2$)$_2$OEt | CH$_2$-c-Pr | 2 | Br | |
| 1-1941 | CH$_2$O(CH$_2$)$_2$OEt | (CH$_2$)$_2$OMe | 2 | Br | |
| 1-1942 | CH$_2$O(CH$_2$)$_2$OEt | (CH$_2$)$_3$OMe | 2 | Br | |
| 1-1943 | CH$_2$O(CH$_2$)$_2$OEt | (CH$_2$)$_2$OEt | 2 | Br | |
| 1-1944 | CH$_2$O(CH$_2$)$_2$OEt | (CH$_2$)$_2$OCH$_2$-c-Pr | 2 | Br | |
| 1-1945 | CH$_2$O(CH$_2$)$_3$OMe | c-Pr | 0 | Br | |
| 1-1946 | CH$_2$O(CH$_2$)$_3$OMe | CH$_2$-c-Pr | 0 | Br | |
| 1-1947 | CH$_2$O(CH$_2$)$_3$OMe | (CH$_2$)$_2$OMe | 0 | Br | |

TABLE A-continued

Compounds according to the invention of the general formula (I) in which $R^1$ is methyl, $R^4$ is hydrogen and q is zero

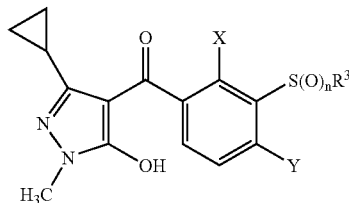

| No. | X | $R^3$ | n | Y | Physical data: $^1$H-NMR: δ[CDCl$_3$] |
|---|---|---|---|---|---|
| 1-1948 | CH$_2$O(CH$_2$)$_3$OMe | (CH$_2$)$_3$OMe | 0 | Br | |
| 1-1949 | CH$_2$O(CH$_2$)$_3$OMe | (CH$_2$)$_2$OEt | 0 | Br | |
| 1-1950 | CH$_2$O(CH$_2$)$_3$OMe | (CH$_2$)$_2$OCH$_2$-c-Pr | 0 | Br | |
| 1-1951 | CH$_2$O(CH$_2$)$_3$OMe | c-Pr | 1 | Br | |
| 1-1952 | CH$_2$O(CH$_2$)$_3$OMe | CH$_2$-c-Pr | 1 | Br | |
| 1-1953 | CH$_2$O(CH$_2$)$_3$OMe | (CH$_2$)$_2$OMe | 1 | Br | |
| 1-1954 | CH$_2$O(CH$_2$)$_3$OMe | (CH$_2$)$_3$OMe | 1 | Br | |
| 1-1955 | CH$_2$O(CH$_2$)$_3$OMe | (CH$_2$)$_2$OEt | 1 | Br | |
| 1-1956 | CH$_2$O(CH$_2$)$_3$OMe | (CH$_2$)$_2$OCH$_2$-c-Pr | 1 | Br | |
| 1-1957 | CH$_2$O(CH$_2$)$_3$OMe | c-Pr | 2 | Br | |
| 1-1958 | CH$_2$O(CH$_2$)$_3$OMe | CH$_2$-c-Pr | 2 | Br | |
| 1-1959 | CH$_2$O(CH$_2$)$_3$OMe | (CH$_2$)$_2$OMe | 2 | Br | |
| 1-1960 | CH$_2$O(CH$_2$)$_3$OMe | (CH$_2$)$_3$OMe | 2 | Br | |
| 1-1961 | CH$_2$O(CH$_2$)$_3$OMe | (CH$_2$)$_2$OEt | 2 | Br | |
| 1-1962 | CH$_2$O(CH$_2$)$_3$OMe | (CH$_2$)$_2$OCH$_2$-c-Pr | 2 | Br | |
| 1-1963 | CH$_2$OCH$_2$OMe | c-Pr | 0 | Br | |
| 1-1964 | CH$_2$OCH$_2$OMe | CH$_2$-c-Pr | 0 | Br | |
| 1-1965 | CH$_2$OCH$_2$OMe | (CH$_2$)$_2$OMe | 0 | Br | |
| 1-1966 | CH$_2$OCH$_2$OMe | (CH$_2$)$_3$OMe | 0 | Br | |
| 1-1967 | CH$_2$OCH$_2$OMe | (CH$_2$)$_2$OEt | 0 | Br | |
| 1-1968 | CH$_2$OCH$_2$OMe | (CH$_2$)$_2$OCH$_2$-c-Pr | 0 | Br | |
| 1-1969 | CH$_2$OCH$_2$OMe | c-Pr | 1 | Br | |
| 1-1970 | CH$_2$OCH$_2$OMe | CH$_2$-c-Pr | 1 | Br | |
| 1-1971 | CH$_2$OCH$_2$OMe | (CH$_2$)$_2$OMe | 1 | Br | |
| 1-1972 | CH$_2$OCH$_2$OMe | (CH$_2$)$_3$OMe | 1 | Br | |
| 1-1973 | CH$_2$OCH$_2$OMe | (CH$_2$)$_2$OEt | 1 | Br | |
| 1-1974 | CH$_2$OCH$_2$OMe | (CH$_2$)$_2$OCH$_2$-c-Pr | 1 | Br | |
| 1-1975 | CH$_2$OCH$_2$OMe | c-Pr | 2 | Br | |
| 1-1976 | CH$_2$OCH$_2$OMe | CH$_2$-c-Pr | 2 | Br | |
| 1-1977 | CH$_2$OCH$_2$OMe | (CH$_2$)$_2$OMe | 2 | Br | |
| 1-1978 | CH$_2$OCH$_2$OMe | (CH$_2$)$_3$OMe | 2 | Br | |
| 1-1979 | CH$_2$OCH$_2$OMe | (CH$_2$)$_2$OEt | 2 | Br | |
| 1-1980 | CH$_2$OCH$_2$OMe | (CH$_2$)$_2$OCH$_2$-c-Pr | 2 | Br | |
| 1-1981 | CH$_2$OCH$_2$OEt | c-Pr | 0 | Br | |
| 1-1982 | CH$_2$OCH$_2$OEt | CH$_2$-c-Pr | 0 | Br | |
| 1-1983 | CH$_2$OCH$_2$OEt | (CH$_2$)$_2$OMe | 0 | Br | |
| 1-1984 | CH$_2$OCH$_2$OEt | (CH$_2$)$_3$OMe | 0 | Br | |
| 1-1985 | CH$_2$OCH$_2$OEt | (CH$_2$)$_2$OEt | 0 | Br | |
| 1-1986 | CH$_2$OCH$_2$OEt | (CH$_2$)$_2$OCH$_2$-c-Pr | 0 | Br | |
| 1-1987 | CH$_2$OCH$_2$OEt | c-Pr | 1 | Br | |
| 1-1988 | CH$_2$OCH$_2$OEt | CH$_2$-c-Pr | 1 | Br | |
| 1-1989 | CH$_2$OCH$_2$OEt | (CH$_2$)$_2$OMe | 1 | Br | |
| 1-1990 | CH$_2$OCH$_2$OEt | (CH$_2$)$_3$OMe | 1 | Br | |
| 1-1991 | CH$_2$OCH$_2$OEt | (CH$_2$)$_2$OEt | 1 | Br | |
| 1-1992 | CH$_2$OCH$_2$OEt | (CH$_2$)$_2$OCH$_2$-c-Pr | 1 | Br | |
| 1-1993 | CH$_2$OCH$_2$OEt | c-Pr | 2 | Br | |
| 1-1994 | CH$_2$OCH$_2$OEt | CH$_2$-c-Pr | 2 | Br | |
| 1-1995 | CH$_2$OCH$_2$OEt | (CH$_2$)$_2$OMe | 2 | Br | |
| 1-1996 | CH$_2$OCH$_2$OEt | (CH$_2$)$_3$OMe | 2 | Br | |
| 1-1997 | CH$_2$OCH$_2$OEt | (CH$_2$)$_2$OEt | 2 | Br | |
| 1-1998 | CH$_2$OCH$_2$OEt | (CH$_2$)$_2$OCH$_2$-c-Pr | 2 | Br | |
| 1-1999 | CH$_2$O(CH$_2$)$_2$SO$_2$Me | c-Pr | 0 | Br | |
| 1-2000 | CH$_2$O(CH$_2$)$_2$SO$_2$Me | CH$_2$-c-Pr | 0 | Br | |
| 1-2001 | CH$_2$O(CH$_2$)$_2$SO$_2$Me | (CH$_2$)$_2$OMe | 0 | Br | |
| 1-2002 | CH$_2$O(CH$_2$)$_2$SO$_2$Me | (CH$_2$)$_3$OMe | 0 | Br | |
| 1-2003 | CH$_2$O(CH$_2$)$_2$SO$_2$Me | (CH$_2$)$_2$OEt | 0 | Br | |
| 1-2004 | CH$_2$O(CH$_2$)$_2$SO$_2$Me | (CH$_2$)$_2$OCH$_2$-c-Pr | 0 | Br | |
| 1-2005 | CH$_2$O(CH$_2$)$_2$SO$_2$Me | c-Pr | 1 | Br | |
| 1-2006 | CH$_2$O(CH$_2$)$_2$SO$_2$Me | CH$_2$-c-Pr | 1 | Br | |
| 1-2007 | CH$_2$O(CH$_2$)$_2$SO$_2$Me | (CH$_2$)$_2$OMe | 1 | Br | |
| 1-2008 | CH$_2$O(CH$_2$)$_2$SO$_2$Me | (CH$_2$)$_3$OMe | 1 | Br | |
| 1-2009 | CH$_2$O(CH$_2$)$_2$SO$_2$Me | (CH$_2$)$_2$OEt | 1 | Br | |
| 1-2010 | CH$_2$O(CH$_2$)$_2$SO$_2$Me | (CH$_2$)$_2$OCH$_2$-c-Pr | 1 | Br | |

TABLE A-continued

Compounds according to the invention of the general formula (I) in which $R^1$ is methyl, $R^4$ is hydrogen and q is zero

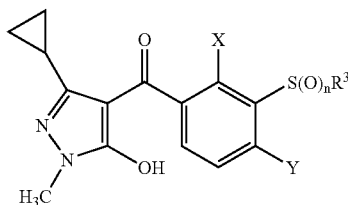

| No. | X | $R^3$ | n | Y | Physical data: $^1$H-NMR: δ[CDCl$_3$] |
|---|---|---|---|---|---|
| 1-2011 | CH$_2$O(CH$_2$)$_2$SO$_2$Me | c-Pr | 2 | Br | |
| 1-2012 | CH$_2$O(CH$_2$)$_2$SO$_2$Me | CH$_2$-c-Pr | 2 | Br | |
| 1-2013 | CH$_2$O(CH$_2$)$_2$SO$_2$Me | (CH$_2$)$_2$OMe | 2 | Br | |
| 1-2014 | CH$_2$O(CH$_2$)$_2$SO$_2$Me | (CH$_2$)$_3$OMe | 2 | Br | |
| 1-2015 | CH$_2$O(CH$_2$)$_2$SO$_2$Me | (CH$_2$)$_2$OEt | 2 | Br | |
| 1-2016 | CH$_2$O(CH$_2$)$_2$SO$_2$Me | (CH$_2$)$_2$OCH$_2$-c-Pr | 2 | Br | |
| 1-2017 | CH$_2$SO$_2$(CH$_2$)$_2$OMe | c-Pr | 0 | Br | |
| 1-2018 | CH$_2$SO$_2$(CH$_2$)$_2$OMe | CH$_2$-c-Pr | 0 | Br | |
| 1-2019 | CH$_2$SO$_2$(CH$_2$)$_2$OMe | (CH$_2$)$_2$OMe | 0 | Br | |
| 1-2020 | CH$_2$SO$_2$(CH$_2$)$_2$OMe | (CH$_2$)$_3$OMe | 0 | Br | |
| 1-2021 | CH$_2$SO$_2$(CH$_2$)$_2$OMe | (CH$_2$)$_2$OEt | 0 | Br | |
| 1-2022 | CH$_2$SO$_2$(CH$_2$)$_2$OMe | (CH$_2$)$_2$OCH$_2$-c-Pr | 0 | Br | |
| 1-2023 | CH$_2$SO$_2$(CH$_2$)$_2$OMe | c-Pr | 1 | Br | |
| 1-2024 | CH$_2$SO$_2$(CH$_2$)$_2$OMe | CH$_2$-c-Pr | 1 | Br | |
| 1-2025 | CH$_2$SO$_2$(CH$_2$)$_2$OMe | (CH$_2$)$_2$OMe | 1 | Br | |
| 1-2026 | CH$_2$SO$_2$(CH$_2$)$_2$OMe | (CH$_2$)$_3$OMe | 1 | Br | |
| 1-2027 | CH$_2$SO$_2$(CH$_2$)$_2$OMe | (CH$_2$)$_2$OEt | 1 | Br | |
| 1-2028 | CH$_2$SO$_2$(CH$_2$)$_2$OMe | (CH$_2$)$_2$OCH$_2$-c-Pr | 1 | Br | |
| 1-2029 | CH$_2$SO$_2$(CH$_2$)$_2$OMe | c-Pr | 2 | Br | |
| 1-2030 | CH$_2$SO$_2$(CH$_2$)$_2$OMe | CH$_2$-c-Pr | 2 | Br | |
| 1-2031 | CH$_2$SO$_2$(CH$_2$)$_2$OMe | (CH$_2$)$_2$OMe | 2 | Br | |
| 1-2032 | CH$_2$SO$_2$(CH$_2$)$_2$OMe | (CH$_2$)$_3$OMe | 2 | Br | |
| 1-2033 | CH$_2$SO$_2$(CH$_2$)$_2$OMe | (CH$_2$)$_2$OEt | 2 | Br | |
| 1-2034 | CH$_2$SO$_2$(CH$_2$)$_2$OMe | (CH$_2$)$_2$OCH$_2$-c-Pr | 2 | Br | |
| 1-2035 | CH$_2$SO$_2$(CH$_2$)$_2$SO$_2$Me | c-Pr | 0 | Br | |
| 1-2036 | CH$_2$SO$_2$(CH$_2$)$_2$SO$_2$Me | CH$_2$-c-Pr | 0 | Br | |
| 1-2037 | CH$_2$SO$_2$(CH$_2$)$_2$SO$_2$Me | (CH$_2$)$_2$OMe | 0 | Br | |
| 1-2038 | CH$_2$SO$_2$(CH$_2$)$_2$SO$_2$Me | (CH$_2$)$_3$OMe | 0 | Br | |
| 1-2039 | CH$_2$SO$_2$(CH$_2$)$_2$SO$_2$Me | (CH$_2$)$_2$OEt | 0 | Br | |
| 1-2040 | CH$_2$SO$_2$(CH$_2$)$_2$SO$_2$Me | (CH$_2$)$_2$OCH$_2$-c-Pr | 0 | Br | |
| 1-2041 | CH$_2$SO$_2$(CH$_2$)$_2$SO$_2$Me | c-Pr | 1 | Br | |
| 1-2042 | CH$_2$SO$_2$(CH$_2$)$_2$SO$_2$Me | CH$_2$-c-Pr | 1 | Br | |
| 1-2043 | CH$_2$SO$_2$(CH$_2$)$_2$SO$_2$Me | (CH$_2$)$_2$OMe | 1 | Br | |
| 1-2044 | CH$_2$SO$_2$(CH$_2$)$_2$SO$_2$Me | (CH$_2$)$_3$OMe | 1 | Br | |
| 1-2045 | CH$_2$SO$_2$(CH$_2$)$_2$SO$_2$Me | (CH$_2$)$_2$OEt | 1 | Br | |
| 1-2046 | CH$_2$SO$_2$(CH$_2$)$_2$SO$_2$Me | (CH$_2$)$_2$OCH$_2$-c-Pr | 1 | Br | |
| 1-2047 | CH$_2$SO$_2$(CH$_2$)$_2$SO$_2$Me | c-Pr | 2 | Br | |
| 1-2048 | CH$_2$SO$_2$(CH$_2$)$_2$SO$_2$Me | CH$_2$-c-Pr | 2 | Br | |
| 1-2049 | CH$_2$SO$_2$(CH$_2$)$_2$SO$_2$Me | (CH$_2$)$_2$OMe | 2 | Br | |
| 1-2050 | CH$_2$SO$_2$(CH$_2$)$_2$SO$_2$Me | (CH$_2$)$_3$OMe | 2 | Br | |
| 1-2051 | CH$_2$SO$_2$(CH$_2$)$_2$SO$_2$Me | (CH$_2$)$_2$OEt | 2 | Br | |
| 1-2052 | CH$_2$SO$_2$(CH$_2$)$_2$SO$_2$Me | (CH$_2$)$_2$OCH$_2$-c-Pr | 2 | Br | |
| 1-2053 | Cl | c-Pr | 0 | CF$_3$ | |
| 1-2054 | Cl | CH$_2$-c-Pr | 0 | CF$_3$ | |
| 1-2055 | Cl | (CH$_2$)$_2$OMe | 0 | CF$_3$ | |
| 1-2056 | Cl | (CH$_2$)$_3$OMe | 0 | CF$_3$ | |
| 1-2057 | Cl | (CH$_2$)$_2$OEt | 0 | CF$_3$ | |
| 1-2058 | Cl | (CH$_2$)$_2$OCH$_2$-c-Pr | 0 | CF$_3$ | |
| 1-2059 | Cl | c-Pr | 1 | CF$_3$ | |
| 1-2060 | Cl | CH$_2$-c-Pr | 1 | CF$_3$ | |
| 1-2061 | Cl | (CH$_2$)$_2$OMe | 1 | CF$_3$ | |
| 1-2062 | Cl | (CH$_2$)$_3$OMe | 1 | CF$_3$ | |
| 1-2063 | Cl | (CH$_2$)$_2$OEt | 1 | CF$_3$ | |
| 1-2064 | Cl | (CH$_2$)$_2$OCH$_2$-c-Pr | 1 | CF$_3$ | |
| 1-2065 | Cl | c-Pr | 2 | CF$_3$ | |
| 1-2066 | Cl | CH$_2$-c-Pr | 2 | CF$_3$ | |
| 1-2067 | Cl | (CH$_2$)$_2$OMe | 2 | CF$_3$ | |
| 1-2068 | Cl | (CH$_2$)$_3$OMe | 2 | CF$_3$ | |
| 1-2069 | Cl | (CH$_2$)$_2$OEt | 2 | CF$_3$ | |
| 1-2070 | Cl | (CH$_2$)$_2$OCH$_2$-c-Pr | 2 | CF$_3$ | |
| 1-2071 | Br | c-Pr | 0 | CF$_3$ | |
| 1-2072 | Br | CH$_2$-c-Pr | 0 | CF$_3$ | |
| 1-2073 | Br | (CH$_2$)$_2$OMe | 0 | CF$_3$ | |

TABLE A-continued

Compounds according to the invention of the general formula (I) in which $R^1$ is methyl, $R^4$ is hydrogen and q is zero

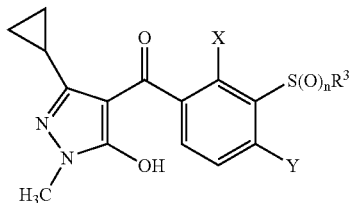

| No. | X | $R^3$ | n | Y | Physical data: $^1$H-NMR: δ[CDCl$_3$] |
|---|---|---|---|---|---|
| 1-2074 | Br | (CH$_2$)$_3$OMe | 0 | CF$_3$ | |
| 1-2075 | Br | (CH$_2$)$_2$OEt | 0 | CF$_3$ | |
| 1-2076 | Br | (CH$_2$)$_2$OCH$_2$-c-Pr | 0 | CF$_3$ | |
| 1-2077 | Br | c-Pr | 1 | CF$_3$ | |
| 1-2078 | Br | CH$_2$-c-Pr | 1 | CF$_3$ | |
| 1-2079 | Br | (CH$_2$)$_2$OMe | 1 | CF$_3$ | |
| 1-2080 | Br | (CH$_2$)$_3$OMe | 1 | CF$_3$ | |
| 1-2081 | Br | (CH$_2$)$_2$OEt | 1 | CF$_3$ | |
| 1-2082 | Br | (CH$_2$)$_2$OCH$_2$-c-Pr | 1 | CF$_3$ | |
| 1-2083 | Br | c-Pr | 2 | CF$_3$ | |
| 1-2084 | Br | CH$_2$-c-Pr | 2 | CF$_3$ | |
| 1-2085 | Br | (CH$_2$)$_2$OMe | 2 | CF$_3$ | |
| 1-2086 | Br | (CH$_2$)$_3$OMe | 2 | CF$_3$ | |
| 1-2087 | Br | (CH$_2$)$_2$OEt | 2 | CF$_3$ | |
| 1-2088 | Br | (CH$_2$)$_2$OCH$_2$-c-Pr | 2 | CF$_3$ | |
| 1-2089 | Me | c-Pr | 0 | CF$_3$ | |
| 1-2090 | Me | CH$_2$-c-Pr | 0 | CF$_3$ | |
| 1-2091 | Me | (CH$_2$)$_2$OMe | 0 | CF$_3$ | 7.68 (d, 1H), 7.39 (d, 1H), 3.61 (s, 3H), 3.52 (t, 2H), 3.32 (s, 3H), 2.91 (t, 2H), 2.64 (s, 3H), 0.90-0.83 (m, 1H), 0.76 (m, 2H), 0.47 (m, 2H) |
| 1-2092 | Me | (CH$_2$)$_3$OMe | 0 | CF$_3$ | |
| 1-2093 | Me | (CH$_2$)$_2$OEt | 0 | CF$_3$ | |
| 1-2094 | Me | (CH$_2$)$_2$OCH$_2$-c-Pr | 0 | CF$_3$ | |
| 1-2095 | Me | c-Pr | 1 | CF$_3$ | |
| 1-2096 | Me | CH$_2$-c-Pr | 1 | CF$_3$ | |
| 1-2097 | Me | (CH$_2$)$_2$OMe | 1 | CF$_3$ | 7.72 (d, 1H), 7.51 (d, 1H), 3.95 (dt, 1H), 3.83 (dt, 1H), 3.62-3.58 (m, 1H), 3.61 (s, 3H), 3.41 (s, 3H), 3.13 (m, 1H), 2.82 (s, 3H), 0.91-0.72 (m, 3H), 0.58 (m, 1H), 0.46 (m, 1H) |
| 1-2098 | Me | (CH$_2$)$_3$OMe | 1 | CF$_3$ | |
| 1-2099 | Me | (CH$_2$)$_2$OEt | 1 | CF$_3$ | |
| 1-2100 | Me | (CH$_2$)$_2$OCH$_2$-c-Pr | 1 | CF$_3$ | |
| 1-2101 | Me | c-Pr | 2 | CF$_3$ | |
| 1-2102 | Me | CH$_2$-c-Pr | 2 | CF$_3$ | |
| 1-2103 | Me | (CH$_2$)$_2$OMe | 2 | CF$_3$ | |
| 1-2104 | Me | (CH$_2$)$_3$OMe | 2 | CF$_3$ | |
| 1-2105 | Me | (CH$_2$)$_2$OEt | 2 | CF$_3$ | |
| 1-2106 | Me | (CH$_2$)$_2$OCH$_2$-c-Pr | 2 | CF$_3$ | |
| 1-2107 | Et | c-Pr | 0 | CF$_3$ | |
| 1-2108 | Et | CH$_2$-c-Pr | 0 | CF$_3$ | |
| 1-2109 | Et | (CH$_2$)$_2$OMe | 0 | CF$_3$ | |
| 1-2110 | Et | (CH$_2$)$_3$OMe | 0 | CF$_3$ | |
| 1-2111 | Et | (CH$_2$)$_2$OEt | 0 | CF$_3$ | |
| 1-2112 | Et | (CH$_2$)$_2$OCH$_2$-c-Pr | 0 | CF$_3$ | |
| 1-2113 | Et | c-Pr | 1 | CF$_3$ | |
| 1-2114 | Et | CH$_2$-c-Pr | 1 | CF$_3$ | |
| 1-2115 | Et | (CH$_2$)$_2$OMe | 1 | CF$_3$ | |
| 1-2116 | Et | (CH$_2$)$_3$OMe | 1 | CF$_3$ | |
| 1-2117 | Et | (CH$_2$)$_2$OEt | 1 | CF$_3$ | |
| 1-2118 | Et | (CH$_2$)$_2$OCH$_2$-c-Pr | 1 | CF$_3$ | |
| 1-2119 | Et | c-Pr | 2 | CF$_3$ | |
| 1-2120 | Et | CH$_2$-c-Pr | 2 | CF$_3$ | |
| 1-2121 | Et | (CH$_2$)$_2$OMe | 2 | CF$_3$ | |
| 1-2122 | Et | (CH$_2$)$_3$OMe | 2 | CF$_3$ | |
| 1-2123 | Et | (CH$_2$)$_2$OEt | 2 | CF$_3$ | |
| 1-2124 | Et | (CH$_2$)$_2$OCH$_2$-c-Pr | 2 | CF$_3$ | |
| 1-2125 | CF$_3$ | c-Pr | 0 | CF$_3$ | |

TABLE A-continued

Compounds according to the invention of the general formula (I) in which $R^1$ is methyl, $R^4$ is hydrogen and q is zero

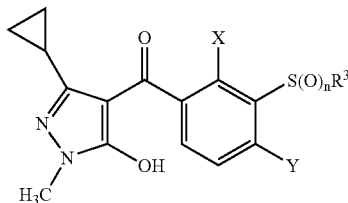

| No. | X | $R^3$ | n | Y | Physical data: $^1$H-NMR: δ[CDCl$_3$] |
|---|---|---|---|---|---|
| 1-2126 | CF$_3$ | CH$_2$-c-Pr | 0 | CF$_3$ | |
| 1-2127 | CF$_3$ | (CH$_2$)$_2$OMe | 0 | CF$_3$ | |
| 1-2128 | CF$_3$ | (CH$_2$)$_3$OMe | 0 | CF$_3$ | |
| 1-2129 | CF$_3$ | (CH$_2$)$_2$OEt | 0 | CF$_3$ | |
| 1-2130 | CF$_3$ | (CH$_2$)$_2$OCH$_2$-c-Pr | 0 | CF$_3$ | |
| 1-2131 | CF$_3$ | c-Pr | 1 | CF$_3$ | |
| 1-2132 | CF$_3$ | CH$_2$-c-Pr | 1 | CF$_3$ | |
| 1-2133 | CF$_3$ | (CH$_2$)$_2$OMe | 1 | CF$_3$ | |
| 1-2134 | CF$_3$ | (CH$_2$)$_3$OMe | 1 | CF$_3$ | |
| 1-2135 | CF$_3$ | (CH$_2$)$_2$OEt | 1 | CF$_3$ | |
| 1-2136 | CF$_3$ | (CH$_2$)$_2$OCH$_2$-c-Pr | 1 | CF$_3$ | |
| 1-2137 | CF$_3$ | c-Pr | 2 | CF$_3$ | |
| 1-2138 | CF$_3$ | CH$_2$-c-Pr | 2 | CF$_3$ | |
| 1-2139 | CF$_3$ | (CH$_2$)$_2$OMe | 2 | CF$_3$ | |
| 1-2140 | CF$_3$ | (CH$_2$)$_3$OMe | 2 | CF$_3$ | |
| 1-2141 | CF$_3$ | (CH$_2$)$_2$OEt | 2 | CF$_3$ | |
| 1-2142 | CF$_3$ | (CH$_2$)$_2$OCH$_2$-c-Pr | 2 | CF$_3$ | |
| 1-2143 | OMe | c-Pr | 0 | CF$_3$ | |
| 1-2144 | OMe | CH$_2$-c-Pr | 0 | CF$_3$ | |
| 1-2145 | OMe | (CH$_2$)$_2$OMe | 0 | CF$_3$ | |
| 1-2146 | OMe | (CH$_2$)$_3$OMe | 0 | CF$_3$ | |
| 1-2147 | OMe | (CH$_2$)$_2$OEt | 0 | CF$_3$ | |
| 1-2148 | OMe | (CH$_2$)$_2$OCH$_2$-c-Pr | 0 | CF$_3$ | |
| 1-2149 | OMe | c-Pr | 1 | CF$_3$ | |
| 1-2150 | OMe | CH$_2$-c-Pr | 1 | CF$_3$ | |
| 1-2151 | OMe | (CH$_2$)$_2$OMe | 1 | CF$_3$ | |
| 1-2152 | OMe | (CH$_2$)$_3$OMe | 1 | CF$_3$ | |
| 1-2153 | OMe | (CH$_2$)$_2$OEt | 1 | CF$_3$ | |
| 1-2154 | OMe | (CH$_2$)$_2$OCH$_2$-c-Pr | 1 | CF$_3$ | |
| 1-2155 | OMe | c-Pr | 2 | CF$_3$ | |
| 1-2156 | OMe | CH$_2$-c-Pr | 2 | CF$_3$ | |
| 1-2157 | OMe | (CH$_2$)$_2$OMe | 2 | CF$_3$ | |
| 1-2158 | OMe | (CH$_2$)$_3$OMe | 2 | CF$_3$ | |
| 1-2159 | OMe | (CH$_2$)$_2$OEt | 2 | CF$_3$ | |
| 1-2160 | OMe | (CH$_2$)$_2$OCH$_2$-c-Pr | 2 | CF$_3$ | |
| 1-2161 | OEt | c-Pr | 0 | CF$_3$ | |
| 1-2162 | OEt | CH$_2$-c-Pr | 0 | CF$_3$ | |
| 1-2163 | OEt | (CH$_2$)$_2$OMe | 0 | CF$_3$ | |
| 1-2164 | OEt | (CH$_2$)$_3$OMe | 0 | CF$_3$ | |
| 1-2165 | OEt | (CH$_2$)$_2$OEt | 0 | CF$_3$ | |
| 1-2166 | OEt | (CH$_2$)$_2$OCH$_2$-c-Pr | 0 | CF$_3$ | |
| 1-2167 | OEt | c-Pr | 1 | CF$_3$ | |
| 1-2168 | OEt | CH$_2$-c-Pr | 1 | CF$_3$ | |
| 1-2169 | OEt | (CH$_2$)$_2$OMe | 1 | CF$_3$ | |
| 1-2170 | OEt | (CH$_2$)$_3$OMe | 1 | CF$_3$ | |
| 1-2171 | OEt | (CH$_2$)$_2$OEt | 1 | CF$_3$ | |
| 1-2172 | OEt | (CH$_2$)$_2$OCH$_2$-c-Pr | 1 | CF$_3$ | |
| 1-2173 | OEt | c-Pr | 2 | CF$_3$ | |
| 1-2174 | OEt | CH$_2$-c-Pr | 2 | CF$_3$ | |
| 1-2175 | OEt | (CH$_2$)$_2$OMe | 2 | CF$_3$ | |
| 1-2176 | OEt | (CH$_2$)$_3$OMe | 2 | CF$_3$ | |
| 1-2177 | OEt | (CH$_2$)$_2$OEt | 2 | CF$_3$ | |
| 1-2178 | OEt | (CH$_2$)$_2$OCH$_2$-c-Pr | 2 | CF$_3$ | |
| 1-2179 | NO$_2$ | c-Pr | 0 | CF$_3$ | |
| 1-2180 | NO$_2$ | CH$_2$-c-Pr | 0 | CF$_3$ | |
| 1-2181 | NO$_2$ | (CH$_2$)$_2$OMe | 0 | CF$_3$ | |
| 1-2182 | NO$_2$ | (CH$_2$)$_3$OMe | 0 | CF$_3$ | |
| 1-2183 | NO$_2$ | (CH$_2$)$_2$OEt | 0 | CF$_3$ | |
| 1-2184 | NO$_2$ | (CH$_2$)$_2$OCH$_2$-c-Pr | 0 | CF$_3$ | |
| 1-2185 | NO$_2$ | c-Pr | 1 | CF$_3$ | |
| 1-2186 | NO$_2$ | CH$_2$-c-Pr | 1 | CF$_3$ | |
| 1-2187 | NO$_2$ | (CH$_2$)$_2$OMe | 1 | CF$_3$ | |
| 1-2188 | NO$_2$ | (CH$_2$)$_3$OMe | 1 | CF$_3$ | |

TABLE A-continued

Compounds according to the invention of the general formula (I) in which $R^1$ is methyl, $R^4$ is hydrogen and q is zero

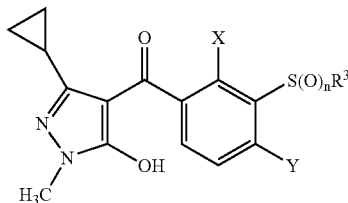

| No. | X | $R^3$ | n | Y | Physical data: $^1$H-NMR: δ[CDCl$_3$] |
|---|---|---|---|---|---|
| 1-2189 | NO$_2$ | (CH$_2$)$_2$OEt | 1 | CF$_3$ | |
| 1-2190 | NO$_2$ | (CH$_2$)$_2$OCH$_2$-c-Pr | 1 | CF$_3$ | |
| 1-2191 | NO$_2$ | c-Pr | 2 | CF$_3$ | |
| 1-2192 | NO$_2$ | CH$_2$-c-Pr | 2 | CF$_3$ | |
| 1-2193 | NO$_2$ | (CH$_2$)$_2$OMe | 2 | CF$_3$ | |
| 1-2194 | NO$_2$ | (CH$_2$)$_3$OMe | 2 | CF$_3$ | |
| 1-2195 | NO$_2$ | (CH$_2$)$_2$OEt | 2 | CF$_3$ | |
| 1-2196 | NO$_2$ | (CH$_2$)$_2$OCH$_2$-c-Pr | 2 | CF$_3$ | |
| 1-2197 | SO$_2$Me | c-Pr | 0 | CF$_3$ | |
| 1-2198 | SO$_2$Me | CH$_2$-c-Pr | 0 | CF$_3$ | |
| 1-2199 | SO$_2$Me | (CH$_2$)$_2$OMe | 0 | CF$_3$ | |
| 1-2200 | SO$_2$Me | (CH$_2$)$_3$OMe | 0 | CF$_3$ | |
| 1-2201 | SO$_2$Me | (CH$_2$)$_2$OEt | 0 | CF$_3$ | |
| 1-2202 | SO$_2$Me | (CH$_2$)$_2$OCH$_2$-c-Pr | 0 | CF$_3$ | |
| 1-2203 | SO$_2$Me | c-Pr | 1 | CF$_3$ | |
| 1-2204 | SO$_2$Me | CH$_2$-c-Pr | 1 | CF$_3$ | |
| 1-2205 | SO$_2$Me | (CH$_2$)$_2$OMe | 1 | CF$_3$ | |
| 1-2206 | SO$_2$Me | (CH$_2$)$_3$OMe | 1 | CF$_3$ | |
| 1-2207 | SO$_2$Me | (CH$_2$)$_2$OEt | 1 | CF$_3$ | |
| 1-2208 | SO$_2$Me | (CH$_2$)$_2$OCH$_2$-c-Pr | 1 | CF$_3$ | |
| 1-2209 | SO$_2$Me | c-Pr | 2 | CF$_3$ | |
| 1-2210 | SO$_2$Me | CH$_2$-c-Pr | 2 | CF$_3$ | |
| 1-2211 | SO$_2$Me | (CH$_2$)$_2$OMe | 2 | CF$_3$ | |
| 1-2212 | SO$_2$Me | (CH$_2$)$_3$OMe | 2 | CF$_3$ | |
| 1-2213 | SO$_2$Me | (CH$_2$)$_2$OEt | 2 | CF$_3$ | |
| 1-2214 | SO$_2$Me | (CH$_2$)$_2$OCH$_2$-c-Pr | 2 | CF$_3$ | |
| 1-2215 | CH$_2$OMe | c-Pr | 0 | CF$_3$ | |
| 1-2216 | CH$_2$OMe | CH$_2$-c-Pr | 0 | CF$_3$ | |
| 1-2217 | CH$_2$OMe | (CH$_2$)$_2$OMe | 0 | CF$_3$ | |
| 1-2218 | CH$_2$OMe | (CH$_2$)$_3$OMe | 0 | CF$_3$ | |
| 1-2219 | CH$_2$OMe | (CH$_2$)$_2$OEt | 0 | CF$_3$ | |
| 1-2220 | CH$_2$OMe | (CH$_2$)$_2$OCH$_2$-c-Pr | 0 | CF$_3$ | |
| 1-2221 | CH$_2$OMe | c-Pr | 1 | CF$_3$ | |
| 1-2222 | CH$_2$OMe | CH$_2$-c-Pr | 1 | CF$_3$ | |
| 1-2223 | CH$_2$OMe | (CH$_2$)$_2$OMe | 1 | CF$_3$ | |
| 1-2224 | CH$_2$OMe | (CH$_2$)$_3$OMe | 1 | CF$_3$ | |
| 1-2225 | CH$_2$OMe | (CH$_2$)$_2$OEt | 1 | CF$_3$ | |
| 1-2226 | CH$_2$OMe | (CH$_2$)$_2$OCH$_2$-c-Pr | 1 | CF$_3$ | |
| 1-2227 | CH$_2$OMe | c-Pr | 2 | CF$_3$ | |
| 1-2228 | CH$_2$OMe | CH$_2$-c-Pr | 2 | CF$_3$ | |
| 1-2229 | CH$_2$OMe | (CH$_2$)$_2$OMe | 2 | CF$_3$ | |
| 1-2230 | CH$_2$OMe | (CH$_2$)$_3$OMe | 2 | CF$_3$ | |
| 1-2231 | CH$_2$OMe | (CH$_2$)$_2$OEt | 2 | CF$_3$ | |
| 1-2232 | CH$_2$OMe | (CH$_2$)$_2$OCH$_2$-c-Pr | 2 | CF$_3$ | |
| 1-2233 | CH$_2$SO$_2$Me | c-Pr | 0 | CF$_3$ | |
| 1-2234 | CH$_2$SO$_2$Me | CH$_2$-c-Pr | 0 | CF$_3$ | |
| 1-2235 | CH$_2$SO$_2$Me | (CH$_2$)$_2$OMe | 0 | CF$_3$ | |
| 1-2236 | CH$_2$SO$_2$Me | (CH$_2$)$_3$OMe | 0 | CF$_3$ | |
| 1-2237 | CH$_2$SO$_2$Me | (CH$_2$)$_2$OEt | 0 | CF$_3$ | |
| 1-2238 | CH$_2$SO$_2$Me | (CH$_2$)$_2$OCH$_2$-c-Pr | 0 | CF$_3$ | |
| 1-2239 | CH$_2$SO$_2$Me | c-Pr | 1 | CF$_3$ | |
| 1-2240 | CH$_2$SO$_2$Me | CH$_2$-c-Pr | 1 | CF$_3$ | |
| 1-2241 | CH$_2$SO$_2$Me | (CH$_2$)$_2$OMe | 1 | CF$_3$ | |
| 1-2242 | CH$_2$SO$_2$Me | (CH$_2$)$_3$OMe | 1 | CF$_3$ | |
| 1-2243 | CH$_2$SO$_2$Me | (CH$_2$)$_2$OEt | 1 | CF$_3$ | |
| 1-2244 | CH$_2$SO$_2$Me | (CH$_2$)$_2$OCH$_2$-c-Pr | 1 | CF$_3$ | |
| 1-2245 | CH$_2$SO$_2$Me | c-Pr | 2 | CF$_3$ | |
| 1-2246 | CH$_2$SO$_2$Me | CH$_2$-c-Pr | 2 | CF$_3$ | |
| 1-2247 | CH$_2$SO$_2$Me | (CH$_2$)$_2$OMe | 2 | CF$_3$ | |
| 1-2248 | CH$_2$SO$_2$Me | (CH$_2$)$_3$OMe | 2 | CF$_3$ | |
| 1-2249 | CH$_2$SO$_2$Me | (CH$_2$)$_2$OEt | 2 | CF$_3$ | |
| 1-2250 | CH$_2$SO$_2$Me | (CH$_2$)$_2$OCH$_2$-c-Pr | 2 | CF$_3$ | |
| 1-2251 | CH$_2$O(CH$_2$)$_2$OMe | c-Pr | 0 | CF$_3$ | |

TABLE A-continued

Compounds according to the invention of the general formula (I) in which $R^1$ is methyl, $R^4$ is hydrogen and q is zero

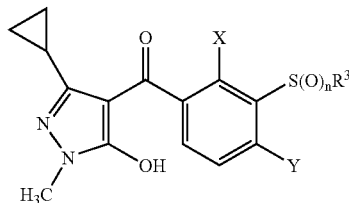

| No. | X | $R^3$ | n | Y | Physical data: $^1$H-NMR: δ[CDCl$_3$] |
|---|---|---|---|---|---|
| 1-2252 | CH$_2$O(CH$_2$)$_2$OMe | CH$_2$-c-Pr | 0 | CF$_3$ | |
| 1-2253 | CH$_2$O(CH$_2$)$_2$OMe | (CH$_2$)$_2$OMe | 0 | CF$_3$ | |
| 1-2254 | CH$_2$O(CH$_2$)$_2$OMe | (CH$_2$)$_3$OMe | 0 | CF$_3$ | |
| 1-2255 | CH$_2$O(CH$_2$)$_2$OMe | (CH$_2$)$_2$OEt | 0 | CF$_3$ | |
| 1-2256 | CH$_2$O(CH$_2$)$_2$OMe | (CH$_2$)$_2$OCH$_2$-c-Pr | 0 | CF$_3$ | |
| 1-2257 | CH$_2$O(CH$_2$)$_2$OMe | c-Pr | 1 | CF$_3$ | |
| 1-2258 | CH$_2$O(CH$_2$)$_2$OMe | CH$_2$-c-Pr | 1 | CF$_3$ | |
| 1-2259 | CH$_2$O(CH$_2$)$_2$OMe | (CH$_2$)$_2$OMe | 1 | CF$_3$ | |
| 1-2260 | CH$_2$O(CH$_2$)$_2$OMe | (CH$_2$)$_3$OMe | 1 | CF$_3$ | |
| 1-2261 | CH$_2$O(CH$_2$)$_2$OMe | (CH$_2$)$_2$OEt | 1 | CF$_3$ | |
| 1-2262 | CH$_2$O(CH$_2$)$_2$OMe | (CH$_2$)$_2$OCH$_2$-c-Pr | 1 | CF$_3$ | |
| 1-2263 | CH$_2$O(CH$_2$)$_2$OMe | c-Pr | 2 | CF$_3$ | |
| 1-2264 | CH$_2$O(CH$_2$)$_2$OMe | CH$_2$-c-Pr | 2 | CF$_3$ | |
| 1-2265 | CH$_2$O(CH$_2$)$_2$OMe | (CH$_2$)$_2$OMe | 2 | CF$_3$ | |
| 1-2266 | CH$_2$O(CH$_2$)$_2$OMe | (CH$_2$)$_3$OMe | 2 | CF$_3$ | |
| 1-2267 | CH$_2$O(CH$_2$)$_2$OMe | (CH$_2$)$_2$OEt | 2 | CF$_3$ | |
| 1-2268 | CH$_2$O(CH$_2$)$_2$OMe | (CH$_2$)$_2$OCH$_2$-c-Pr | 2 | CF$_3$ | |
| 1-2269 | CH$_2$O(CH$_2$)$_2$OEt | c-Pr | 0 | CF$_3$ | |
| 1-2270 | CH$_2$O(CH$_2$)$_2$OEt | CH$_2$-c-Pr | 0 | CF$_3$ | |
| 1-2271 | CH$_2$O(CH$_2$)$_2$OEt | (CH$_2$)$_2$OMe | 0 | CF$_3$ | |
| 1-2272 | CH$_2$O(CH$_2$)$_2$OEt | (CH$_2$)$_3$OMe | 0 | CF$_3$ | |
| 1-2273 | CH$_2$O(CH$_2$)$_2$OEt | (CH$_2$)$_2$OEt | 0 | CF$_3$ | |
| 1-2274 | CH$_2$O(CH$_2$)$_2$OEt | (CH$_2$)$_2$OCH$_2$-c-Pr | 0 | CF$_3$ | |
| 1-2275 | CH$_2$O(CH$_2$)$_2$OEt | c-Pr | 1 | CF$_3$ | |
| 1-2276 | CH$_2$O(CH$_2$)$_2$OEt | CH$_2$-c-Pr | 1 | CF$_3$ | |
| 1-2277 | CH$_2$O(CH$_2$)$_2$OEt | (CH$_2$)$_2$OMe | 1 | CF$_3$ | |
| 1-2278 | CH$_2$O(CH$_2$)$_2$OEt | (CH$_2$)$_3$OMe | 1 | CF$_3$ | |
| 1-2279 | CH$_2$O(CH$_2$)$_2$OEt | (CH$_2$)$_2$OEt | 1 | CF$_3$ | |
| 1-2280 | CH$_2$O(CH$_2$)$_2$OEt | (CH$_2$)$_2$OCH$_2$-c-Pr | 1 | CF$_3$ | |
| 1-2281 | CH$_2$O(CH$_2$)$_2$OEt | c-Pr | 2 | CF$_3$ | |
| 1-2282 | CH$_2$O(CH$_2$)$_2$OEt | CH$_2$-c-Pr | 2 | CF$_3$ | |
| 1-2283 | CH$_2$O(CH$_2$)$_2$OEt | (CH$_2$)$_2$OMe | 2 | CF$_3$ | |
| 1-2284 | CH$_2$O(CH$_2$)$_2$OEt | (CH$_2$)$_3$OMe | 2 | CF$_3$ | |
| 1-2285 | CH$_2$O(CH$_2$)$_2$OEt | (CH$_2$)$_2$OEt | 2 | CF$_3$ | |
| 1-2286 | CH$_2$O(CH$_2$)$_2$OEt | (CH$_2$)$_2$OCH$_2$-c-Pr | 2 | CF$_3$ | |
| 1-2287 | CH$_2$O(CH$_2$)$_3$OMe | c-Pr | 0 | CF$_3$ | |
| 1-2288 | CH$_2$O(CH$_2$)$_3$OMe | CH$_2$-c-Pr | 0 | CF$_3$ | |
| 1-2289 | CH$_2$O(CH$_2$)$_3$OMe | (CH$_2$)$_2$OMe | 0 | CF$_3$ | |
| 1-2290 | CH$_2$O(CH$_2$)$_3$OMe | (CH$_2$)$_3$OMe | 0 | CF$_3$ | |
| 1-2291 | CH$_2$O(CH$_2$)$_3$OMe | (CH$_2$)$_2$OEt | 0 | CF$_3$ | |
| 1-2292 | CH$_2$O(CH$_2$)$_3$OMe | (CH$_2$)$_2$OCH$_2$-c-Pr | 0 | CF$_3$ | |
| 1-2293 | CH$_2$O(CH$_2$)$_3$OMe | c-Pr | 1 | CF$_3$ | |
| 1-2294 | CH$_2$O(CH$_2$)$_3$OMe | CH$_2$-c-Pr | 1 | CF$_3$ | |
| 1-2295 | CH$_2$O(CH$_2$)$_3$OMe | (CH$_2$)$_2$OMe | 1 | CF$_3$ | |
| 1-2296 | CH$_2$O(CH$_2$)$_3$OMe | (CH$_2$)$_3$OMe | 1 | CF$_3$ | |
| 1-2297 | CH$_2$O(CH$_2$)$_3$OMe | (CH$_2$)$_2$OEt | 1 | CF$_3$ | |
| 1-2298 | CH$_2$O(CH$_2$)$_3$OMe | (CH$_2$)$_2$OCH$_2$-c-Pr | 1 | CF$_3$ | |
| 1-2299 | CH$_2$O(CH$_2$)$_3$OMe | c-Pr | 2 | CF$_3$ | |
| 1-2300 | CH$_2$O(CH$_2$)$_3$OMe | CH$_2$-c-Pr | 2 | CF$_3$ | |
| 1-2301 | CH$_2$O(CH$_2$)$_3$OMe | (CH$_2$)$_2$OMe | 2 | CF$_3$ | |
| 1-2302 | CH$_2$O(CH$_2$)$_3$OMe | (CH$_2$)$_3$OMe | 2 | CF$_3$ | |
| 1-2303 | CH$_2$O(CH$_2$)$_3$OMe | (CH$_2$)$_2$OEt | 2 | CF$_3$ | |
| 1-2304 | CH$_2$O(CH$_2$)$_3$OMe | (CH$_2$)$_2$OCH$_2$-c-Pr | 2 | CF$_3$ | |
| 1-2305 | CH$_2$OCH$_2$OMe | c-Pr | 0 | CF$_3$ | |
| 1-2306 | CH$_2$OCH$_2$OMe | CH$_2$-c-Pr | 0 | CF$_3$ | |
| 1-2307 | CH$_2$OCH$_2$OMe | (CH$_2$)$_2$OMe | 0 | CF$_3$ | |
| 1-2308 | CH$_2$OCH$_2$OMe | (CH$_2$)$_3$OMe | 0 | CF$_3$ | |
| 1-2309 | CH$_2$OCH$_2$OMe | (CH$_2$)$_2$OEt | 0 | CF$_3$ | |
| 1-2310 | CH$_2$OCH$_2$OMe | (CH$_2$)$_2$OCH$_2$-c-Pr | 0 | CF$_3$ | |
| 1-2311 | CH$_2$OCH$_2$OMe | c-Pr | 1 | CF$_3$ | |
| 1-2312 | CH$_2$OCH$_2$OMe | CH$_2$-c-Pr | 1 | CF$_3$ | |
| 1-2313 | CH$_2$OCH$_2$OMe | (CH$_2$)$_2$OMe | 1 | CF$_3$ | |
| 1-2314 | CH$_2$OCH$_2$OMe | (CH$_2$)$_3$OMe | 1 | CF$_3$ | |

TABLE A-continued

Compounds according to the invention of the general formula (I) in which $R^1$ is methyl, $R^4$ is hydrogen and q is zero

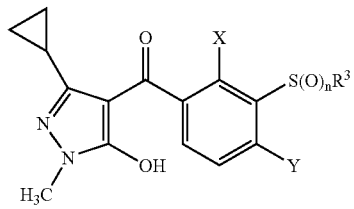

| No. | X | $R^3$ | n | Y | Physical data: $^1$H-NMR: δ[CDCl$_3$] |
|---|---|---|---|---|---|
| 1-2315 | CH$_2$OCH$_2$OMe | (CH$_2$)$_2$OEt | 1 | CF$_3$ | |
| 1-2316 | CH$_2$OCH$_2$OMe | (CH$_2$)$_2$OCH$_2$-c-Pr | 1 | CF$_3$ | |
| 1-2317 | CH$_2$OCH$_2$OMe | c-Pr | 2 | CF$_3$ | |
| 1-2318 | CH$_2$OCH$_2$OMe | CH$_2$-c-Pr | 2 | CF$_3$ | |
| 1-2319 | CH$_2$OCH$_2$OMe | (CH$_2$)$_2$OMe | 2 | CF$_3$ | |
| 1-2320 | CH$_2$OCH$_2$OMe | (CH$_2$)$_3$OMe | 2 | CF$_3$ | |
| 1-2321 | CH$_2$OCH$_2$OMe | (CH$_2$)$_2$OEt | 2 | CF$_3$ | |
| 1-2322 | CH$_2$OCH$_2$OMe | (CH$_2$)$_2$OCH$_2$-c-Pr | 2 | CF$_3$ | |
| 1-2323 | CH$_2$OCH$_2$OEt | c-Pr | 0 | CF$_3$ | |
| 1-2324 | CH$_2$OCH$_2$OEt | CH$_2$-c-Pr | 0 | CF$_3$ | |
| 1-2325 | CH$_2$OCH$_2$OEt | (CH$_2$)$_2$OMe | 0 | CF$_3$ | |
| 1-2326 | CH$_2$OCH$_2$OEt | (CH$_2$)$_3$OMe | 0 | CF$_3$ | |
| 1-2327 | CH$_2$OCH$_2$OEt | (CH$_2$)$_2$OEt | 0 | CF$_3$ | |
| 1-2328 | CH$_2$OCH$_2$OEt | (CH$_2$)$_2$OCH$_2$-c-Pr | 0 | CF$_3$ | |
| 1-2329 | CH$_2$OCH$_2$OEt | c-Pr | 1 | CF$_3$ | |
| 1-2330 | CH$_2$OCH$_2$OEt | CH$_2$-c-Pr | 1 | CF$_3$ | |
| 1-2331 | CH$_2$OCH$_2$OEt | (CH$_2$)$_2$OMe | 1 | CF$_3$ | |
| 1-2332 | CH$_2$OCH$_2$OEt | (CH$_2$)$_3$OMe | 1 | CF$_3$ | |
| 1-2333 | CH$_2$OCH$_2$OEt | (CH$_2$)$_2$OEt | 1 | CF$_3$ | |
| 1-2334 | CH$_2$OCH$_2$OEt | (CH$_2$)$_2$OCH$_2$-c-Pr | 1 | CF$_3$ | |
| 1-2335 | CH$_2$OCH$_2$OEt | c-Pr | 2 | CF$_3$ | |
| 1-2336 | CH$_2$OCH$_2$OEt | CH$_2$-c-Pr | 2 | CF$_3$ | |
| 1-2337 | CH$_2$OCH$_2$OEt | (CH$_2$)$_2$OMe | 2 | CF$_3$ | |
| 1-2338 | CH$_2$OCH$_2$OEt | (CH$_2$)$_3$OMe | 2 | CF$_3$ | |
| 1-2339 | CH$_2$OCH$_2$OEt | (CH$_2$)$_2$OEt | 2 | CF$_3$ | |
| 1-2340 | CH$_2$OCH$_2$OEt | (CH$_2$)$_2$OCH$_2$-c-Pr | 2 | CF$_3$ | |
| 1-2341 | CH$_2$O(CH$_2$)$_2$SO$_2$Me | c-Pr | 0 | CF$_3$ | |
| 1-2342 | CH$_2$O(CH$_2$)$_2$SO$_2$Me | CH$_2$-c-Pr | 0 | CF$_3$ | |
| 1-2343 | CH$_2$O(CH$_2$)$_2$SO$_2$Me | (CH$_2$)$_2$OMe | 0 | CF$_3$ | |
| 1-2344 | CH$_2$O(CH$_2$)$_2$SO$_2$Me | (CH$_2$)$_3$OMe | 0 | CF$_3$ | |
| 1-2345 | CH$_2$O(CH$_2$)$_2$SO$_2$Me | (CH$_2$)$_2$OEt | 0 | CF$_3$ | |
| 1-2346 | CH$_2$O(CH$_2$)$_2$SO$_2$Me | (CH$_2$)$_2$OCH$_2$-c-Pr | 0 | CF$_3$ | |
| 1-2347 | CH$_2$O(CH$_2$)$_2$SO$_2$Me | c-Pr | 1 | CF$_3$ | |
| 1-2348 | CH$_2$O(CH$_2$)$_2$SO$_2$Me | CH$_2$-c-Pr | 1 | CF$_3$ | |
| 1-2349 | CH$_2$O(CH$_2$)$_2$SO$_2$Me | (CH$_2$)$_2$OMe | 1 | CF$_3$ | |
| 1-2350 | CH$_2$O(CH$_2$)$_2$SO$_2$Me | (CH$_2$)$_3$OMe | 1 | CF$_3$ | |
| 1-2351 | CH$_2$O(CH$_2$)$_2$SO$_2$Me | (CH$_2$)$_2$OEt | 1 | CF$_3$ | |
| 1-2352 | CH$_2$O(CH$_2$)$_2$SO$_2$Me | (CH$_2$)$_2$OCH$_2$-c-Pr | 1 | CF$_3$ | |
| 1-2353 | CH$_2$O(CH$_2$)$_2$SO$_2$Me | c-Pr | 2 | CF$_3$ | |
| 1-2354 | CH$_2$O(CH$_2$)$_2$SO$_2$Me | CH$_2$-c-Pr | 2 | CF$_3$ | |
| 1-2355 | CH$_2$O(CH$_2$)$_2$SO$_2$Me | (CH$_2$)$_2$OMe | 2 | CF$_3$ | |
| 1-2356 | CH$_2$O(CH$_2$)$_2$SO$_2$Me | (CH$_2$)$_3$OMe | 2 | CF$_3$ | |
| 1-2357 | CH$_2$O(CH$_2$)$_2$SO$_2$Me | (CH$_2$)$_2$OEt | 2 | CF$_3$ | |
| 1-2358 | CH$_2$O(CH$_2$)$_2$SO$_2$Me | (CH$_2$)$_2$OCH$_2$-c-Pr | 2 | CF$_3$ | |
| 1-2359 | CH$_2$SO$_2$(CH$_2$)$_2$OMe | c-Pr | 0 | CF$_3$ | |
| 1-2360 | CH$_2$SO$_2$(CH$_2$)$_2$OMe | CH$_2$-c-Pr | 0 | CF$_3$ | |
| 1-2361 | CH$_2$SO$_2$(CH$_2$)$_2$OMe | (CH$_2$)$_2$OMe | 0 | CF$_3$ | |
| 1-2362 | CH$_2$SO$_2$(CH$_2$)$_2$OMe | (CH$_2$)$_3$OMe | 0 | CF$_3$ | |
| 1-2363 | CH$_2$SO$_2$(CH$_2$)$_2$OMe | (CH$_2$)$_2$OEt | 0 | CF$_3$ | |
| 1-2364 | CH$_2$SO$_2$(CH$_2$)$_2$OMe | (CH$_2$)$_2$OCH$_2$-c-Pr | 0 | CF$_3$ | |
| 1-2365 | CH$_2$SO$_2$(CH$_2$)$_2$OMe | c-Pr | 1 | CF$_3$ | |
| 1-2366 | CH$_2$SO$_2$(CH$_2$)$_2$OMe | CH$_2$-c-Pr | 1 | CF$_3$ | |
| 1-2367 | CH$_2$SO$_2$(CH$_2$)$_2$OMe | (CH$_2$)$_2$OMe | 1 | CF$_3$ | |
| 1-2368 | CH$_2$SO$_2$(CH$_2$)$_2$OMe | (CH$_2$)$_3$OMe | 1 | CF$_3$ | |
| 1-2369 | CH$_2$SO$_2$(CH$_2$)$_2$OMe | (CH$_2$)$_2$OEt | 1 | CF$_3$ | |
| 1-2370 | CH$_2$SO$_2$(CH$_2$)$_2$OMe | (CH$_2$)$_2$OCH$_2$-c-Pr | 1 | CF$_3$ | |
| 1-2371 | CH$_2$SO$_2$(CH$_2$)$_2$OMe | c-Pr | 2 | CF$_3$ | |
| 1-2372 | CH$_2$SO$_2$(CH$_2$)$_2$OMe | CH$_2$-c-Pr | 2 | CF$_3$ | |
| 1-2373 | CH$_2$SO$_2$(CH$_2$)$_2$OMe | (CH$_2$)$_2$OMe | 2 | CF$_3$ | |
| 1-2374 | CH$_2$SO$_2$(CH$_2$)$_2$OMe | (CH$_2$)$_3$OMe | 2 | CF$_3$ | |
| 1-2375 | CH$_2$SO$_2$(CH$_2$)$_2$OMe | (CH$_2$)$_2$OEt | 2 | CF$_3$ | |
| 1-2376 | CH$_2$SO$_2$(CH$_2$)$_2$OMe | (CH$_2$)$_2$OCH$_2$-c-Pr | 2 | CF$_3$ | |
| 1-2377 | CH$_2$SO$_2$(CH$_2$)$_2$SO$_2$Me | c-Pr | 0 | CF$_3$ | |

TABLE A-continued

Compounds according to the invention of the general formula (I) in which $R^1$ is methyl, $R^4$ is hydrogen and q is zero

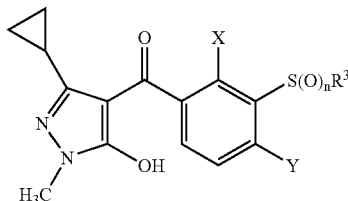

| No. | X | $R^3$ | n | Y | Physical data: $^1$H-NMR: δ[CDCl$_3$] |
|---|---|---|---|---|---|
| 1-2378 | CH$_2$SO$_2$(CH$_2$)$_2$SO$_2$Me | CH$_2$-c-Pr | 0 | CF$_3$ | |
| 1-2379 | CH$_2$SO$_2$(CH$_2$)$_2$SO$_2$Me | (CH$_2$)$_2$OMe | 0 | CF$_3$ | |
| 1-2380 | CH$_2$SO$_2$(CH$_2$)$_2$SO$_2$Me | (CH$_2$)$_3$OMe | 0 | CF$_3$ | |
| 1-2381 | CH$_2$SO$_2$(CH$_2$)$_2$SO$_2$Me | (CH$_2$)$_2$OEt | 0 | CF$_3$ | |
| 1-2382 | CH$_2$SO$_2$(CH$_2$)$_2$SO$_2$Me | (CH$_2$)$_2$OCH$_2$-c-Pr | 0 | CF$_3$ | |
| 1-2383 | CH$_2$SO$_2$(CH$_2$)$_2$SO$_2$Me | c-Pr | 1 | CF$_3$ | |
| 1-2384 | CH$_2$SO$_2$(CH$_2$)$_2$SO$_2$Me | CH$_2$-c-Pr | 1 | CF$_3$ | |
| 1-2385 | CH$_2$SO$_2$(CH$_2$)$_2$SO$_2$Me | (CH$_2$)$_2$OMe | 1 | CF$_3$ | |
| 1-2386 | CH$_2$SO$_2$(CH$_2$)$_2$SO$_2$Me | (CH$_2$)$_3$OMe | 1 | CF$_3$ | |
| 1-2387 | CH$_2$SO$_2$(CH$_2$)$_2$SO$_2$Me | (CH$_2$)$_2$OEt | 1 | CF$_3$ | |
| 1-2388 | CH$_2$SO$_2$(CH$_2$)$_2$SO$_2$Me | (CH$_2$)$_2$OCH$_2$-c-Pr | 1 | CF$_3$ | |
| 1-2389 | CH$_2$SO$_2$(CH$_2$)$_2$SO$_2$Me | c-Pr | 2 | CF$_3$ | |
| 1-2390 | CH$_2$SO$_2$(CH$_2$)$_2$SO$_2$Me | CH$_2$-c-Pr | 2 | CF$_3$ | |
| 1-2391 | CH$_2$SO$_2$(CH$_2$)$_2$SO$_2$Me | (CH$_2$)$_2$OMe | 2 | CF$_3$ | |
| 1-2392 | CH$_2$SO$_2$(CH$_2$)$_2$SO$_2$Me | (CH$_2$)$_3$OMe | 2 | CF$_3$ | |
| 1-2393 | CH$_2$SO$_2$(CH$_2$)$_2$SO$_2$Me | (CH$_2$)$_2$OEt | 2 | CF$_3$ | |
| 1-2394 | CH$_2$SO$_2$(CH$_2$)$_2$SO$_2$Me | (CH$_2$)$_2$OCH$_2$-c-Pr | 2 | CF$_3$ | |

Very particular preference is also given to all of the compounds of Nos. 1-1 to 1-2394 mentioned above in which $R^4$ is n-propylsulfonyl.

Very particular preference is also given to all of the compounds of Nos. 1-1 to 1-2394 mentioned above in which $R^4$ is phenylsulfonyl.

Very particular preference is also given to all of the compounds of Nos. 1-1 to 1-2394 mentioned above in which $R^4$ is methoxyethylsulfonyl.

Very particular preference is also given to all of the compounds of Nos. 1-1 to 1-2394 mentioned above in which $R^4$ is benzoylmethyl.

Very particular preference is also given to all of the compounds of Nos. 1-1 to 1-2394 mentioned above in which $R^4$ is 4-methylphenylsulfonyl.

Very particular preference is also given to all of the compounds of Nos. 1-1 to 1-2394 mentioned above in which $R^4$ is thien-2-ylsulfonyl.

Very particular preference is also given to all of the compounds of Nos. 1-1 to 1-2394 mentioned above in which $R^4$ is benzoyl.

Very particular preference is also given to all of the compounds of Nos. 1-1 to 1-2394 mentioned above in which $R^4$ is 4-methylbenzoylmethyl.

Very particular preference is also given to all of the compounds of Nos. 1-1 to 1-2394 mentioned above in which $R^4$ is (ethylthio)carbonyl.

B. FORMULATION EXAMPLES

1. Dust

A dust is obtained by mixing 10 parts by weight of a compound of general formula (I) and 90 parts by weight of talc as inert substance and comminuting the mixture in a hammer mill.

2. Dispersible Powder

A wettable powder which is readily dispersible in water is obtained by mixing 25 parts by weight of a compound of general formula (I), 64 parts by weight of kaolin-containing quartz as inert material, 10 parts by weight of potassium lignosulfonate and 1 part by weight of sodium oleoylmethyltauride as wetter and dispersant, and grinding the mixture in a pinned-disk mill.

3. Dispersion Concentrate

A dispersion concentrate which is readily dispersible in water is obtained by mixing 20 parts by weight of a compound of general formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

4. Emulsifiable Concentrate

An emulsifiable concentrate is obtained from 15 parts by weight of a compound of general formula (I), 75 parts by weight of cyclohexanone as solvent and 10 parts by weight of oxethylated nonylphenol as emulsifier.

5. Water-Dispersible Granules

Water-dispersible granules are obtained by mixing
75 parts by weight of a compound of general formula (I),
10" calcium lignosulfonate,
5" sodium lauryl sulfate,
3" polyvinyl alcohol and
7" kaolin, grinding the mixture in a pinned-disk mill and granulating the powder in a fluidized bed by spraying on water as granulation liquid.

Water-dispersible granules are also obtained by homogenizing and precomminuting, in a colloid mill,
25 parts by weight of a compound of general formula (I),
5" sodium 2,2'-dinaphthylmethane-6,6'-disulfonate,
2" sodium oleoylmethyltauride,
1" polyvinyl alcohol,
17" calcium carbonate and
50" water,
subsequently grinding the mixture in a bead mill, and atomizing and drying the resulting suspension in a spray tower by means of a single-substance nozzle.

C. BIOLOGICAL EXAMPLES

1. Pre-Emergence Herbicidal Action Against Harmful Plants

Seeds or rhizome pieces of mono- and dicotyledonous harmful plants are placed in sandy loam in pots of a diameter of 9 to 13 cm and covered with soil. The herbicides, formulated as emulsifiable concentrates or dusts, are applied to the surface of the covering soil in the form of aqueous dispersions or suspensions or emulsions at an application rate of 300 to 800 l of water/ha (converted), at a dosage of 320 grams per hectare. For further cultivation of the plants, the pots are then kept in a greenhouse under optimum conditions. The visual scoring of the damage to the harmful plants is carried out 3-4 weeks after the treatment. Here, the compounds of Nos. 1-3, 1-15, 1-44 and 1-1407 show an activity of at least 90% against *Echinochloa crus galli*. The compounds of Nos. 1-15, 1-45, 1-1407 and 1-1419 show an activity of at least 90% against *Abutilon theophrasti*. The compounds of Nos. 1-3, 1-45, 1-1406 and 1-1418 show an activity of at least 90% against *Amaranthus retroflexus*. The compounds of Nos. 1-44, 1-1406, 1-1407 and 1-1419 show an activity of at least 90% against *Stellaria media*.

2. Post-Emergence Herbicidal Action Against Harmful Plants

Seeds of mono- and dicotyledonous harmful plants are placed in sandy loam in cardboard pots, covered with soil and grown in the greenhouse under good growth conditions. Two to three weeks after sowing, the test plants are treated at the three-leaf stage. The compounds according to the invention, which are formulated as wettable powders or as emulsion concentrates, are sprayed at an application rate of 600 to 800 l of water/ha (converted) in a dosage of 80 grams per hectare onto the surface of the green plant parts. The visual scoring of the damage to the harmful plants is carried out 3-4 weeks after the treatment. Here, the compounds of Nos. 1-39, 1-40, 1-1382 and 1-2091 show an activity of at least 90% against *Echinochloa crus galli*. The compounds of Nos. 1-3, 1-44 and 1-2091 shown an activity of at least 90% against *Abutilon theophrasti*. The compounds of Nos. 1-39, 1-40 and 1-1382 show an activity of at least 90% against *Veronica persica*. The compounds of Nos. 1-3, 1-38, 1-39, 1-1406 and 1-1407 show an activity of at least 90% against *Stellaria media*.

3. Comparative Tests

To demonstrate the superiority of the compounds according to the invention over compounds known from the prior art (WO 97/41106 and WO 00/03993), the herbicidal activity against harmful plants and the damage of crop plants under the conditions mentioned above was compared in the comparative tests by the pre- and post-emergence method. The comparative tests of Tables 1 to 24 below show the superiority of the compounds according to the invention over the compounds known from the prior art.

The Abbreviations Used Denote:
Harmful Plants
ABUTH *Abutilon theophrasti* ALOMY *Alopecurus myosuroides*
AMARE *Amaranthus retroflexus* AVEFA *Avena fatua*
CHEAL *Chenopodium album* ECHCG *Echinochloa crus galli*
GALAP *Galium aparine* LOLMU *Lolium multiflorum*
MATIN *Matricaria inodora* PHBPU *Pharbitis purpureum*
POLCO *Fallopia convolvulus* STEME *Stellaria media*
VERPE *Veronica persica* VIOTR *Viola tricolor*
XANST *Xanthium strumarium*
Crop Plants
GLXMA *Glycine max* (soybeans) TRZAS *Triticum aestivum* (wheat)
ZEAMX *Zea mays* (corn)

TABLE 1

Pre-emergence activity

| Compound No. | Dosage [g of a.i./ha] | Herbicidal activity in % against VIOTR |
|---|---|---|
| 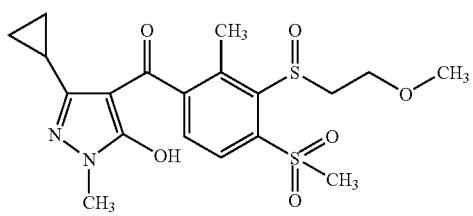 example according to the invention No. 1-45 | 80 | 70 |

TABLE 1-continued

Pre-emergence activity

| Compound No. | Dosage [g of a.i./ha] | Herbicidal activity in % against VIOTR |
|---|---|---|
| *(structure: cyclopropyl-pyrazole-OH-N-CH₃ linked via C=O to methyl-phenyl bearing S(=O)-CH₂CH₃ and S(=O)₂-CH₃ groups)* compound known from the prior art | 80 | 60 |

TABLE 2

Pre-emergence activity

| Compound No. | Dosage [g of a.i./ha] | Herbicidal activity in % against | | |
|---|---|---|---|---|
| | | PHBPU | POLCO | XANST |
| *(structure: cyclopropyl-pyrazole-OH-N-CH₃ linked via C=O to methyl-phenyl bearing S(=O)₂-CH₂CH₂-O-CH₃ and S(=O)₂-CH₃ groups)* example according to the invention No. 1-51 | 320 | 60 | 60 | 70 |
| *(structure: cyclopropyl-pyrazole-OH-N-CH₃ linked via C=O to methyl-phenyl bearing S(=O)-CH₂CH₃ and S(=O)₂-CH₃ groups)* compound known from the prior art | 320 | 20 | 20 | 0 |

TABLE 3

Pre-emergence activity

| Compound No. | Dosage [g of a.i./ha] | Herbicidal activity in % against | | |
|---|---|---|---|---|
| | | PHBPU | POLCO | XANST |
| *(structure shown)* example according to the invention No. 1-50 | 320 | 50 | 50 | 60 |
| *(structure shown)* compound known from the prior art | 320 | 20 | 20 | 0 |

TABLE 4

Pre-emergence activity

| Compound No. | Dosage [g of a.i./ha] | Herbicidal activity in % against | | |
|---|---|---|---|---|
| | | MATIN | STEME | VERPE |
| *(structure shown)* example according to the invention N. 1-1407 | 80 | 60 | 90 | 90 |
| *(structure shown)* compound known from the prior art | 80 | 30 | 60 | 30 |

TABLE 5

Pre-emergence activity

| Compound No. | Dosage [g of a.i./ha] | Herbicidal activity in % against | |
|---|---|---|---|
| | | ABUTH | MATIN |
| cyclopropyl-pyrazole structure (1-methyl-5-hydroxy-3-cyclopropyl-pyrazol-4-yl) ketone with 2-methyl-3-(2-methoxyethylthio)-4-trifluoromethylphenyl group<br>example according to the invention No. 1-2091 | 320 | 100 | 60 |
| cyclopropyl-pyrazole structure with 2-methyl-3-(methylthio)-4-trifluoromethylphenyl group<br>compound known from the prior art | 320 | 50 | 0 |

TABLE 6

Pre-emergence activity

| Compound No. | Dosage [g of a.i./ha] | Herbicidal activity in % against | |
|---|---|---|---|
| | | ABUTH | MATIN |
| cyclopropyl-pyrazole structure with 2-methyl-3-(2-methoxyethylthio)-4-trifluoromethylphenyl group<br>example according to the invention No. 1-2091 | 320 | 100 | 60 |
| cyclopropyl-pyrazole structure with 2-methyl-3-(ethylthio)-4-trifluoromethylphenyl group<br>compound known from the prior art | 320 | 90 | 0 |

TABLE 7

Pre-emergence activity

| Compound No. | Dosage [g of a.i./ha] | Herbicidal activity in % against | | | | |
|---|---|---|---|---|---|---|
| | | ABUTH | AMARE | MATIN | POLCO | VIOTR |
| 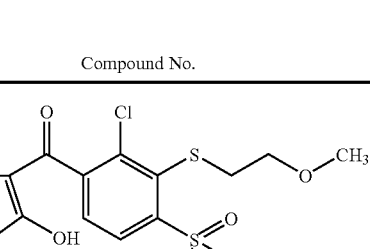<br>example according to the invention No. 1-3 | 320 | 100 | 100 | 60 | 50 | 100 |
| 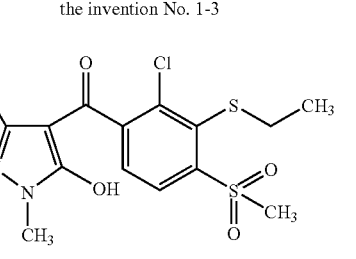<br>compound known from the prior art | 320 | 70 | 90 | 0 | 0 | 50 |

TABLE 8

Pre-emergence activity

| Compound No. | Dosage [g of a.i./ha] | Herbicidal activity in % against | | | | |
|---|---|---|---|---|---|---|
| | | ABUTH | AMARE | MATIN | POLCO | VIOTR |
| 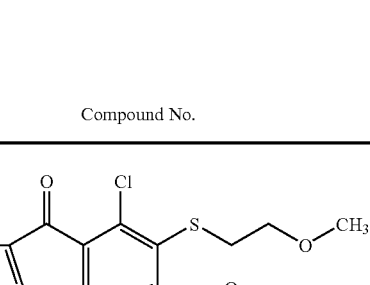<br>example according to the invention No. 1-3 | 320 | 100 | 100 | 60 | 50 | 100 |
| 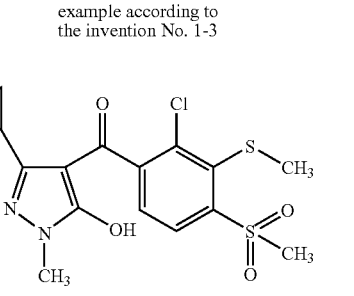<br>compound known from the prior art | 320 | 60 | 90 | 0 | 40 | 50 |

TABLE 9

Post-emergence activity

| Compound No. | Dosage [g of a.i./ha] | Herbicidal activity in % against | | |
|---|---|---|---|---|
| | | ECHCG | VIOTR | XANST |
| example according to the invention No. 1-39 | 80 | 90 | 90 | 90 |
| compound known from the prior art | 80 | 80 | 70 | 80 |

TABLE 10

Post-emergence activity

| Compound No. | Dosage [g of a.i./ha] | Herbicidal activity in % against | | |
|---|---|---|---|---|
| | | ECHCG | VIOTR | XANST |
| example according to the invention No. 1-38 | 80 | 100 | 90 | 90 |
| compound known from the prior art | 80 | 80 | 70 | 60 |

TABLE 11

Post-emergence activity

| Compound No. | Dosage [g of a.i./ha] | Herbicidal activity in % against | | |
|---|---|---|---|---|
| | | PHBPU | POLCO | VIOTR |
| example according to the invention No. 1-41 | 80 | 60 | 70 | 80 |
| compound known from the prior art | 80 | 40 | 50 | 70 |

TABLE 12

Post-emergence activity

| Compound No. | Dosage [g of a.i./ha] | Herbicidal activity in % against | | Damage to |
|---|---|---|---|---|
| | | VERPE | VIOTR | TRZAS |
| example according to the invention No. 1-45 | 80 | 100 | 70 | 20 |
| compound known from the prior art | 80 | 80 | 60 | 50 |

TABLE 13

| | | Post-emergence activity | | | | |
|---|---|---|---|---|---|---|
| | Dosage [g of | Herbicidal activity in % against | | | Damage to | |
| Compound No. | a.i./ha] | VERPE | VIOTR | GALAP | TRZAS | ZEAMX |
| 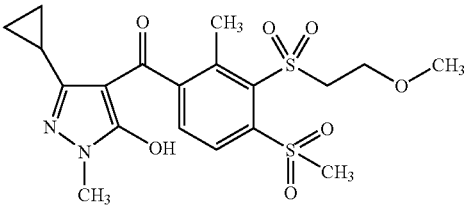 example according to the invention No. 1-51 | 20 | 90 | 70 | 50 | 0 | 0 |
| 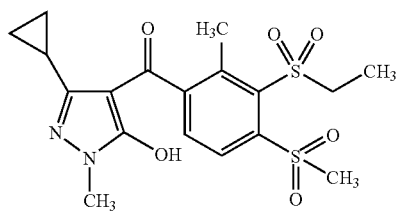 compound known from the prior art | 20 | 20 | 20 | 20 | 80 | 10 |

TABLE 14

| | | Pre-emergence activity | | | |
|---|---|---|---|---|---|
| | Dosage | Herbicidal activity in % | | Damage to | |
| Compound No. | [g of a.i./ha] | GALAP | CHEAL | TRZAS | GLXMA |
| 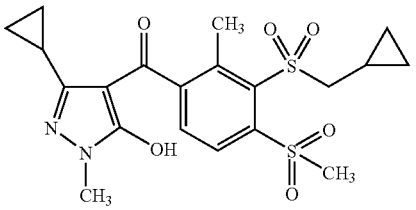 example according to the invention No. 1-50 | 320 | 100 | 100 | 0 | 0 |
| 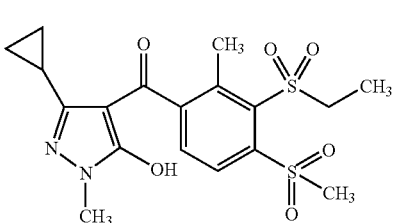 compound known from the prior art | 320 | 90 | 90 | 50 | 50 |

TABLE 15

Post-emergence activity

| Compound No. | Dosage [g of a.i./ha] | Herbicidal activity in % against | | | |
|---|---|---|---|---|---|
| | | ECHCG | PHBPU | MATIN | STEME |
| example according to the invention No. 1-1406 | 80 | 90 | 70 | 70 | 100 |
| compound known from the prior art | 80 | 80 | 40 | 40 | 90 |

TABLE 16

Post-emergence activity

| Compound No. | Dosage [g of a.i./ha] | Herbicidal activity in % against | | | |
|---|---|---|---|---|---|
| | | ECHCG | PHBPU | MATIN | STEME |
| example according to the invention No. 1-1407 | 80 | 90 | 80 | 80 | 100 |
| compound known from the prior art | 80 | 80 | 40 | 40 | 90 |

TABLE 17

Pre-emergence activity

| Compound No. | Dosage [g of a.i./ha] | Herbicidal activity in % against | | |
|---|---|---|---|---|
| | | AMARE | STEME | VERPE |
| example according to the invention No. 1-1406 | 80 | 80 | 90 | 70 |
| compound known from the prior art | 80 | 70 | 80 | 50 |

TABLE 18

Post-emergence activity

| Compound No. | Dosage [g of a.i./ha] | Herbicidal activity in % against | |
|---|---|---|---|
| | | ECHCG | ABUTH |
| example according to the invention No. 1-2091 | 20 | 80 | 80 |
| compound known from the prior art | 20 | 60 | 70 |

TABLE 19

Post-emergene activity

| Compound No. | Dosage [g of a.i./ha] | Herbicidal activity in % against | | |
|---|---|---|---|---|
| | | ABUTH | MATIN | VIOTR |
| example according to the invention No. 1-3 | 80 | 90 | 70 | 70 |
| compound known from the prior art | 80 | 80 | 0 | 60 |

TABLE 20

Post-emergence activity

| Compound No. | Dosage [g of a.i./ha] | Herbicidal activity in % against | | |
|---|---|---|---|---|
| | | ABUTH | MATIN | VIOTR |
| example according to the invention No. 1-3 | 80 | 90 | 70 | 70 |
| compound known from the prior art | 80 | 80 | 30 | 60 |

TABLE 21

Post-emergence activity

| Compound No. | Dosage [g of a.i./ha] | Herbicidal activity in % against | | |
|---|---|---|---|---|
| | | PHBPU | STEME | VERPE |
| example according to the invention No. 1-3 | 80 | 60 | 90 | 100 |
| compound known from the prior art | 80 | 50 | 80 | 80 |

TABLE 22

Post-emergence activity

| Compound No. | Dosage [g of a.i./ha] | Herbicidal activity in % against | |
|---|---|---|---|
| | | ABUTH | XANST |
| example according to the invention No. 1-1370 | 20 | 60 | 70 |
| compound known from the prior art | 20 | 40 | 50 |

TABLE 23

Post-emergence activity

| Compound No. | Dosage [g of a.i./ha] | Herbicidal activity in % against | | | | |
|---|---|---|---|---|---|---|
| | | ALOMY | AVEFA | ECHCG | LOLMU | ABUTH |
| example according to the invention No. 1-1382 | 80 | 70 | 50 | 90 | 60 | 70 |
| compound known from the prior art | 80 | 20 | 20 | 30 | 20 | 60 |

TABLE 24

Post-emergence activity

| Compound No. | Dosage [g of a.i./ha] | Herbicidal activity in % against | | | | |
|---|---|---|---|---|---|---|
| | | GALAP | MATIN | STEME | VERPE | XANST |
| example according to the invention No. 1-1382 | 80 | 70 | 50 | 100 | 90 | 90 |
| compound known from the prior art | 80 | 40 | 0 | 80 | 60 | 70 |

The invention claimed is:

1. A 3-cyclopropyl-4-(3-thiobenzoyl)pyrazole of formula (I) or a salt thereof

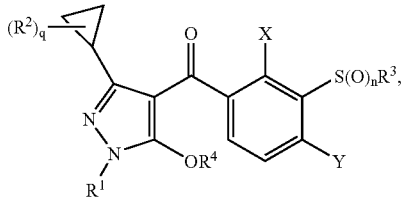

in which
R$^1$ is (C$_1$-C$_4$)-alkyl,
R$^2$ is halogen or (C$_1$-C$_4$)-alkyl,
R$^3$ is (C$_3$-C$_8$)-cycloalkyl, (C$_3$-C$_8$)-cycloalkyl-(C$_1$-C$_9$)-alkyl, (C$_2$-C$_6$)-alkenyl, (C$_2$-C$_6$)-alkynyl, (C$_1$-C$_6$)-haloalkyl, (C$_3$-C$_8$)-halocycloalkyl-(C$_1$-C$_9$)-alkyl, (C$_2$-C$_6$)-haloalkenyl, (C$_2$-C$_6$)-haloalkynyl, (C$_2$-C$_6$)-nitroalkyl, phenyl, (C$_3$-C$_8$)-cycloalkoxy-(C$_1$-C$_9$)-alkyl, (C$_3$-C$_8$)-cycloalkyl-(C$_1$-C$_9$)-alkoxy-(C$_1$-C$_9$)-alkyl, (C$_1$-C$_6$)-alkoxy-(C$_1$-C$_9$)-alkyl, (C$_2$-C$_6$)-alkenyloxy-(C$_1$-C$_9$)-alkyl, (C$_2$-C$_6$)-alkynyloxy-(C$_1$-C$_9$)-alkyl, (C$_1$-C$_6$)-haloalkoxy-(C$_1$-C$_9$)-alkyl, (C$_3$-C$_8$)-halocycloalkyl-(C$_1$-C$_9$)-alkoxy-(C$_1$-C$_9$)-alkyl, (C$_2$-C$_6$)-haloalkenyloxy-(C$_1$-C$_9$)-alkyl, (C$_2$-C$_6$)-haloalkynyloxy-(C$_1$-C$_9$)-alkyl, (C$_2$-C$_6$)-nitroalkoxy-(C$_1$-C$_9$)-alkyl, phenyloxy-(C$_1$-C$_9$)-alkyl, where the phenyl group may in each case be substituted by m identical or different radicals selected from the group consisting of (C$_1$-C$_3$)-alkyl, halogen, nitro, and (C$_1$-C$_3$)-alkoxy,
R$^4$ is hydrogen, (C$_1$-C$_6$)-alkylsulfonyl, (C$_1$-C$_4$)-alkoxy-(C$_1$-C$_6$)-alkylsulfonyl, or is phenylsulfonyl, thien-2-ylsulfonyl, (ethylthio)carbonyl, benzoyl, benzoyl-(C$_1$-C$_6$)-alkyl or benzyl, each of which is substituted by m identical or different radicals selected from the group consisting of halogen, (C$_1$-C$_4$)-alkyl and (C$_1$-C$_4$)-alkoxy,
X and Y independently of one another are hydrogen, mercapto, nitro, halogen, cyano, thiocyanato, (C$_1$-C$_6$)-alkyl, (C$_1$-C$_6$)-haloalkyl, (C$_2$-C$_6$)-alkenyl, (C$_2$-C$_6$)-haloalkenyl, (C$_2$-C$_6$)-alkynyl, (C$_3$-C$_6$)-haloalkynyl, (C$_3$-C$_6$)-cycloalkyl, OR$^5$, methylsulfonylethoxymethyl, methylsulfonylethylsulfonylmethyl, methoxyethylsulfonylmethyl, OCOR$^5$, OSO$_2$R$^5$, S(O)$_n$R$^5$, SO$_2$OR$^5$, SO$_2$N(R$^5$)$_2$, (C$_1$-C$_3$)-alkoxy-(C$_1$-C$_3$)-alkoxy-(C$_1$-C$_3$)-alkyl, NR$^5$SO$_2$R$^5$, NR$^5$COR$^5$, (C$_1$-C$_6$)-alkyl-S(O)$_n$R$^5$, (C$_1$-C$_6$)-alkyl-OR$^5$, (C$_1$-C$_6$)-alkyl-OCOR$^5$, (C$_1$-C$_6$)-alkyl-OSO$_2$R$^5$, (C$_1$-C$_6$)-alkyl-SO$_2$OR$^5$, (C$_1$-C$_6$)-alkyl-SO$_2$N(R$^5$)$_2$ or (C$_1$-C$_6$)-alkyl-NR$^5$COR$^5$;
R$^5$ is hydrogen, (C$_1$-C$_6$)-alkyl, (C$_2$-C$_6$)-alkenyl, (C$_2$-C$_6$)-alkynyl, (C$_3$-C$_6$)-cycloalkyl, phenyl or phenyl-(C$_1$-C$_6$)-alkyl, wherein, if R5 is (C$_1$-C$_6$)-alkyl, (C$_2$-C$_6$)-alkenyl, (C$_2$-C$_6$)-alkynyl, (C$_3$-C$_6$)-cycloalkyl, phenyl or phenyl-(C$_1$-C$_6$)-alkyl, R5 can be substituted by s radicals selected from the group consisting of hydroxyl, mercapto, amino, cyano, nitro, thiocyanato, OR$^6$, SR$^6$, N(R$^6$)$_2$, NOR$^6$, OCOR$^6$, SCOR$^6$, NR$^6$COR$^6$, CO$_2$R$^6$, COSR$^6$, CON(R$^6$)$_2$, (C$_1$-C$_4$)-alkyliminooxy, (C$_1$-C$_4$)-alkoxyamino, (C$_1$-C$_4$)-alkylcarbonyl, (C$_1$-C$_4$)-alkoxy-(C$_2$-C$_6$)-alkoxycarbonyl and (C$_1$-C$_4$)-alkylsulfonyl;
R$^6$ is hydrogen, (C$_1$-C$_6$)-alkyl, (C$_2$-C$_6$)-alkenyl or (C$_2$-C$_6$)-alkynyl,
m is 0, 1, 2, 3, 4 or 5,
n is 0, 1 or 2,
q is 0, 1, 2, 3, 4 or 5,
s is 0, 1, 2 or 3,
with the proviso that R$^3$ is not (C$_1$-C$_6$)-haloalkyl if n is 0.

2. The 3-cyclopropyl-4-(3-thiobenzoyl)pyrazole as claimed in claim 1 wherein
R$^1$ is (C$_1$-C$_4$)-alkyl,
R$^2$ is halogen, methyl or ethyl,
R$^3$ is cyclopropyl, cyclopropylmethyl, cyclopropylmethoxyethyl, methoxyethyl, methoxypropyl, or ethoxyethyl,
R$^4$ is hydrogen, n-propylsulfonyl, phenylsulfonyl, methoxyethylsulfonyl, benzoylmethyl, benzoyl, 4-methylbenzoylmethyl, (ethylthio)carbonyl, 4-methylphenylsulfonyl, or thien-2-ylsulfonyl,
X is nitro, halogen, (C$_1$-C$_4$)-alkyl, trifluoromethyl, (C$_1$-C$_4$)-alkoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, or methylsulfonylethylsulfonylmethyl,
Y is halogen, trifluoromethyl, (C$_1$-C$_4$)-alkoxy, methylsulfonyl or ethylsulfonyl,
n is 0, 1 or 2,
q is 0, 1 or 2.

3. The 3-cyclopropyl-4-(3-thiobenzoyl)pyrazole as claimed in claim 1 wherein
R$^1$ is methyl or ethyl,
R$^3$ is cyclopropyl, cyclopropylmethyl, cyclopropylmethoxyethyl, methoxyethyl, methoxypropyl, or ethoxyethyl,
R$^4$ is hydrogen, n-propylsulfonyl, phenylsulfonyl, methoxyethylsulfonyl, benzoylmethyl, benzoyl, 4-methylbenzoylmethyl, (ethylthio)carbonyl, 4-methylphenylsulfonyl, or thien-2-ylsulfonyl,
X is nitro, bromine, chlorine, fluorine, methyl, ethyl, trifluoromethyl, methoxy, ethoxy, methylsulfonyl, methoxymethyl, methoxymethoxymethyl, ethoxyethoxymethyl, ethoxymethoxymethyl, methoxyethoxymethyl, methoxypropoxymethyl, methylsulfonylmethyl, methylsulfonylethoxymethyl, methoxyethylsulfonylmethyl, or methylsulfonylethylsulfonylmethyl,
Y is bromine, chlorine, fluorine, trifluoromethyl, methoxy, methylsulfonyl or ethylsulfonyl,
n is 0, 1 or 2,
q is 0.

4. A herbicidal composition which comprises a herbicidally effective amount of at least one 3-cyclopropyl-4-(3-thiobenzoyl)pyrazole of formula (I) or a salt thereof as claimed in claim 1.

5. The herbicidal composition as claimed in claim 4 as a mixture with formulation auxiliaries.

6. A method for controlling unwanted plants which comprises applying an effective amount of at least one compound of formula (I) as claimed in claim 1 to a plant or to a site of unwanted plant growth.

7. A herbicidal composition as claimed in claim 4 which is capable of controlling unwanted plants.

8. The composition as claimed in claim 7 a compound of formula (I) is capable of controlling unwanted plants in crops of useful plants.

9. The composition as claimed in claim 8 wherein the useful plants are transgenic useful plants.

* * * * *